US011753474B2

(12) United States Patent
Ackerman et al.

(10) Patent No.: US 11,753,474 B2
(45) Date of Patent: Sep. 12, 2023

(54) ANTI-DECTIN-2 ANTIBODIES

(71) Applicant: Bolt Biotherapeutics, Inc., Redwood City, CA (US)

(72) Inventors: Shelley Erin Ackerman, Redwood City, CA (US); David Dornan, Redwood City, CA (US); Karla A. Henning, Redwood City, CA (US); Justin A. Kenkel, Redwood City, CA (US)

(73) Assignee: Bolt Biotherapeutics, Inc., Redwood City, CA (US)

( * ) Notice: Subject to any disclaimer, the term of this patent is extended or adjusted under 35 U.S.C. 154(b) by 0 days.

(21) Appl. No.: 17/592,323

(22) Filed: Feb. 3, 2022

(65) Prior Publication Data

US 2022/0153849 A1    May 19, 2022

Related U.S. Application Data

(63) Continuation of application No. PCT/US2021/030466, filed on May 3, 2021.

(60) Provisional application No. 63/018,952, filed on May 1, 2020.

(51) Int. Cl.
*C07K 16/28* (2006.01)
(52) U.S. Cl.
CPC .... *C07K 16/2851* (2013.01); *C07K 2317/565* (2013.01)
(58) Field of Classification Search
None
See application file for complete search history.

(56) References Cited

U.S. PATENT DOCUMENTS

| 10,995,148 B2 | 5/2021 | Avila et al. |
| 2019/0336615 A1 | 11/2019 | Thompson et al. |
| 2020/0354447 A1 | 11/2020 | Thompson et al. |
| 2021/0283262 A1 | 9/2021 | Dominy et al. |
| 2022/0127366 A1 | 4/2022 | Fotakis et al. |
| 2022/0169737 A1 | 6/2022 | Fotakis et al. |

FOREIGN PATENT DOCUMENTS

| WO | WO 2017/117269 A1 | 7/2017 |
| WO | WO 2019/006038 A1 | 1/2019 |

OTHER PUBLICATIONS

Schroeder et al. (J Allergy Clin Immunol 2010, 125:S41-S52).*
Lloyd et al. Protein Engineering, Design & Selection 2009, 22:159-168.*
Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Piche-Nicholas et al. MABS 2018, 10:81-94.*
Cantrell et al. Gynecologic Oncology vol. 137, Issue 3, Jun. 2015, pp. 581-588.*
European Patent Office, International Search Report in International Patent Application No. PCT/US2021/030466 (dated Aug. 31, 2021).
European Patent Office, Written Opinion in International Patent Application No. PCT/US2021/030466 (dated Aug. 31, 2021).
Parsons et al., "Dectin-2 Regulates the Effector Phase of House Dust Mite-Elicited Pulmonary Inflammation Independently From Its Role in Sensitization," *The Journal of Immunology*, 192(4): 1361-1371 (2014).
R&D Systems (bio-techne), "Human Dectin-2/CLEC6A Antibody," Monoclonal Mouse IgG$_{2B}$ Clone # 545925, Catalog No. MAB31141 (2020).
Brown et al., "C-type lectins in immunity and homeostasis," *Nat. Rev. Immunol.*, 18:374-389 (2018).
Cheng et al., "A pan-cancer single-cell transcriptional atlas of tumor infiltrating myeloid cells," *Cell*, 184: 792-809 (2021).
Goyal et al., "The Interaction of Human Pathogenic Fungi with C-Type Lectin Receptors," *Front. Immunol.*, 9: 1261 (2018).
Kenkel et al., "Dectin-2 Agonist Antibodies Reprogram Tumor-Associated Macrophages To Drive Anti-Tumor Immunity," *Cancer Research*, 82(Suppl. 12): Abstract 2883 (2022).
Kenkel et al., "BDC-3042: A Dectin-2 Agonist Antibodies for Tumor-Associated Macrophage-Directed Immunotherapy," *Journal for ImmunoTherapy of Cancer*, 10(Suppl. 2): A1397, Abstract 1348 (2022).
Kenkel et al., "Dectin-2, a Novel Target for Tumor Macrophage Reprogramming in Cancer Immunotherapy," *Journal for ImmunoTherapy of Cancer*, 9(Suppl. 2): Abstract 862 (2021).
Kersher et al., "The Dectin-2 family of C-type lectin-like receptors: an update," *Int. Immunol.*, 25(5): 271-277 (2013).
Kim et al., "Tumor-Associated Macrophages and Neutrophils in Tumor Microenvironment," *Mediators of Inflammation*, 2016: 6058147 (2016).
Kimura et al., "The innate immune receptor Dectin-2 mediates the phagocytosis of cancer cells by Kupffer cells for the suppression of liver metastasis," *PNAS*, 113(49): 14097-14102 (2016).
Molgora et al., "Turning enemies into allies—reprogramming tumor-associated macrophages for cancer therapy," *Med*, 2: 666-681 (2021).
Richards et al., "Optimization of antibody binding to FcγRIIa enhances macrophage phagocytosis of tumor cells," *Mol. Cancer Ther.*, 7(8): 2517-2527 (2008).

(Continued)

*Primary Examiner* — Sharon X Wen
(74) *Attorney, Agent, or Firm* — Leydig, Voit & Mayer, Ltd.

(57) ABSTRACT

The invention relates to dendritic cell-associated C-type lectin 2 (Dectin-2) binding agents, nucleic acids comprising the inventive binding agents, vectors and cells comprising the inventive nucleic acids, and compositions thereof. The invention also relates to methods of providing the inventive binding agents, methods for treating a disease, disorder, or condition in a mammal, and methods of stimulating an antigen presenting cell.

131 Claims, 7 Drawing Sheets

Specification includes a Sequence Listing.

(56) References Cited

OTHER PUBLICATIONS

Robinson et al., "Dectin-2 is a Syk-coupled pattern recognition receptor crucial for Th17 responses to fungal infection," *J. Exp. Med.*, 206(9): 2037-2051 (2009).
Saijo et al., "Dectin-2 Recognition of α-Mannans and Induction of Th17 Cell Differentiation Is Essential for Host Defense against *Candida albicans*," *Immunity*, 32: 681-691 (2010).
Saijo et al., "Dectin-1 and Dectin-2 in innate immunity against fungi," *Int. Immunol.*, 23(8): 467-472 (2011).
Sato et al., "Dectin-2 Is a Pattern Recognition Receptor for Fungi That Couples with the Fc Receptor γ Chain to Induce Innate Immune Responses," *J. Biol. Chem.*, 281(50): 38854-38866 (2006).
Van Dalen et al., "Molecular Repolarisation of Tumour-Associated Macrophages," *Molecules*, 24: 9 (2019).

\* cited by examiner

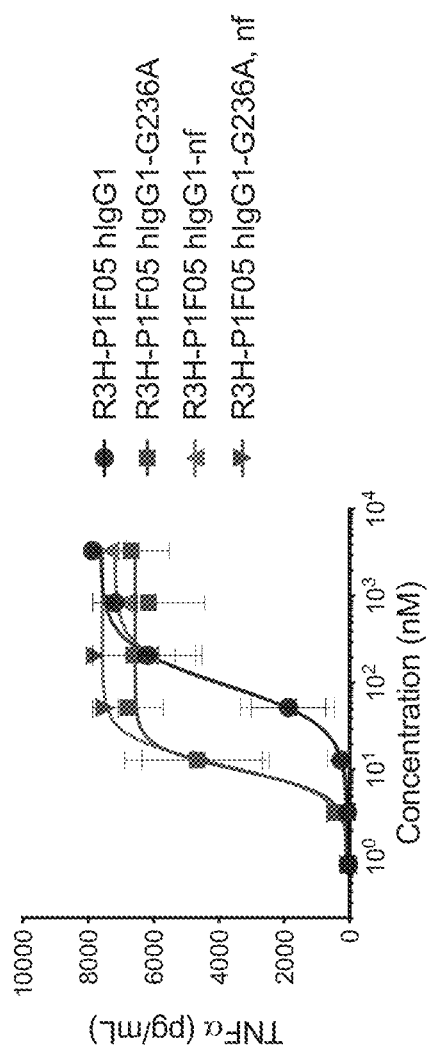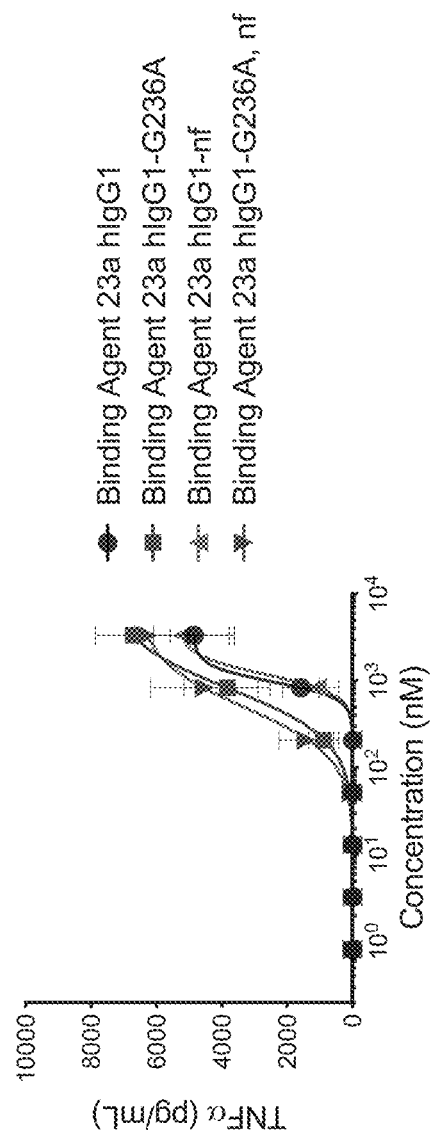

ANTI-DECTIN-2 ANTIBODIES

CROSS-REFERENCE TO PRIOR APPLICATIONS

This application is a continuation of International Patent Application No. PCT/US2021/030466, filed May 3, 2021, which claims benefit to U.S. Provisional Patent Application No. 63/018,952, filed May 1, 2020, each of which is hereby incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 222,069 Byte ASCII (Text) file named "759443 ST25.txt," created on Jan. 28, 2022.

BACKGROUND OF THE INVENTION

Dectin-2 (dendritic cell-associated C-type lectin 2, CLEC6A, CLEC4N, CLECSF10) belongs to the family of C-type lectin receptors. Dectin-2 is thought to primarily play a role in antifungal immunity, by binding to carbohydrate ligands such as mannans, which are typically found on fungal cell surfaces. Dectin-2 is expressed mainly by cells of myeloid lineage, including monocytes, macrophages and dendritic cells. Activation of the Dectin-2 pathway can elicit a pro-inflammatory immune response in these cells, including activation of the NF-κB pathway and subsequent production of pro-inflammatory cytokines, as well as increased phagocytic activity. A pro-inflammatory immune response driven by Dectin-2 activation on Dectin-2 expressing myeloid cells in the tumor microenvironment can ultimately lead to an anti-tumor immune response. Accordingly, agents that bind to Dectin-2, including those that act as Dectin-2 agonists, can be useful in the treatment of cancer.

There is still a need for additional methods of preventing and treating cancer given that most cancer patients ultimately fail standard of care therapies. Dectin-2 binding agents, including those that act to agonize the Dectin-2 signaling pathway, can be used to address this need.

BRIEF SUMMARY OF THE INVENTION

Provided herein are Dectin-2 binding agents comprising an immunoglobulin heavy chain variable region polypeptide and an immunoglobulin light chain variable region polypeptide. In some embodiments, the Dectin-2 binding agents comprise an immunoglobulin heavy chain variable region of any one of SEQ ID NOs: 243-282 or 324, or at least the CDRs thereof; and an immunoglobulin light chain variable region of any one of SEQ ID NOs: 283-322 or at least the CDRs thereof. In other embodiments, the Dectin-2 binding agents comprise an immunoglobulin heavy chain variable region polypeptide with an amino acid sequence that is at least 90% identical to any one of SEQ ID NOs: 243-282 or 324, and an immunoglobulin light chain variable region polypeptide with an amino acid sequence that is at least 90% identical to any one of SEQ ID NOs: 283-322. In yet other embodiments of the Dectin-2 binding agent, the immunoglobulin heavy chain variable region polypeptide comprises a complementarity determining region 1 (HCDR1) comprising any one of SEQ ID NOs: 1-30, a complementarity determining region 2 (HCDR2) comprising any one of SEQ ID NOs: 31-64, and a complementarity determining region 3 (HCDR3) comprising any one of SEQ ID NOs: 65-103 or 323; and/or the immunoglobulin light chain variable region polypeptide comprises a complementarity determining region 1 (LCDR1) comprising any one of SEQ ID NOs: 104-125, a complementarity determining region 2 (LCDR2) comprising any one of SEQ ID NOs: 126-148, and a complementarity determining region 3 (LCDR3) comprising any one of SEQ ID NOs: 149-181. In further embodiments, the Dectin-2 binding agents comprise an immunoglobulin heavy chain polypeptide of any one of SEQ ID NOs: 328-345, and an immunoglobulin light chain polypeptide of any one of SEQ ID NOs: 325-327. In still further embodiments, the Dectin-2 binding agents comprise an immunoglobulin heavy chain polypeptide that is at least 90% identical to any one of SEQ ID NOs: 328-345, and an immunoglobulin light chain polypeptide that is at least 90% identical to any one of SEQ ID NOs: 325-327. Also provided are nucleic acids encoding the Dectin-2 binding agents, or the individual heavy and light chains thereof vectors and cells comprising the nucleic acids; and compositions comprising the binding agents or nucleic acids.

Also provided is a method of preparing a binding agent as described herein, which method comprises expressing in a cell one or more nucleic acids encoding the heavy and light chain variable region polypeptides of the binding agent.

Also provided is a method for treating a disease, disorder, or condition in a mammal that is responsive to Dectin-2 activation or inhibition, which method comprises administering a binding agent as described herein, or conjugate thereof, to the mammal.

Also provided is a method of stimulating an antigen presenting cell (APC), which method comprises contacting an APC with a Dectin-2 binding agent at a dose and for a period of time sufficient to enhance Dectin-2 signaling in the APC, thereby generating a stimulated APC.

Additional aspects and embodiments of the invention are as provided in the following detailed description.

BRIEF DESCRIPTION OF THE DRAWINGS

FIGS. 5A and 5B are graphs of TNFα (pg/mL) secreted by M-CSF-treated human monocytes stimulated with different concentrations (nM) of each of the indicated antibodies.

DETAILED DESCRIPTION OF THE INVENTION

Figure 1:
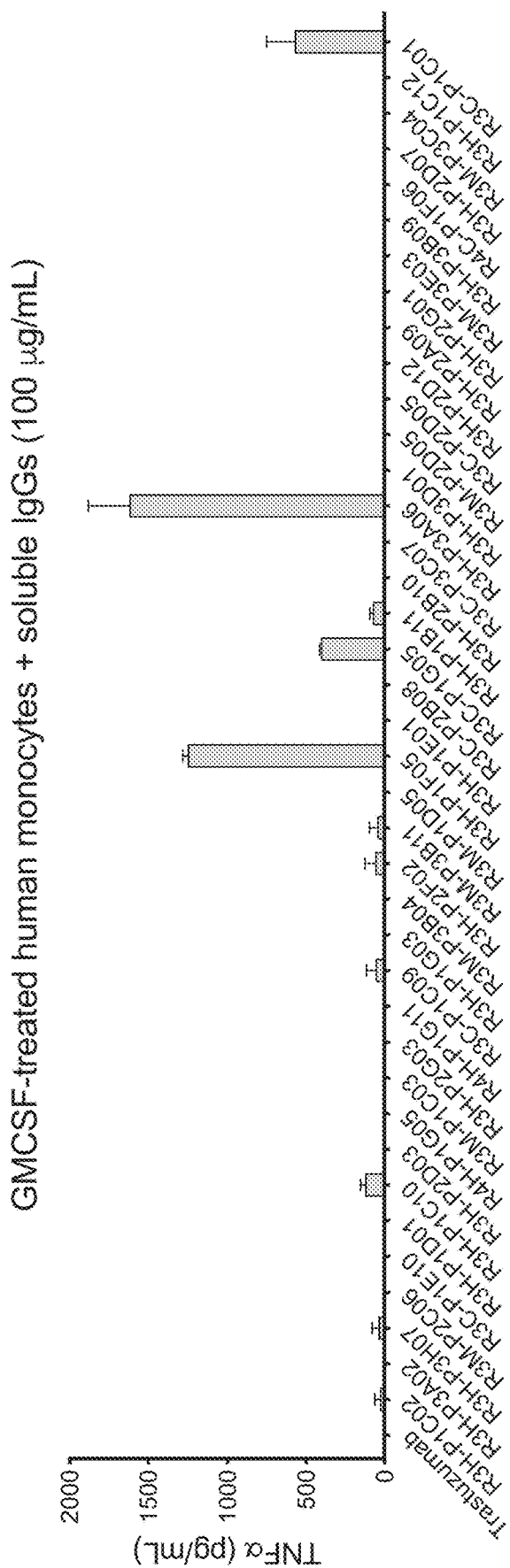
FIG. 1 is a bar graph of Tumor Necrosis Factor alpha (TNFα (pg/mL)) secreted by GM-CSF-treated human monocytes which have been exposed to certain soluble anti-Dectin-2 antibodies at a concentration of 100 μg/mL.

The invention provides a Dectin-2 binding agent comprising an immunoglobulin heavy chain variable region polypeptide and an immunoglobulin light chain variable region polypeptide. The Dectin-2 binding agent specifically binds Dectin-2, and allows for targeting Dectin-2 expressing cells, for instance, to activate (induce) one or more Dectin-2-associated pathways in the Dectin-2 expressing cells.

In some embodiments, the Dectin-2 binding agent binds Dectin-2, which is a receptor, without substantially inhibiting or preventing binding of one or more of its natural ligands to Dectin-2. In some embodiments, the Dectin-2 binding agent agonistically binds Dectin-2, thereby completely or partially activating Dectin-2 signaling in Dectin-2 expressing cells (e.g., for therapeutic purposes). In some embodiments, the Dectin-2 binding agent binds Dectin-2 as a monomer. In some embodiments, the Dectin-2 binding agent binds Dectin-2 as a homodimer or a heterodimer with another protein, such as Dectin-3. When the Dectin-2 binding agent binds to Dectin-2 as a homodimer or heterodimer (e.g., Dectin-2/Dectin-3 heterodimer), the binding agent can bind to the Dectin-2 prior to formation of the homodimer or heterodimer or, in other embodiments, the Dectin-2 binding agent binds Dectin-2 after it has formed a homodimer or heterodimer.

In some embodiments, the Dectin-2 binding agent binds to human Dectin-2, for example, a protein comprising SEQ ID NO: 346 (MMQEQQPQSTEKRGWLSRLWSVAGI-SIALLSACFIVSCVVTYHFTYGETGKRLSEL HSYHSSLTCFSEGTKVPAWGCCPASWKSFGSSCYFIS-SEEKVWSKSEQNCVEMGAHL VVFNTEAEQN-FIVQQLNESFSYFLGLSDPQGNNNWQWIDKTPYE-KNVRFWHLGEPN HSAEQCASIVFWKPTGWGWND-VICETRRNSICEMNKIYL). However, binding agents that bind to any Dectin-2 homolog or paralog also are encompassed. In some embodiments, the Dectin-2 protein comprises at least about 70%, about 75%, about 80%, about 85%, about 90%, about 91%, about 92%, about 93%, about 94%, about 95%, about 96%, about 97%, about 98%, about 99%, or more sequence identity to SEQ ID NO: 346. In some embodiments, the binding agent binds human and/or mouse Dectin-2.

Nucleic acid or amino acid sequence "identity," as referenced herein, can be determined by comparing a nucleic acid or amino acid sequence of interest to a reference nucleic acid or amino acid sequence. The percent identity is the number of nucleotides or amino acid residues that are the same (i.e., that are identical) as between the optimally aligned sequence of interest and the reference sequence divided by the length of the longest sequence (i.e., the length of either the sequence of interest or the reference sequence, whichever is longer). Alignment of sequences and calculation of percent identity can be performed using available software programs. Examples of such programs include CLUSTAL-W, T-Coffee, and ALIGN (for alignment of nucleic acid and amino acid sequences), BLAST programs (e.g., BLAST 2.1, BL2SEQ, BLASTp, BLASTn, and the like) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 106(10): 3770-3775 (2009), Durbin et al., eds., *Biological Sequence Analysis: Probalistic Models of Proteins and Nucleic Acids*, Cambridge University Press, Cambridge, UK (2009), Sod-ing, *Bioinformatics,* 21(7): 951-960 (2005), Altschul et al., *Nucleic Acids Res.*, 25(17): 3389-3402 (1997), and Gusfield, *Algorithms on Strings, Trees and Sequences*, Cambridge University Press, Cambridge UK (1997)). Percent (%) identity of sequences can be also calculated, for example, as $100\times[(\text{identical positions})/\min(TG_A, TG_B)]$, where $TG_A$ and $TG_B$ are the sum of the number of residues and internal gap positions in peptide sequences A and B in the alignment that minimizes $TG_A$ and $TG_B$. See, e.g., Russell et al., *J. Mol Biol.*, 244: 332-350 (1994).

The binding agent comprises Ig heavy and light chain variable region polypeptides that together form the antigen binding site. Each of the heavy and light chain variable regions are polypeptides comprising three complementarity determining regions (CDR1, CDR2, and CDR3) connected by framework regions. The binding agent can be any of a variety of types of binding agents known in the art that comprise Ig heavy and light chains. For instance, the binding agent can be an antibody, an antigen-binding antibody "fragment," or a T-cell receptor.

In some embodiments, the binding agent is a whole (or complete) antibody, which comprises an antigen binding domain comprising the Ig heavy and light variable domains as well as a fragment crystallizable (Fc) domain. An exemplary antibody structure is a tetramer composed of two pairs of polypeptide chains, each pair having one "light" (a smaller chain, such as about 25 kDa) and one "heavy" chain (a larger chain, such as about 50-70 kDa), typically connected by disulfide bonds. Each chain is composed of structural domains, which are referred to as immunoglobulin domains. These domains are classified into different categories by size and function, e.g., variable domains or regions on the light and heavy chains ($V_L$ and $V_H$, respectively) and constant domains or regions on the light and heavy chains ($C_L$ and $C_H$, respectively). The N-terminus of each chain defines a variable region, typically about 100 to 110 or more amino acids (but not limited thereto), referred to as the paratope, primarily responsible for antigen recognition, i.e., the antigen binding domain. Light chains are classified as either kappa or lambda. Heavy chains are classified as gamma, mu, alpha, delta, or epsilon, which in turn define the immunoglobulin classes, IgG, IgM, IgA, IgD and IgE, respectively. The classes can be further divided into subclasses. For instance, there are four IgG subclasses (IgG1, IgG2, IgG3, and IgG4) in humans, named in order of their abundance in serum (i.e., IgG1 is the most abundant).

In some embodiments, the binding agent is an antigen-binding antibody "fragment," which is a construct that comprises at least an antigen-binding region of an antibody, alone or with other components that together constitute the antigen-binding construct. Many different types of antibody "fragments" are known in the art, including, for instance, (i) a Fab fragment, which is a monovalent fragment consisting of the $V_L$, $V_H$, $C_L$, and $CH_1$ domains, (ii) a F(ab')2 fragment, which is a bivalent fragment comprising two Fab fragments linked by a disulfide bridge at the hinge region, (iii) a Fv fragment consisting of the $V_L$ and $V_H$ domains of a single arm of an antibody, (iv) a Fab' fragment, which results from breaking the disulfide bridge of an $F(ab')_2$ fragment using mild reducing conditions, (v) a disulfide-stabilized Fv fragment (dsFv), and (vi) a single chain Fv (scFv), which is a monovalent molecule consisting of the two domains of the Fv fragment (i.e., $V_L$ and $V_H$) joined by a synthetic linker which enables the two domains to be synthesized as a single polypeptide chain.

The antibody or antibody fragments can be part of a larger construct, for example, a conjugate or fusion construct of the antibody fragment to additional regions. For instance, in some embodiments, the antibody fragment can be fused to an Fc region as described herein. In other embodiments, the antibody fragment (e.g., a Fab or scFv) can be part of a chimeric antigen receptor or chimeric T-cell receptor, for instance, by fusing to a transmembrane domain (optionally with an intervening linker or "stalk" (e.g., hinge region)) and optional intercellular signaling domain. For instance, the antibody fragment can be fused to the gamma and/or delta chains of a t-cell receptor, so as to provide a T-cell receptor like construct that binds Dectin-2. In yet another embodiment, the antibody fragment is part of a bispecific T-cell engager (BiTEs) comprising a CD1 or CD3 binding domain and linker.

The antibody or antigen-binding antibody fragment can be monospecific for Dectin-2, or can be bispecific or multi-specific. For instance, in bivalent or multivalent antibodies or antibody fragments, the binding domains can be different, and each binding domain can target different epitopes of the same antigen or target different antigens. In certain embodiments, the antibody or antigen binding antibody fragment is bispecific or multi-specific, wherein at least one binding domain specifically binds to Dectin-2, and at least one binding domain specifically binds a tumor targeting protein. Examples of tumor targeting proteins include 5T4, ABL, ABCF1, ACVR1, ACVR1B, ACVR2, ACVR2B, ACVRL1, ADORA2A, Aggrecan, AGR2, AICDA, AIF1, AIGI, AKAP1, AKAP2, AMH, AMHR2, ANGPT1, ANGPT2, ANGPTL3, ANGPTL4, ANPEP, APC, APOC1, AR, aromatase, ATX, AX1, AZGP1 (zinc-a-glycoprotein), B7.1, B7.2, B7-H1, BAD, BAFF, BAG1, BAIL BCR, BCL2, BCL6, BDNF, BLNK, BLR1 (MDR15), BlyS, BMP1, BMP2, BMP3B (GDFIO), BMP4, BMP6, BMP8, BMPR1A, BMPR1B, BMPR2, BPAG1 (plectin), BRCA1, C19orf10 (IL27w), C3, C4A, C5, C5R1, CANT1, CAPRIN-1, CASP1, CASP4, CAV1, CCBP2 (D6/JAB61), CCL1 (1-309), CCLI1 (eotaxin), CCL13 (MCP-4), CCL15 (MIP-Id), CCL16 (HCC-4), CCL17 (TARC), CCL18 (PARC), CCL19 (MIP-3b), CCL2 (MCP-1), MCAF, CCL20 (MIP-3a), CCL21 (MEP-2), SLC, exodus-2, CCL22 (MDC/STC-I), CCL23 (MPIF-I), CCL24 (MPIF-2/eotaxin-2), CCL25 (TECK), CCL26 (eotaxin-3), CCL27 (CTACK/ILC), CCL28, CCL3 (MIP-Ia), CCL4 (MIPIb), CCL5 (RANTES), CCL7 (MCP-3), CCL8 (mcp-2), CCNA1, CCNA2, CCND1, CCNE1, CCNE2, CCR1 (CKR1/HM145), CCR2 (mcp-IRB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCR8 (CMKBR8/TERI/CKR-L1), CCR9 (GPR-9-6), CCRL1 (VSHK1), CCRL2 (L-CCR), CD164, CD19, CDIC, CD2, CD20, CD21, CD200, CD-22, CD24, CD27, CD28, CD3, CD33, CD35, CD37, CD38, CD3E, CD3G, CD3Z, CD4, CD38, CD40, CD40L, CD44, CD45RB, CD47, CD52, CD69, CD72, CD74, CD79A, CD79B, CD8, CD80, CD81, CD83, CD86, CD137, CD152, CD274, CDH1 (Ecadherin), CDH1O, CDH12, CDH13, CDH18, CDH19, CDH2O, CDH5, CDH7, CDH8, CDH9, CDK2, CDK3, CDK4, CDK5, CDK6, CDK7, CDK9, CDKN1A (p21Wap1/Cip1), CDKN1B (p27Kip1), CDKN1C, CDKN2A (p16INK4a), CDKN2B, CDKN2C, CDKN3, CEBPB, CERI, CHGA, CHGB, Chitinase, CHST1O, CKLFSF2, CKLFSF3, CKLFSF4, CKLFSF5, CKLFSF6, CKLFSF7, CKLFSF8, CLDN3, CLDN7 (claudin-7), CLN3, CLU (clusterin), CMKLR1, CMKOR1 (RDC1), CNR1, COL18A1, COLIA1, COL4A3, COL6A1, CR2, Cripto, CRP, CSF1 (M-CSF), CSF2 (GM-CSF), CSF3 (GCSF), CTL8, CTNNB1 (b-catenin), CTSB (cathepsin B), CX3CL1 (SCYD1), CX3CR1 (V28), CXCL1 (GRO1), CXCL1O (IP-IO), CXCLI1 (1-TAC/IP-9), CXCL12 (SDF1), CXCL13, CXCL14, CXCL16, CXCL2 (GRO2), CXCL3 (GRO3), CXCL5 (ENA-78/LIX), CXCL6 (GCP-2), CXCL9 (MIG), CXCR3 (GPR9/CKR-L2), CXCR4, CXCR6 (TYM-STR/STRL33/Bonzo), CYB5, CYC1, CYSLTR1, DAB2IP, DES, DKFZp451J0118, DNCL1, DPP4, E2F1, Engel, Edge, Fennel, EFNA3, EFNB2, EGF, EGFR, ELAC2, ENG, Enola, ENO2, ENO3, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, EPHRIN-A1, EPHRIN-A2, EPHRINA3, EPHRIN-A4, EPHRIN-A5, EPHRIN-A6, EPHRIN-B1, EPHRIN-B2, EPHRIN-B3, EPHB4, EPG, ERBB2 (Her-2), EREG, ERK8, Estrogen receptor, Earl, ESR2, F3 (TF), FADD, farnesyl-transferase, FasL, FASNf, FCER1A, FCER2, FCGR3A, FGF, FGF1 (aFGF), FGF10, FGF11, FGF12, FGF12B, FGF13, FGF14, FGF16, FGF17, FGF18, FGF19, FGF2 (bFGF), FGF20, FGF21, FGF22, FGF23, FGF3 (int-2), FGF4 (HST), FGF5, FGF6 (HST-2), FGF7 (KGF), FGF8, FGF9, FGFR3, FIGF (VEGFD), FIL1 (EPSILON), FBL1 (ZETA), FLJ12584, FLJ25530, FLRT1 (fibronectin), FLT1, FLT-3, FOS, FOSL1 (FRA-1), FY (DARC), GABRP (GABAa), GAGEB1, GAGEC1, GALNAC4S-6ST, GATA3, GD2, GDF5, GFI1, GGT1, GM-CSF, GNAS1, GNRH1, GPR2 (CCR10), GPR31, GPR44, GPR81 (FKSG80), GRCC1O (C1O), GRP, GSN (Gelsolin), GSTP1, HAVCR2, HDAC, HDAC4, HDAC5, HDAC7A, HDAC9, Hedgehog, HGF, HIF1A, HIP1, histamine and histamine receptors, HLA-A, HLA-DRA, HLA-E, HM74, HMOXI, HSP90, HUMCYT2A, ICEBERG, ICOSL, ID2, IFN-α, IFNA1, IFNA2, IFNA4, IFNA5, EFNA6, BFNA7, IFNB1, IFNgamma, IFNW1, IGBP1, IGF1, IGFIR, IGF2, IGFBP2, IGFBP3, IGFBP6, DL-1, ILIO, ILIORA, ILIORB, IL-1, IL1R1 (CD121a), IL1R2 (CD121b), IL-IRA, IL-2, IL2RA (CD25), IL2RB (CD122), IL2RG (CD132), IL-4, IL-4R (CD123), IL-5, IL5RA (CD125), IL3RB (CD131), IL-6, IL6RA, (CD126), IR6RB (CD130), IL-7, IL7RA (CD127), IL-8, CXCR1 (IL8RA), CXCR2, (IL8RB/CD128), IL-9, IL9R(CD129), IL-10, IL10RA (CD210), IL10RB (CDW210B), IL-11, IL11RA, IL-12, IL-12A, IL-12B, IL-12RB1, IL-12RB2, IL-13, IL13RA1, IL13RA2, IL14, IL15, IL15RA, IL16, IL17, IL17A, IL17B, IL17C, IL17R, IL18, IL18BP, IL18R1, IL18RAP, IL19, ILIA, ILIB, ILIF10, ILIF5, IL1F6, ILIF7, IL1F8, DL1F9, ILIHYI, ILIR1, IL1R2, ILIRAP, ILIRAPLI, ILIRAPL2, ILIRL1, IL1RL2, ILIRN, IL2, IL20, IL20RA, IL21R, IL22, IL22R, IL22RA2, IL23, DL24, IL25, IL26, IL27, IL28A, IL28B, IL29, IL2RA, IL2RB, IL2RG, IL3, IL30, IL3RA, IL4, 1L4, IL6ST (glycoprotein 130), ILK, INHA, INHBA, INSL3, INSL4, IRAK1, IRAK2, ITGA1, ITGA2, ITGA3, ITGA6 (a6 integrin), ITGAV, ITGB3, ITGB4 (f34 integrin), JAG1, JAK1, JAK3, JTB, JUN, K6HF, KAI1, KDR, KITLG, KLF5 (GC Box BP), KLF6, KLK10, KLK12, KLK13, KLK14, KLK15, KLK3, KLK4, KLK5, KLK6, KLK9, KRT1, KRT19 (Keratin 19), KRT2A, KRTHB6 (hair-specific type II keratin), LAMAS, LEP (leptin), Lingo-p75, Lingo-Troy, LPS, LTA (TNF-b), LTB, LTB4R (GPR16), LTB4R2, LTBR, MACMARCKS, MAG or OMgp, MAP2K7 (c-Jun), MCP-1, MDK, MIB1, midkine, MIF, MISRII, MJP-2, MK, MKI67 (Ki-67), MMP2, MMP9, MS4A1, MSMB, MT3 (metallothionectin-UI), mTOR, MTSS1, MUC1 (mucin), MYC, MYD88, NCK2, neurocan, NFKBI, NFKB2, NGFB (NGF), NGFR, NgR-Lingo, NgRNogo66, (Nogo), NgR-p75, NgR-Troy, NMEI (NM23A), NOTCH, NOTCH1, NOX5, NPPB, NROB1, NROB2, NRID1, NR1D2, NR1H2, NR1H3, NR1H4, NR112, NR113, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRP1, NRP2, NT5E, NTN4, ODZI, OPRDI, P2RX7, PAP, PART1, PATE, PAWR, PCA3, PCDGF, PCNA, PDGFA, PDGFB, PDGFRA, PDGFRB, PECAMI, peg-asparaginase, PF4 (CXCL4), PGF, PGR, phosphacan, PIAS2, PI3 Kinase, PIK3CG, PLAU (uPA), PLG, PLXDCI, PKC, PKC-beta, PPBP (CXCL7), PPID, PR1, PRKCQ, PRKD1, PRL, PROC, PROK2, PSAP, PSCA, PTAFR, PTEN, PTGS2 (COX-2), PTN, RAC2 (P21Rac2), RANK, RANK ligand, RARB, RGS1, RGS13, RGS3, RNFI1O (ZNF144), Ron, ROBO2, RXR, S100A2, SCGB 1D2 (lipophilin B), SCGB2A1 (mammaglobin 2), SCGB2A2 (mammaglobin 1), SCYE1 (endothelial Monocyte-activating cytokine), SDF2, SERPENA1, SERPINA3, SERPINB5 (maspin), SERPINEI (PAM), SERPINFI, SHIP-1, SHIP-2, SHB1, SHB2, SHBG, SIRPα (SHPS1), SfcAZ, SLC2A2, SLC33A1, SLC43A1, SLIT2, SPP1, SPRR1B (Spr1), ST6GAL1, STAB1, STATE, STEAP, STEAP2, TB4R2, TBX21, TCP1O, TDGF1, TEK, TGFA, TGFB1, TGFB1I1, TGFB2, TGFB3, TGFBI, TGFBR1, TGFBR2, TGFBR3, THIL, THBS1 (thrombospondin-1), THBS2, THBS4, THPO, TIE (Tie-1), TIMP3, tissue factor, TLR1, TLR2, TLR3, TLR4, TLR5, TLR6, TLR7, TLR8, TLR9, TLR10, TLR11, TNF, TNF-α, TNFAIP2 (B94), TNFAIP3, TNFRSFI1A, TNFRSF1A, TNFRSF1B, TNFRSF21, TNFRSF5, TNFRSF6 (Fas), TNFRSF7, TNFRSF8, TNFRSF9, TNFSF1O (TRAIL), TNFSF11 (TRANCE), TNFSF12 (APO3L), TNFSF13 (April), TNFSF13B, TNFSF14 (HVEM-L), TNFRSF14 (HVEM), TNFSF15 (VEGI), TNFSF18, TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TOLLIP, Toll-like receptors, TOP2A (topoisomerase Iia), TP53, TPM1, TPM2, TRADD, TRAF1, TRAF2, TRAF3, TRAF4, TRAF5, TRAF6, TRKA, TREM1, TREM2, TRPC6, TSLP, TWEAK, Tyrosinase, uPAR, VEGF, VEGFB, VEGFC, versican, VHL C5, VLA-4, VTCN1 (B7-H4), Wnt-1, XCL1 (lymphotactin), XCL2 (SCM-Ib), XCRI (GPR5/CCXCR1), YY1, ZFPM2, CLEC4C (BDCA-2, DLEC, CD303, CLECSF7), CLEC4D (MCL, CLECSF8), CLEC4E (Mincle), CLEC5A (MDL-1, CLECSF5), CLEC1B (CLEC-2), CLEC9A (DNGR-1), CLEC7A (Dectin-1), PDGFRa, SLAMF7, GP6 (GPVI), LILRA1 (CD85I), LILRA2 (CD85H, ILT1), LILRA4 (CD85G, ILT7), LILRA5 (CD85F, ILT11), LILRA6 (CD85b, ILT8), NCR1 (CD335, LY94, NKp46), NCR3 (CD335, LY94, NKp46), NCR3 (CD337, NKp30), OSCAR, TARM1, CD300C, CD300E, CD300LB (CD300B), CD300LD (CD300D), KIR2DL4 (CD158D), KIR2DS, KLRC2 (CD159C, NKG2C), KLRK1 (CD314, NKG2D), NCR2 (CD336, NKp44), PILRB, SIGLEC1 (CD169, SN), SIGLEC14, SIGLEC15 (CD33L3), SIGLEC16, SIRPB1 (CD172B), TREM1 (CD354), TREM2, TROP2 (tumor-associated calcium signal transducer 2), and KLRF1 (NKp80).

Methods of constructing multivalent binding constructs are known in the art. Bispecific and multispecific antibodies are known in the art. Furthermore, a diabody, triabody, tetrabody, or hexabody can be provided, which is a dimer, trimer, tetramer, or hexamer of polypeptide chains each comprising a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a multimeric molecule having two, three, four, or six functional antigen binding sites. Also, bis-scFv fragments, which are small scFv fragments with two different variable domains can be generated to produce bispecific bis-scFv fragments capable of binding two different epitopes. Fab dimers (Fab2) and Fab trimers (Fab3) can be produced using genetic engineering methods to create multispecific constructs based on Fab fragments.

The Dectin-2 binding agent also can be an antibody conjugate. In this respect, the Dectin-2 binding agent can be a conjugate of (1) an antibody, an alternative scaffold, or fragments thereof, and (2) a protein or non-protein moiety. For example, the Dectin-2 binding agent can be conjugated to a peptide, a fluorescent molecule, chemotherapeutic or other cytotoxic payload, immune-activating or immune-suppressive agent.

The Dectin-2 binding agent can be, or can be obtained from, a human antibody, a non-human antibody, a humanized antibody, or a chimeric antibody, or corresponding antibody fragments. A "chimeric" antibody is an antibody or fragment thereof typically comprising human constant regions and non-human variable regions. A "humanized" antibody is a monoclonal antibody typically comprising a human antibody scaffold but with non-human origin amino acids or sequences in at least one CDR (e.g., 1, 2, 3, 4, 5, or all six CDRs).

Methods for generating such antibodies are known in the art and are described in, for example, Köhler and Milstein, *Eur. J. Immunol.*, 5: 511-519 (1976); Harlow and Lane (eds.), *Antibodies: A Laboratory Manual*, CSH Press (1988); and Janeway et al. (eds.), *Immunobiology*, 9th Ed., Garland Publishing, New York, N.Y. (2017). In certain embodiments, a human or chimeric antibody or antibody fragment can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™ and the Kyowa Kirin KM-MOUSE™ (see, e.g., Lonberg, *Nat. Biotechnol.*, 23(9): 1117-25 (2005), and Lonberg, *Handb. Exp. Pharmacol.*, 181: 69-97 (2008)). A humanized antibody can be generated using any suitable method known in the art (see, e.g., An, Z. (ed.), *Therapeutic Monoclonal Antibodies: From Bench to Clinic*, John Wiley & Sons, Inc., Hoboken, N.J. (2009)), including, e.g., grafting of non-human CDRs onto a human antibody scaffold (see, e.g., Kashmiri et al., *Methods*, 36(1): 25-34 (2005); and Hou et al., *J. Biochem.*, 144(1): 115-120 (2008) and use of phage display (see, e.g., Fellouse, et al., *Journal of Molecular Biology*, 373(4): 924-940 (2007) and Glanville, et al., PNAS, 106(48): 20216-20221 (2009)).

In an embodiment, the Dectin-2 binding agent comprises an immunoglobulin heavy chain variable region of any one of SEQ ID NOs: 243-282 or 324, a sequence that is at least about 90%, at least about 91%, at least about 92%, at least about 93%, at least about 94%, at least about 95%, at least about 96%, at least about 97%, at least about 98%, at least about 99%, or 100% identical to SEQ ID NOs: 243-282 or 324, or at least the CDRs thereof; and/or an immunoglobulin light chain variable region of any one of SEQ ID NOs: 283-322, a sequence that is at least about 90%, at least about 91%, at least about 92%, at least about 93%, at least about 94%, at least about 95%, at least about 96%, at least about 97%, at least about 98%, at least about 99%, or 100% identical to SEQ ID NOs: 283-322, or at least the CDRs thereof.

By way of further illustration, the Dectin-2 binding agent can comprise:

(1) an immunoglobulin heavy chain variable region of SEQ ID NO: 243, or at least the CDRs thereof, and/or an immunoglobulin light chain variable region of SEQ ID NO: 283, or at least the CDRs thereof;

(2) an immunoglobulin heavy chain variable region of SEQ ID NO: 244, or at least the CDRs thereof, and/or an immunoglobulin light chain variable region of SEQ ID NO: 284, or at least the CDRs thereof;

(3) an immunoglobulin heavy chain variable region of SEQ ID NO: 245, or at least the CDRs thereof, and/or an immunoglobulin light chain variable region of SEQ ID NO: 285, or at least the CDRs thereof;

(4) an immunoglobulin heavy chain variable region of SEQ ID NO: 246, or at least the CDRs thereof, and/or an immunoglobulin light chain variable region of SEQ ID NO: 286, or at least the CDRs thereof;

(5) an immunoglobulin heavy chain variable region of SEQ ID NO: 247, or at least the CDRs thereof, and/or an immunoglobulin light chain variable region of SEQ ID NO: 287, or at least the CDRs thereof;

(6) an immunoglobulin heavy chain variable region of SEQ ID NO: 248, or at least the CDRs thereof, and/or an immunoglobulin light chain variable region of SEQ ID NO: 288, or at least the CDRs thereof;

(7) an immunoglobulin heavy chain variable region of SEQ ID NO: 249, or at least the CDRs thereof, and/or an immunoglobulin light chain variable region of SEQ ID NO: 289, or at least the CDRs thereof;

(8) an immunoglobulin heavy chain variable region of SEQ ID NO: 250, or at least the CDRs thereof, and/or an immunoglobulin light chain variable region of SEQ ID NO: 290, or at least the CDRs thereof;

(9) an immunoglobulin heavy chain variable region of SEQ ID NO: 251, or at least the CDRs thereof, and/or an immunoglobulin light chain variable region of SEQ ID NO: 291, or at least the CDRs thereof;

(10) an immunoglobulin heavy chain variable region of SEQ ID NO: 252, or at least the CDRs thereof, and/or an immunoglobulin light chain variable region of SEQ ID NO: 292, or at least the CDRs thereof;

(11) an immunoglobulin heavy chain variable region of SEQ ID NO: 253, or at least the CDRs thereof, and/or an immunoglobulin light chain variable region of SEQ ID NO: 293, or at least the CDRs thereof;

(12) an immunoglobulin heavy chain variable region of SEQ ID NO: 254, or at least the CDRs thereof, and/or an immunoglobulin light chain variable region of SEQ ID NO: 294, or at least the CDRs thereof;

(13) an immunoglobulin heavy chain variable region of SEQ ID NO: 255, or at least the CDRs thereof, and/or an immunoglobulin light chain variable region of SEQ ID NO: 295, or at least the CDRs thereof;

(14) an immunoglobulin heavy chain variable region of SEQ ID NO: 256, or at least the CDRs thereof, and/or an immunoglobulin light chain variable region of SEQ ID NO: 296, or at least the CDRs thereof;

(15) an immunoglobulin heavy chain variable region of SEQ ID NO: 257, or at least the CDRs thereof, and/or an immunoglobulin light chain variable region of SEQ ID NO: 297, or at least the CDRs thereof;

(16) an immunoglobulin heavy chain variable region of SEQ ID NO: 258, or at least the CDRs thereof, and/or an immunoglobulin light chain variable region of SEQ ID NO: 298, or at least the CDRs thereof;

(17) an immunoglobulin heavy chain variable region of SEQ ID NO: 259, or at least the CDRs thereof, and/or an immunoglobulin light chain variable region of SEQ ID NO: 299, or at least the CDRs thereof;

(18) an immunoglobulin heavy chain variable region of SEQ ID NO: 256, or at least the CDRs thereof, and/or an immunoglobulin light chain variable region of SEQ ID NO: 300, or at least the CDRs thereof;

(19) an immunoglobulin heavy chain variable region of SEQ ID NO: 260, or at least the CDRs thereof, and/or an immunoglobulin light chain variable region of SEQ ID NO: 301, or at least the CDRs thereof;

(20) an immunoglobulin heavy chain variable region of SEQ ID NO: 261, or at least the CDRs thereof, and/or an immunoglobulin light chain variable region of SEQ ID NO: 302, or at least the CDRs thereof;

(21) an immunoglobulin heavy chain variable region of SEQ ID NO: 262, or at least the CDRs thereof, and/or an immunoglobulin light chain variable region of SEQ ID NO: 303, or at least the CDRs thereof;

(22) an immunoglobulin heavy chain variable region of SEQ ID NO: 263, or at least the CDRs thereof, and/or an immunoglobulin light chain variable region of SEQ ID NO: 304, or at least the CDRs thereof;

(23) an immunoglobulin heavy chain variable region of SEQ ID NO: 264, or at least the CDRs thereof, and/or an immunoglobulin light chain variable region of SEQ ID NO: 305, or at least the CDRs thereof;

(23a) an immunoglobulin heavy chain variable region of SEQ ID NO: 265, or at least the CDRs thereof, and/or an immunoglobulin light chain variable region of SEQ ID NO: 305, or at least the CDRs thereof;

(23b) an immunoglobulin heavy chain variable region of SEQ ID NO: 324, or at least the CDRs thereof, and/or an immunoglobulin light chain variable region of SEQ ID NO: 305, or at least the CDRs thereof;

(24) an immunoglobulin heavy chain variable region of SEQ ID NO: 266, or at least the CDRs thereof, and/or an immunoglobulin light chain variable region of SEQ ID NO: 306, or at least the CDRs thereof;

(25) an immunoglobulin heavy chain variable region of SEQ ID NO: 267, or at least the CDRs thereof, and/or an immunoglobulin light chain variable region of SEQ ID NO: 307, or at least the CDRs thereof;

(26) an immunoglobulin heavy chain variable region of SEQ ID NO: 268, or at least the CDRs thereof, and/or an immunoglobulin light chain variable region of SEQ ID NO: 308, or at least the CDRs thereof;

(27) an immunoglobulin heavy chain variable region of SEQ ID NO: 269, or at least the CDRs thereof, and/or an immunoglobulin light chain variable region of SEQ ID NO: 309, or at least the CDRs thereof;

(28) an immunoglobulin heavy chain variable region of SEQ ID NO: 270, or at least the CDRs thereof, and/or an immunoglobulin light chain variable region of SEQ ID NO: 310, or at least the CDRs thereof;

(29) an immunoglobulin heavy chain variable region of SEQ ID NO: 271, or at least the CDRs thereof, and/or an immunoglobulin light chain variable region of SEQ ID NO: 311, or at least the CDRs thereof;

(30) an immunoglobulin heavy chain variable region of SEQ ID NO: 272, or at least the CDRs thereof, and/or an immunoglobulin light chain variable region of SEQ ID NO: 312, or at least the CDRs thereof;

(31) an immunoglobulin heavy chain variable region of SEQ ID NO: 273, or at least the CDRs thereof, and/or an immunoglobulin light chain variable region of SEQ ID NO: 313, or at least the CDRs thereof;

(32) an immunoglobulin heavy chain variable region of SEQ ID NO: 274, or at least the CDRs thereof, and/or an immunoglobulin light chain variable region of SEQ ID NO: 314, or at least the CDRs thereof;

(33) an immunoglobulin heavy chain variable region of SEQ ID NO: 275, or at least the CDRs thereof, and/or an immunoglobulin light chain variable region of SEQ ID NO: 315, or at least the CDRs thereof;

(34) an immunoglobulin heavy chain variable region of SEQ ID NO: 276, or at least the CDRs thereof, and/or an immunoglobulin light chain variable region of SEQ ID NO: 316, or at least the CDRs thereof;

(35) an immunoglobulin heavy chain variable region of SEQ ID NO: 277, or at least the CDRs thereof, and/or an immunoglobulin light chain variable region of SEQ ID NO: 317, or at least the CDRs thereof;

(36) an immunoglobulin heavy chain variable region of SEQ ID NO: 278, or at least the CDRs thereof, and/or an immunoglobulin light chain variable region of SEQ ID NO: 318, or at least the CDRs thereof;

(37) an immunoglobulin heavy chain variable region of SEQ ID NO: 279, or at least the CDRs thereof, and/or an immunoglobulin light chain variable region of SEQ ID NO: 319, or at least the CDRs thereof;

(38) an immunoglobulin heavy chain variable region of SEQ ID NO: 280, or at least the CDRs thereof, and/or an immunoglobulin light chain variable region of SEQ ID NO: 320, or at least the CDRs thereof;

(39) an immunoglobulin heavy chain variable region of SEQ ID NO: 281, or at least the CDRs thereof, and/or an immunoglobulin light chain variable region of SEQ ID NO: 321, or at least the CDRs thereof;

(40) an immunoglobulin heavy chain variable region of SEQ ID NO: 282, or at least the CDRs thereof, and/or an immunoglobulin light chain variable region of SEQ ID NO: 322, or at least the CDRs thereof;

(41) an immunoglobulin heavy chain variable region of Table 4 and/or an immunoglobulin light chain variable region of Table 5, or at least the CDRs thereof; and/or

(42) an immunoglobulin heavy chain of Table 7 and/or an immunoglobulin light chain of Table 6.

The CDRs of a given heavy or light chain Ig sequence can be determined in accordance with any of the various known Ig numbering schemes, such as Kabat, Chothia, Martin (Enhanced Chothia), IGMT, AbM or AHo (see, e.g., Kabat, et al., *Sequences of Proteins of Immunological Interest*, U.S. Department of Health and Human Services, NIH (1991); Chothia, et al., *Canonical Structures for the Hypervariable Regions of Immunoglobulins*, J. Mol. Biol., 196:901-917 (1987); Al-Lazikani et al., *Standard Conformations for the Canonical Structures of Immunoglobulins*, J. Mol. Biol., 273:927-948 (1997); Abhinandan et al., *Analysis and Improvements to Kabat and Structurally Correct Numbering of Antibody Variable Domains*, Mol. Immunol., 45: 3832-3839 (2008); Lefranc et al., *The IMGT unique numbering for immunoglobulins, T cell Receptors and Ig-like domains*, The Immunologist, 7: 132-136 (1999); Lefranc et al., *IMGT unique numbering for immunoglobulin and T cell receptor variable domains and I superfamily V-like domains*, Dev. Comp. Immunol., 27: 55-77 (2003); and Honegger et al., *Yet another numbering scheme for immunoglobulin variable domains: an automatic modeling and analysis tool*, J. Mol. Biol. 309: 657-670 (2001). In particular embodiments, Kabat is used to determine the CDRs of a given heavy or light chain Ig sequence. In certain embodiments, the Dectin-2 binding agent comprises one or more of the following CDRs:

a HCDR1 comprising or consisting of any one of SEQ ID NOs: 1-30 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 1-30;

a HCDR2 comprising or consisting of any one of SEQ ID NOs: 31-64 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 31-64; and a HCDR3 comprising or consisting of any one of SEQ ID NOs: 65-103 or 323 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 65-103 or 323; and/or the immunoglobulin light chain polypeptide comprises a LCDR1 comprising or consisting of any one of SEQ ID NOs: 104-125 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 104-125;

a LCDR2 comprising or consisting of any one of SEQ ID NOs: 126-148 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 126-148; and a LCDR3 comprising or consisting of any one of SEQ ID NOs: 149-181 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 149-181.

In particular embodiments, the binding agent comprises an immunoglobulin heavy chain polypeptide and an immunoglobulin light chain polypeptide, wherein:

(1) the immunoglobulin heavy chain polypeptide comprises a HCDR1 comprising or consisting of SEQ ID NO: 1, a HCDR2 comprising or consisting of SEQ ID NO: 31, and a HCDR3 comprising or consisting of SEQ ID NO: 65; and/or the immunoglobulin light chain polypeptide comprises a LCDR1 comprising or consisting of SEQ ID NO: 104, a LCDR2 comprising or consisting of SEQ ID NO: 126, and a LCDR3 comprising or consisting of SEQ ID NO: 149;

(2) the immunoglobulin heavy chain polypeptide comprises a HCDR1 comprising or consisting of SEQ ID NO: 2, a HCDR2 comprising or consisting of SEQ ID NO: 32, and a HCDR3 comprising or consisting of SEQ ID NO: 66; and/or the immunoglobulin light chain polypeptide comprises a LCDR1 comprising or consisting of SEQ ID NO: 105, a LCDR2 comprising or consisting of SEQ ID NO: 127, and a LCDR3 comprising or consisting of SEQ ID NO: 150;

(3) the immunoglobulin heavy chain polypeptide comprises a HCDR1 comprising or consisting of SEQ ID NO: 3, a HCDR2 comprising or consisting of SEQ ID NO: 33, and a HCDR3 comprising or consisting of SEQ ID NO: 67; and/or the immunoglobulin light chain polypeptide comprises a LCDR1 comprising or consisting of SEQ ID NO: 106, a LCDR2 comprising or consisting of SEQ ID NO: 126, and a LCDR3 comprising or consisting of SEQ ID NO: 151;

(4) the immunoglobulin heavy chain polypeptide comprises a HCDR1 comprising or consisting of SEQ ID NO: 4, a HCDR2 comprising or consisting of SEQ ID NO: 34, and a HCDR3 comprising or consisting of SEQ ID NO: 68; and/or the immunoglobulin light chain polypeptide comprises a LCDR1 comprising or consisting of SEQ ID NO: 107, a LCDR2 comprising or consisting of SEQ ID NO: 127, and a LCDR3 comprising or consisting of SEQ ID NO: 150;

(5) the immunoglobulin heavy chain polypeptide comprises a HCDR1 comprising or consisting of SEQ ID NO: 5, a HCDR2 comprising or consisting of SEQ ID NO: 35, and a HCDR3 comprising or consisting of SEQ ID NO: 69; and/or the immunoglobulin light chain polypeptide comprises a LCDR1 comprising or consisting of SEQ ID NO: 108, a LCDR2 comprising or consisting of SEQ ID NO: 127, and a LCDR3 comprising or consisting of SEQ ID NO: 152;

(6) the immunoglobulin heavy chain polypeptide comprises a HCDR1 comprising or consisting of SEQ ID NO: 6, a HCDR2 comprising or consisting of SEQ ID NO: 36, and a HCDR3 comprising or consisting of SEQ ID NO: 70; and/or the immunoglobulin light chain polypeptide comprises a LCDR1 comprising or consisting of SEQ ID NO: 104, a LCDR2 comprising or consisting of SEQ ID NO: 128, and a LCDR3 comprising or consisting of SEQ ID NO: 153;

(7) the immunoglobulin heavy chain polypeptide comprises a HCDR1 comprising or consisting of SEQ ID NO: 6, a HCDR2 comprising or consisting of SEQ ID NO: 37, and a HCDR3 comprising or consisting of SEQ ID NO: 71; and/or the immunoglobulin light chain polypeptide comprises a LCDR1 comprising or consisting of SEQ ID NO: 104, a LCDR2 comprising or consisting of SEQ ID NO: 129, and a LCDR3 comprising or consisting of SEQ ID NO: 154;

(8) the immunoglobulin heavy chain polypeptide comprises a HCDR1 comprising or consisting of SEQ ID NO: 7, a HCDR2 comprising or consisting of SEQ ID NO: 38, and a HCDR3 comprising or consisting of SEQ ID NO: 72; and/or the immunoglobulin light chain polypeptide comprises a LCDR1 comprising or consisting of SEQ ID NO: 109, a LCDR2 comprising or consisting of SEQ ID NO: 127, and a LCDR3 comprising or consisting of SEQ ID NO: 155;

(9) the immunoglobulin heavy chain polypeptide comprises a HCDR1 comprising or consisting of SEQ ID NO: 8, a HCDR2 comprising or consisting of SEQ ID NO: 39, and a HCDR3 comprising or consisting of SEQ ID NO: 73; and/or the immunoglobulin light chain polypeptide comprises a LCDR1 comprising or consisting of SEQ ID NO: 110, a LCDR2 comprising or consisting of SEQ ID NO: 126, and a LCDR3 comprising or consisting of SEQ ID NO: 150;

(10) the immunoglobulin heavy chain polypeptide comprises a HCDR1 comprising or consisting of SEQ ID NO: 9, a HCDR2 comprising or consisting of SEQ ID NO: 40, and a HCDR3 comprising or consisting of SEQ ID NO: 74; and/or the immunoglobulin light chain polypeptide comprises a LCDR1 comprising or consisting of SEQ ID NO: 104, a LCDR2 comprising or consisting of SEQ ID NO: 130, and a LCDR3 comprising or consisting of SEQ ID NO: 156;

(11) the immunoglobulin heavy chain polypeptide comprises a HCDR1 comprising or consisting of SEQ ID NO: 10, a HCDR2 comprising or consisting of SEQ ID NO: 41, and a HCDR3 comprising or consisting of SEQ ID NO: 75; and/or the immunoglobulin light chain polypeptide comprises a LCDR1 comprising or consisting of SEQ ID NO: 110, a LCDR2 comprising or consisting of SEQ ID NO: 131, and a LCDR3 comprising or consisting of SEQ ID NO: 157;

(12) the immunoglobulin heavy chain polypeptide comprises a HCDR1 comprising or consisting of SEQ ID NO: 11, a HCDR2 comprising or consisting of SEQ ID NO: 42, and a HCDR3 comprising or consisting of SEQ ID NO: 76; and/or the immunoglobulin light chain polypeptide comprises a LCDR1 comprising or consisting of SEQ ID NO: 111, a LCDR2 comprising or consisting of SEQ ID NO: 132, and a LCDR3 comprising or consisting of SEQ ID NO: 158;

(13) the immunoglobulin heavy chain polypeptide comprises a HCDR1 comprising or consisting of SEQ ID NO: 12, a HCDR2 comprising or consisting of SEQ ID NO: 43, and a HCDR3 comprising or consisting of SEQ ID NO: 77; and/or the immunoglobulin light chain polypeptide comprises a LCDR1 comprising or consisting of SEQ ID NO: 104, a LCDR2 comprising or consisting of SEQ ID NO: 133, and a LCDR3 comprising or consisting of SEQ ID NO: 159;

(14) the immunoglobulin heavy chain polypeptide comprises a HCDR1 comprising or consisting of SEQ ID NO: 13, a HCDR2 comprising or consisting of SEQ ID NO: 44, and a HCDR3 comprising or consisting of SEQ ID NO: 78; and/or the immunoglobulin light chain polypeptide comprises a LCDR1 comprising or consisting of SEQ ID NO: 112, a LCDR2 comprising or consisting of SEQ ID NO: 127, and a LCDR3 comprising or consisting of SEQ ID NO: 160;

(15) the immunoglobulin heavy chain polypeptide comprises a HCDR1 comprising or consisting of SEQ ID NO: 14, a HCDR2 comprising or consisting of SEQ ID NO: 45, and a HCDR3 comprising or consisting of SEQ ID NO: 79; and/or the immunoglobulin light chain polypeptide comprises a LCDR1 comprising or consisting of SEQ ID NO: 113, a LCDR2 comprising or consisting of SEQ ID NO: 134, and a LCDR3 comprising or consisting of SEQ ID NO: 161;

(16) the immunoglobulin heavy chain polypeptide comprises a HCDR1 comprising or consisting of SEQ ID NO: 15, a HCDR2 comprising or consisting of SEQ ID NO: 46, and a HCDR3 comprising or consisting of SEQ ID NO: 80; and/or the immunoglobulin light chain polypeptide comprises a LCDR1 comprising or consisting of SEQ ID NO: 114, a LCDR2 comprising or consisting of SEQ ID NO: 135, and a LCDR3 comprising or consisting of SEQ ID NO: 162;

(17) the immunoglobulin heavy chain polypeptide comprises a HCDR1 comprising or consisting of SEQ ID NO: 16, a HCDR2 comprising or consisting of SEQ ID NO: 47, and a HCDR3 comprising or consisting of SEQ ID NO: 81; and/or the immunoglobulin light chain polypeptide comprises a LCDR1 comprising or consisting of SEQ ID NO: 115, a LCDR2 comprising or consisting of SEQ ID NO: 136, and a LCDR3 comprising or consisting of SEQ ID NO: 163;

(18) the immunoglobulin heavy chain polypeptide comprises a HCDR1 comprising or consisting of SEQ ID NO: 13, a HCDR2 comprising or consisting of SEQ ID NO: 44, and a HCDR3 comprising or consisting of SEQ ID NO: 78; and/or the immunoglobulin light chain polypeptide comprises a LCDR1 comprising or consisting of SEQ ID NO: 112, a LCDR2 comprising or consisting of SEQ ID NO: 127, and a LCDR3 comprising or consisting of SEQ ID NO: 160;

(19) the immunoglobulin heavy chain polypeptide comprises a HCDR1 comprising or consisting of SEQ ID NO: 17, a HCDR2 comprising or consisting of SEQ ID NO: 48, and a HCDR3 comprising or consisting of SEQ ID NO: 82; and/or the immunoglobulin light chain polypeptide comprises a LCDR1 comprising or consisting of SEQ ID NO: 116, a LCDR2 comprising or consisting of SEQ ID NO: 137, and a LCDR3 comprising or consisting of SEQ ID NO: 164;

(20) the immunoglobulin heavy chain polypeptide comprises a HCDR1 comprising or consisting of SEQ ID NO: 18, a HCDR2 comprising or consisting of SEQ ID NO: 49, and a HCDR3 comprising or consisting of SEQ ID NO: 83; and/or the immunoglobulin light chain polypeptide comprises a LCDR1 comprising or consisting of SEQ ID NO: 117, a LCDR2 comprising or consisting of SEQ ID NO: 138, and a LCDR3 comprising or consisting of SEQ ID NO: 150;

(21) the immunoglobulin heavy chain polypeptide comprises a HCDR1 comprising or consisting of SEQ ID NO: 19, a HCDR2 comprising or consisting of SEQ ID NO: 50, and a HCDR3 comprising or consisting of SEQ ID NO: 84; and/or the immunoglobulin light chain polypeptide comprises a LCDR1 comprising or consisting of SEQ ID NO: 118, a LCDR2 comprising or consisting of SEQ ID NO: 139, and a LCDR3 comprising or consisting of SEQ ID NO: 150;

(22) the immunoglobulin heavy chain polypeptide comprises a HCDR1 comprising or consisting of SEQ ID NO: 20, a HCDR2 comprising or consisting of SEQ ID NO: 51, and a HCDR3 comprising or consisting of SEQ ID NO: 85; and/or the immunoglobulin light chain polypeptide comprises a LCDR1 comprising or consisting of SEQ ID NO: 116, a LCDR2 comprising or consisting of SEQ ID NO: 126, and a LCDR3 comprising or consisting of SEQ ID NO: 165;

(23) the immunoglobulin heavy chain polypeptide comprises a HCDR1 comprising or consisting of SEQ ID NO: 21, a HCDR2 comprising or consisting of SEQ ID NO: 52, and a HCDR3 comprising or consisting of SEQ ID NO: 86; and/or the immunoglobulin light chain polypeptide comprises a LCDR1 comprising or consisting of SEQ ID NO: 110, a LCDR2 comprising or consisting of SEQ ID NO: 140, and a LCDR3 comprising or consisting of SEQ ID NO: 166;

(23a) the immunoglobulin heavy chain polypeptide comprises a HCDR1 comprising or consisting of SEQ ID NO: 21, a HCDR2 comprising or consisting of SEQ ID NO: 52, and a HCDR3 comprising or consisting of SEQ ID NO: 86; and/or the immunoglobulin light chain polypeptide comprises a LCDR1 comprising or consisting of SEQ ID NO: 110, a LCDR2 comprising or consisting of SEQ ID NO: 140, and a LCDR3 comprising or consisting of SEQ ID NO: 166;

(23b) immunoglobulin heavy chain polypeptide comprises a HCDR1 comprising or consisting of SEQ ID NO: 21, a HCDR2 comprising or consisting of SEQ ID NO: 52, and a HCDR3 comprising or consisting of SEQ ID NO: 323; and/or the immunoglobulin light chain polypeptide comprises a LCDR1 comprising or consisting of SEQ ID NO: 110, a LCDR2 comprising or consisting of SEQ ID NO: 140, and a LCDR3 comprising or consisting of SEQ ID NO: 166;

(24) the immunoglobulin heavy chain polypeptide comprises a HCDR1 comprising or consisting of SEQ ID NO: 6, a HCDR2 comprising or consisting of SEQ ID NO: 53, and a HCDR3 comprising or consisting of SEQ ID NO: 87; and/or the immunoglobulin light chain polypeptide comprises a LCDR1 comprising or consisting of SEQ ID NO: 104, a LCDR2 comprising or consisting of SEQ ID NO: 141, and a LCDR3 comprising or consisting of SEQ ID NO: 167;

(25) the immunoglobulin heavy chain polypeptide comprises a HCDR1 comprising or consisting of SEQ ID NO: 22, a HCDR2 comprising or consisting of SEQ ID NO: 38, and a HCDR3 comprising or consisting of SEQ ID NO: 88; and/or the immunoglobulin light chain polypeptide comprises a LCDR1 comprising or consisting of SEQ ID NO: 119, a LCDR2 comprising or consisting of SEQ ID NO: 126, and a LCDR3 comprising or consisting of SEQ ID NO: 168;

(26) the immunoglobulin heavy chain polypeptide comprises a HCDR1 comprising or consisting of SEQ ID NO: 6, a HCDR2 comprising or consisting of SEQ ID NO: 37, and a HCDR3 comprising or consisting of SEQ ID NO: 89; and/or the immunoglobulin light chain polypeptide comprises a LCDR1 comprising or consisting of SEQ ID NO: 120, a LCDR2 comprising or consisting of SEQ ID NO: 142, and a LCDR3 comprising or consisting of SEQ ID NO: 169;

(27) the immunoglobulin heavy chain polypeptide comprises a HCDR1 comprising or consisting of SEQ ID NO: 23, a HCDR2 comprising or consisting of SEQ ID NO: 54, and a HCDR3 comprising or consisting of SEQ ID NO: 90; and/or the immunoglobulin light chain polypeptide comprises a LCDR1 comprising or consisting of SEQ ID NO: 121, a LCDR2 comprising or consisting of SEQ ID NO: 143, and a LCDR3 comprising or consisting of SEQ ID NO: 170;

(28) the immunoglobulin heavy chain polypeptide comprises a HCDR1 comprising or consisting of SEQ ID NO: 6, a HCDR2 comprising or consisting of SEQ ID NO: 55, and a HCDR3 comprising or consisting of SEQ ID NO: 91; and/or the immunoglobulin light chain polypeptide comprises a LCDR1 comprising or consisting of SEQ ID NO: 122, a LCDR2 comprising or consisting of SEQ ID NO: 126, and a LCDR3 comprising or consisting of SEQ ID NO: 171;

(29) the immunoglobulin heavy chain polypeptide comprises a HCDR1 comprising or consisting of SEQ ID NO: 19, a HCDR2 comprising or consisting of SEQ ID NO: 56, and a HCDR3 comprising or consisting of SEQ ID NO: 92; and/or the immunoglobulin light chain polypeptide comprises a LCDR1 comprising or consisting of SEQ ID NO: 123, a LCDR2 comprising or consisting of SEQ ID NO: 127, and a LCDR3 comprising or consisting of SEQ ID NO: 172;

(30) the immunoglobulin heavy chain polypeptide comprises a HCDR1 comprising or consisting of SEQ ID NO: 11, a HCDR2 comprising or consisting of SEQ ID NO: 57, and a HCDR3 comprising or consisting of SEQ ID NO: 93; and/or the immunoglobulin light chain polypeptide comprises a LCDR1 comprising or consisting of SEQ ID NO: 109, a LCDR2 comprising or consisting of SEQ ID NO: 144, and a LCDR3 comprising or consisting of SEQ ID NO: 173;

(31) the immunoglobulin heavy chain polypeptide comprises a HCDR1 comprising or consisting of SEQ ID NO: 4, a HCDR2 comprising or consisting of SEQ ID NO: 58, and a HCDR3 comprising or consisting of SEQ ID NO: 94; and/or the immunoglobulin light chain polypeptide comprises a LCDR1 comprising or consisting of SEQ ID NO: 104, a LCDR2 comprising or consisting of SEQ ID NO: 136, and a LCDR3 comprising or consisting of SEQ ID NO: 174;

(32) the immunoglobulin heavy chain polypeptide comprises a HCDR1 comprising or consisting of SEQ ID NO: 24, a HCDR2 comprising or consisting of SEQ ID NO: 59, and a HCDR3 comprising or consisting of SEQ ID NO: 95; and/or the immunoglobulin light chain polypeptide comprises a LCDR1 comprising or consisting of SEQ ID NO: 110, a LCDR2 comprising or consisting of SEQ ID NO: 127, and a LCDR3 comprising or consisting of SEQ ID NO: 153;

(33) the immunoglobulin heavy chain polypeptide comprises a HCDR1 comprising or consisting of SEQ ID NO: 11, a HCDR2 comprising or consisting of SEQ ID NO: 60, and a HCDR3 comprising or consisting of SEQ ID NO: 96; and/or the immunoglobulin light chain polypeptide comprises a LCDR1 comprising or consisting of SEQ ID NO: 111, a LCDR2 comprising or consisting of SEQ ID NO: 145, and a LCDR3 comprising or consisting of SEQ ID NO: 175;

(34) the immunoglobulin heavy chain polypeptide comprises a HCDR1 comprising or consisting of SEQ ID NO: 25, a HCDR2 comprising or consisting of SEQ ID NO: 61, and a HCDR3 comprising or consisting of SEQ ID NO: 97; and/or the immunoglobulin light chain polypeptide comprises a LCDR1 comprising or consisting of SEQ ID NO: 111, a LCDR2 comprising or consisting of SEQ ID NO: 146, and a LCDR3 comprising or consisting of SEQ ID NO: 176;

(35) the immunoglobulin heavy chain polypeptide comprises a HCDR1 comprising or consisting of SEQ ID NO: 26, a HCDR2 comprising or consisting of SEQ ID NO: 59, and a HCDR3 comprising or consisting of SEQ ID NO: 98; and/or the immunoglobulin light chain polypeptide comprises a LCDR1 comprising or consisting of SEQ ID NO: 110, a LCDR2 comprising or consisting of SEQ ID NO: 126, and a LCDR3 comprising or consisting of SEQ ID NO: 177;

(36) the immunoglobulin heavy chain polypeptide comprises a HCDR1 comprising or consisting of SEQ ID NO: 25, a HCDR2 comprising or consisting of SEQ ID NO: 38, and a HCDR3 comprising or consisting of SEQ ID NO: 99; and/or the immunoglobulin light chain polypeptide comprises a LCDR1 comprising or consisting of SEQ ID NO: 124, a LCDR2 comprising or consisting of SEQ ID NO: 126, and a LCDR3 comprising or consisting of SEQ ID NO: 178;

(37) the immunoglobulin heavy chain polypeptide comprises a HCDR1 comprising or consisting of SEQ ID NO: 27, a HCDR2 comprising or consisting of SEQ ID NO: 62, and a HCDR3 comprising or consisting of SEQ ID NO: 100; and/or the immunoglobulin light chain polypeptide comprises a LCDR1 comprising or consisting of SEQ ID NO: 111, a LCDR2 comprising or consisting of SEQ ID NO: 147, and a LCDR3 comprising or consisting of SEQ ID NO: 179;

(38) the immunoglobulin heavy chain polypeptide comprises a HCDR1 comprising or consisting of SEQ ID NO: 28, a HCDR2 comprising or consisting of SEQ ID NO: 63, and a HCDR3 comprising or consisting of SEQ ID NO: 101; and/or the immunoglobulin light chain polypeptide comprises a LCDR1 comprising or consisting of SEQ ID NO: 116, a LCDR2 comprising or consisting of SEQ ID NO: 148, and a LCDR3 comprising or consisting of SEQ ID NO: 180;

(39) the immunoglobulin heavy chain polypeptide comprises a HCDR1 comprising or consisting of SEQ ID NO: 29, a HCDR2 comprising or consisting of SEQ ID NO: 64, and a HCDR3 comprising or consisting of SEQ ID NO: 102; and/or the immunoglobulin light chain polypeptide comprises a LCDR1 comprising or consisting of SEQ ID NO: 121, a LCDR2 comprising or consisting of SEQ ID NO: 126, and a LCDR3 comprising or consisting of SEQ ID NO: 177;

(40) the immunoglobulin heavy chain polypeptide comprises a HCDR1 comprising or consisting of SEQ ID NO: 30, a HCDR2 comprising or consisting of SEQ ID NO: 38, and a HCDR3 comprising or consisting of SEQ ID NO: 103; and/or the immunoglobulin light chain polypeptide comprises a LCDR1 comprising or consisting of SEQ ID NO: 125, a LCDR2 comprising or consisting of SEQ ID NO: 127, and a LCDR3 comprising or consisting of SEQ ID NO: 181;

(41) the immunoglobulin heavy chain polypeptide and immunoglobulin light chain polypeptide comprises any combination of the CDRs listed in Table 1;

(42) the immunoglobulin heavy chain polypeptide comprising or consisting of any one of SEQ ID NOs: 328-345 and immunoglobulin light chain polypeptide comprising or consisting of any one of SEQ ID NOs: 325-327;

(43) the immunoglobulin heavy chain polypeptide comprising or consisting of SEQ ID NO: 328 and immunoglobulin light chain polypeptide comprising or consisting of SEQ ID NO: 325;

(44) the immunoglobulin heavy chain polypeptide comprising or consisting of SEQ ID NO: 329 and immunoglobulin light chain polypeptide comprising or consisting of SEQ ID NO: 325;

(45) the immunoglobulin heavy chain polypeptide comprising or consisting of SEQ ID NO: 330 and light chain polypeptide comprising or consisting of SEQ ID NO: 325;

(46) the immunoglobulin heavy chain polypeptide comprising or consisting of SEQ ID NO: 331 and immunoglobulin light chain polypeptide comprising or consisting of SEQ ID NO: 325;

(47) the immunoglobulin heavy chain polypeptide comprising or consisting of SEQ ID NO: 332 and immunoglobulin light chain polypeptide comprising or consisting of SEQ ID NO: 325;

(48) the immunoglobulin heavy chain polypeptide comprising or consisting of SEQ ID NO: 333 and immunoglobulin light chain polypeptide comprising or consisting of SEQ ID NO: 325;

(49) the immunoglobulin heavy chain polypeptide comprising or consisting of SEQ ID NO: 334 and immunoglobulin light chain polypeptide comprising or consisting of SEQ ID NO: 3;

(50) the immunoglobulin heavy chain polypeptide comprising or consisting of SEQ ID NO: 335 and immunoglobulin light chain polypeptide comprising or consisting of SEQ ID NO: 326;

(51) the immunoglobulin heavy chain polypeptide comprising or consisting of SEQ ID NO: 336 and light chain polypeptide comprising or consisting of SEQ ID NO: 326;

(52) the immunoglobulin heavy chain polypeptide comprising or consisting of SEQ ID NO: 337 and immunoglobulin light chain polypeptide comprising or consisting of SEQ ID NO: 326;
(53) the immunoglobulin heavy chain polypeptide comprising or consisting of SEQ ID NO: 338 and immunoglobulin light chain polypeptide comprising or consisting of SEQ ID NO: 326;
(54) the immunoglobulin heavy chain polypeptide comprising or consisting of SEQ ID NO: 339 and immunoglobulin light chain polypeptide comprising or consisting of SEQ ID NO: 326;
(55) the immunoglobulin heavy chain polypeptide comprising or consisting of SEQ ID NO: 340 and immunoglobulin light chain polypeptide comprising or consisting of SEQ ID NO: 327;
(56) the immunoglobulin heavy chain polypeptide comprising or consisting of SEQ ID NO: 341 and immunoglobulin light chain polypeptide comprising or consisting of SEQ ID NO: 327;
(57) the immunoglobulin heavy chain polypeptide comprising or consisting of SEQ ID NO: 342 and immunoglobulin light chain polypeptide comprising or consisting of SEQ ID NO: 327;
(58) the immunoglobulin heavy chain polypeptide comprising or consisting of SEQ ID NO: 343 and immunoglobulin light chain polypeptide comprising or consisting of SEQ ID NO: 327;
(59) the immunoglobulin heavy chain polypeptide comprising or consisting of SEQ ID NO: 344 and immunoglobulin light chain polypeptide comprising or consisting of SEQ ID NO: 327; and/or
(55) the immunoglobulin heavy chain polypeptide comprising or consisting of SEQ ID NO: 345 and immunoglobulin light chain polypeptide comprising or consisting of SEQ ID NO: 327.

In particular embodiments, the binding agent comprises an immunoglobulin heavy chain polypeptide and an immunoglobulin light chain polypeptide, wherein the immunoglobulin heavy chain polypeptide comprises a first framework region, a second framework region, a third framework region, and/or a fourth framework region; and/or the immunoglobulin light chain polypeptide comprises a first framework region, a second framework region, a third framework region, and/or a fourth framework region; and/or the immunoglobulin heavy chain polypeptide and light chain polypeptide comprises any combination of the framework regions listed in Tables 2 and 3.

TABLE 1

| Binding Agent | SEQ ID | HCDR1 | SEQ ID | HCDR2 | SEQ ID | HCDR3 | SEQ ID | LCDR1 | SEQ ID | LCDR2 | SEQ ID | LCDR3 |
|---|---|---|---|---|---|---|---|---|---|---|---|---|
| 1 | 1 | SYYMQ | 31 | WINPKSGGTNYAQKFQG | 65 | GTYLRTGSSLSGYYYGMDV | 104 | QASQDISNYLN | 126 | AASSLQS | 149 | QQTDSIPIT |
| 2 | 2 | TYYMH | 32 | IINPSGGSTSYAQKFQG | 66 | SHYGDLNGGFDL | 105 | RASQYISSYLA | 127 | AASTLQS | 150 | QQSYSTPLT |
| 3 | 3 | NFGIN | 33 | WINPNSGGANYAQKFQG | 67 | GVVAARYYYMDV | 106 | RASQNIGSYLN | 126 | AASSLQS | 151 | QQTNSFPLT |
| 4 | 4 | SYDIN | 34 | WINPNSGATNSAQKFQG | 68 | AGYSSSWDGYYYYGMDV | 107 | RASQSISSHLN | 127 | AASTLQS | 150 | QQSYSTPLT |
| 5 | 5 | GYYVH | 35 | IIHPNGGSTSYAQKFQG | 69 | DQAGTGGHGMDV | 108 | RASQSINNWLA | 127 | AASTLQS | 152 | EQNYRLPIT |
| 6 | 6 | SYWMS | 36 | DISGSGRSTYYADSVKG | 70 | GRYLEWVLSSEDYYFGMDV | 104 | QASQDISNYLN | 128 | AASSLHP | 153 | QQSDSFPLT |
| 7 | 6 | SYWMS | 37 | AISGSGGSTYYADSVKG | 71 | GRYSRSWERWYFDL | 104 | QASQDISNYLN | 129 | AASNLES | 154 | QQTNSFPIT |
| 8 | 7 | SQYMH | 38 | WMNPNSGNTGYAQKFQG | 72 | GQYDSSGYYYFDY | 109 | QASQDIRNYLN | 127 | AASTLQS | 155 | QQSYSFPLT |
| 9 | 8 | TYYMN | 39 | ILSPSGGGTSYAPKFQG | 73 | ATYYDFWSGSLDY | 110 | RASQSISSYLN | 126 | AASSLQS | 150 | QQSYSTPLT |
| 10 | 9 | SYFMH | 40 | WMNPNNGNTGYAQKFQG | 74 | QAGYSSGWDY | 104 | QASQDISNYLN | 130 | AAFNLQG | 156 | QQAHSFPLT |
| 11 | 10 | TWYMQ | 41 | WISPYTGNTIYAPNVQG | 75 | AVYDILTGAYYFDY | 110 | RASQSISSYLN | 131 | GASTLES | 157 | QQSYSTPIT |
| 12 | 11 | SYAIS | 42 | WISTYNGNTNYAQKFQG | 76 | GRLPPYYYGMDV | 111 | KSSQSVLYSSNKNYLA | 132 | WASTRES | 158 | QQYYSTPLT |
| 13 | 12 | RYYLH | 43 | RIIPILGIANYAQKFQG | 77 | MATVTKHTYWYFDL | 104 | QASQDISNYLN | 133 | ATSTLQS | 159 | QQANSLPYS |
| 14 | 13 | GQWVH | 44 | LISYDGGSTYYADSVKG | 78 | AGRSTSRYYYYMDV | 112 | RASENIGNWLA | 127 | AASTLQS | 160 | QQGYSTPYT |
| 15 | 14 | PNYIQ | 45 | IINPSGRSTSYAQKFQG | 79 | SSSGYTTDAFDI | 113 | RASQSVSSNLA | 134 | GASTRAT | 161 | QQYGTSPFT |
| 16 | 15 | ASYIH | 46 | GIIPIFGSPNYAQKFQG | 80 | EYQLMNVGMDV | 114 | RASQGISNNLN | 135 | AASILQS | 162 | QQSYTTTLT |

TABLE 1-continued

| Binding Agent | SEQ ID HCDR1 | SEQ ID HCDR2 | SEQ ID HCDR3 | SEQ ID LCDR1 | SEQ ID LCDR2 | SEQ ID LCDR3 |
|---|---|---|---|---|---|---|
| 17 | 16 DSHLH | 47 VIYAGGSRYYADSVKG | 81 GKQRADAFDI | 115 RASQSISKFLN | 136 SASNLQS | 163 QQANSFPLT |
| 18 | 13 GQWVH | 44 LISYDGGSTYYADSVKG | 78 AGRSTSRYYYYYMDV | 112 RASENIGNWLA | 127 AASTLQS | 160 QQGYSTPYT |
| 19 | 17 SYWMH | 48 TISGSGAGTWYADSVKG | 82 DVDPSRQSYYHGVDV | 116 RSSQSLLHSNGYNYLD | 137 LGSNRAS | 164 MQGAHWPYT |
| 20 | 18 NYWIQ | 49 WINPNSGGTRYARNFQG | 83 GRYYYGSGSQYHAFDI | 117 RASQSIGSYLN | 138 AASRLQS | 150 QQSYSTPLT |
| 21 | 19 NYYMH | 50 WLNPNSGTNYAQKFQG | 84 GRYDSSGYYYFDY | 118 QASQEIGNYLN | 139 GASSLQS | 150 QQSYSTPLT |
| 22 | 20 GYDMQ | 51 IINPSGAGTNYAQKFQG | 85 TVTTPYQYYGMDV | 116 RSSQSLLHSNGYNYLD | 126 AASSLQS | 165 MQALQTPLT |
| 23 | 21 SYSMN | 52 VISYDGRIKDYADSVKG | 86 VRGFSFWFDP | 110 RASQSISSYLN | 140 LASSLQS | 166 QQSYGIPLT |
| 23a | 21 SYSMN | 52 VISYDGRIKDYADSVKG | 86 VRGFSFWFDP | 110 RASQSISSYLN | 140 LASSLQS | 166 QQSYGIPLT |
| 23b | 21 SYSMN | 52 VISYDGRIKDYADSVKG | 323 VRGFSFWFEP | 110 RASQSISSYLN | 140 LASSLQS | 166 QQSYGIPLT |
| 24 | 6 SYWMS | 53 GISWNGGKTHYADSVKG | 87 GGGYFDY | 104 QASQDISNYLN | 141 KASSLES | 167 QQANTFPLT |
| 25 | 22 GYYIH | 38 WMNPNSGNTGYAQKFQG | 88 GRYGSSGWSPGYYYYYMDV | 119 QASQDITNFLN | 126 AASSLQS | 168 QQTYSFPLT |
| 26 | 6 SYWMS | 37 AISGSGGSTYYADSVKG | 89 ARDSGSPKDFDY | 120 RASQSISTFLN | 142 AASSLQT | 169 QQSYSTPP |
| 27 | 23 SYAMH | 54 GTSLDGNKNYYADSVKG | 90 GTMARGS | 121 QASQDISKYLN | 143 AASNLQK | 170 QQANSFPRT |
| 28 | 6 SYWMS | 55 TISGSGGTTYYADSVKG | 91 ATDYPGMDV | 122 QASQDIGNYLN | 126 AASSLQS | 171 LQHNSFPPT |
| 29 | 19 NYYMH | 56 WINPHSGGTNYAQKFQG | 92 GRMHYDSSVHYYYYGMDV | 123 RASQDIRNYLA | 127 AASTLQS | 172 LQAISFPFT |
| 30 | 11 SYAIS | 57 LIDPSPGTTYYAQKFQG | 93 VSIVGATPDYYYGMDV | 109 QASQDIRNYLN | 144 DTSNLET | 173 QQAYSLPWT |
| 31 | 4 SYDIN | 58 RINPNSGGTNFAQKFQG | 94 VIRGGKFDP | 104 QASQDISNYLN | 136 SASNLQS | 174 QQSYTTPYT |
| 32 | 24 NYGIT | 59 WMNPNSANTGYAQKFQG | 95 GLYAAAGDQYYYGMDV | 110 RASQSISSYLN | 127 AASTLQS | 153 QQSDSFPLT |
| 33 | 11 SYAIS | 60 VINPSGGGTTYAKKFQG | 96 GAAFDY | 111 KSSQSVLYSSNNKNYLA | 145 WASFRES | 175 QQYTTPLT |
| 34 | 25 GYYMH | 61 WINPDSGDTNFAQKFQG | 97 EYGDYGYYYYGMDV | 111 KSSQSVLYSSNNKNYLA | 146 WASARES | 176 QQYKSAPYT |
| 35 | 26 NYYIH | 59 WMNPNSANTGYAQKFQG | 98 GIYYYDSSGSYYYGMDV | 110 RASQSISSYLN | 126 AASSLQS | 177 QQSNSFPLT |
| 36 | 25 GYYMH | 38 WMNPNSGNTGYAQKFQG | 99 ELSSSWYSYGMDV | 124 RASQSISRHLN | 126 AASSLQS | 178 QQSYQTPLT |
| 37 | 27 DYGMY | 62 YISSSGSTIYYADSVKG | 100 VSGGSWYDRL | 111 KSSQSVLYSSNNKNYLA | 147 WASIRES | 179 QQYSSPFT |
| 38 | 28 SYGIN | 63 RIIPIFGAANYAQKFQG | 101 TYFDWFFFDY | 116 RSSQSLLHSNGYNYLD | 148 DASNLHA | 180 MQALQAPVT |
| 39 | 29 SYGIS | 64 WINPNNGGTNYAQKFQG | 102 GRYSGHFGVYYYGMDV | 121 QASQDISKYLN | 126 AASSLQS | 177 QQSNSFPLT |

TABLE 1-continued

| Binding Agent | SEQ ID HCDR1 | SEQ ID HCDR2 | SEQ ID HCDR3 | SEQ ID LCDR1 | SEQ ID LCDR2 | SEQ ID LCDR3 |
|---|---|---|---|---|---|---|
| 40 | 30 SYYMH | 38 WMNPNSGNTGYAQKFQG | 103 EPYGDYGFDY | 125 RASQTVRSYLN | 127 AASTLQS | 181 QQTYRTPLT |

TABLE 2

| Binding Agent | SEQ ID HFW1 | SEQ ID HFW2 | SEQ ID HFW3 | SEQ ID HFW4 |
|---|---|---|---|---|
| 1 | 182 QVQLVQSGAEVKKPGASVKVSCKASGYTFT | 201 WVRQAPGQGLEWMG | 208 RVTMTRDTSTSTVYMELSSLRSEDTAVYYCAR | 216 WGQGTTVTVSS |
| 2 | 183 QVQLVQSGAEVKKPGASVKVSCKASGYIFT | 201 WVRQAPGQGLEWMG | 208 RVTMTRDTSTSTVYMELSSLRSEDTAVYYCAR | 217 WGRGTLVTVSS |
| 3 | 184 QVQLVQSGAEVKKPGASVKVSCKASGGTLN | 201 WVRQAPGQGLEWMG | 208 RVTMTRDTSTSTVYMELSSLRSEDTAVYYCAR | 218 WGKGTTVTVSS |
| 4 | 182 QVQLVQSGAEVKKPGASVKVSCKASGYTFT | 202 WVRQAPGQGLEWLG | 208 RVTMTRDTSTSTVYMELSSLRSEDTAVYYCAR | 216 WGQGTTVTVSS |
| 5 | 182 QVQLVQSGAEVKKPGASVKVSCKASGYTFT | 201 WVRQAPGQGLEWMG | 208 RVTMTRDTSTSTVYMELSSLRSEDTAVYYCAR | 219 WGQGTMVTVSS |
| 6 | 185 EVQLLESGGGLVQPGGSLRLSCAASGFTFS | 203 WVRQAPGKGLEWVS | 209 RFTISRDNSKNTLYLQMNSLRAEDTAVYYCAR | 216 WGQGTTVTVSS |
| 7 | 185 EVQLLESGGGLVQPGGSLRLSCAASGFTFS | 203 WVRQAPGKGLEWVS | 209 RFTISRDNSKNTLYLQMNSLRAEDTAVYYCAR | 217 WGRGTLVTVSS |
| 8 | 182 QVQLVQSGAEVKKPGASVKVSCKASGYTFT | 201 WVRQAPGQGLEWMG | 208 RVTMTRDTSTSTVYMELSSLRSEDTAVYYCAR | 220 WGQGTLVTVSS |
| 9 | 182 QVQLVQSGAEVKKPGASVKVSCKASGYTFT | 201 WVRQAPGQGLEWMG | 208 RVTMTRDTSTSTVYMELSSLRSEDTAVYYCAR | 220 WGQGTLVTVSS |
| 10 | 182 QVQLVQSGAEVKKPGASVKVSCKASGYTFT | 201 WVRQAPGQGLEWMG | 210 RVTMTRDTSTSTVYMELSSLRSEDTAVYYCTR | 220 WGQGTLVTVSS |
| 11 | 186 QVQLVQSGAEVKKPGASVKVSCKASGYTLT | 201 WVRQAPGQGLEWMG | 210 RVTMTRDTSTSTVYMELSSLRSEDTAVYYCTR | 220 WGQGTLVTVSS |
| 12 | 187 QVQLVQSGAEVKKPGASVKVSCKASGGTFS | 201 WVRQAPGQGLEWMG | 208 RVTMTRDTSTSTVYMELSSLRSEDTAVYYCAR | 216 WGQGTTVTVSS |
| 13 | 188 QVQLVQSGVRWRSLGPPVKVSCKASGDTFS | 201 WVRQAPGQGLEWMG | 211 RVTITADESTSTAYMELSSLRSEDTAVYYCAR | 217 WGRGTLVTVSS |
| 14 | 185 EVQLLESGGGLVQPGGSLRLSCAASGFTFS | 204 WVRQAPGKGLEWVA | 209 RFTISRDNSKNTLYLQMNSLRAEDTAVYYCAR | 218 WGKGTTVTVSS |
| 15 | 183 QVQLVQSGAEVKKPGASVKVSCKASGYIFT | 201 WVRQAPGQGLEWMG | 208 RVTMTRDTSTSTVYMELSSLRSEDTAVYYCAR | 216 WGQGTTVTVSS |
| 16 | 189 QVQLVQSGAEVKKPGSSVKVSCKASGYTFT | 201 WVRQAPGQGLEWMG | 211 RVTITADESTSTAYMELSSLRSEDTAVYYCAR | 216 WGQGTTVTVSS |
| 17 | 190 EVQLLESGGGLVQPGGSLRLSCAASGFIFS | 205 WVRQAPGKGLEWLS | 209 RFTISRDNSKNTLYLQMNSLRAEDTAVYYCAR | 220 WGQGTLVTVSS |
| 18 | 185 EVQLLESGGGLVQPGGSLRLSCAASGFTFS | 204 WVRQAPGKGLEWVA | 209 RFTISRDNSKNTLYLQMNSLRAEDTAVYYCAR | 218 WGKGTTVTVSS |
| 19 | 191 EVQLLESGGGLVKPGGSLRLSCAASGFTFS | 203 WVRQAPGKGLEWVS | 212 RFTISRDDSKNTLYLQMNSLKTEDTAVYYCAR | 216 WGQGTTVTVSS |
| 20 | 183 QVQLVQSGAEVKKPGASVKVSCKASGYIFT | 201 WVRQAPGQGLEWMG | 208 RVTMTRDTSTSTVYMELSSLRSEDTAVYYCAR | 219 WGQGTMVTVSS |
| 21 | 192 QVQLVQSGAEVKKPGASVKVSCKASEYTFT | 201 WVRQAPGQGLEWMG | 208 RVTMTRDTSTSTVYMELSSLRSEDTAVYYCAR | 220 WGQGTLVTVSS |
| 22 | 193 QVQLVQSGAEVKKPGSSVKVSCKASGDTFT | 201 WVRQAPGQGLEWMG | 213 RVTITADESTSTAYMELSSLRSEDTAVYYCAG | 216 WGQGTTVTVSS |

TABLE 2-continued

| Binding Agent | SEQ ID HFW1 | SEQ ID HFW2 | SEQ ID HFW3 | SEQ ID HFW4 |
|---|---|---|---|---|
| 23 | 194 EVQLLESGGGLVQPGGSRLSCAASTFPFS | 204 WVRQAPGKGLEWVA | 209 RFTISRDNSKNTLYLQMNSLRAEDTAVYYCAR | 220 WGQGTLVTVSS |
| 23a | 185 EVQLLESGGGLVQPGGSRLSCAASGFTFS | 204 WVRQAPGKGLEWVA | 209 RFTISRDNSKNTLYLQMNSLRAEDTAVYYCAR | 220 WGQGTLVTVSS |
| 23b | 185 EVQLLESGGGLVQPGGSRLSCAASGFTFS | 204 WVRQAPGKGLEWVA | 209 RFTISRDNSKNTLYLQMNSLRAEDTAVYYCAR | 220 WGQGTLVTVSS |
| 24 | 185 EVQLLESGGGLVQPGGSRLSCAASGFTFS | 203 WVRQAPGKGLEWVS | 209 RFTISRDNSKNTLYLQMNSLRAEDTAVYYCAR | 220 WGQGTLVTVSS |
| 25 | 195 QVQLVQSGAEVKKPGASVKVSCKASGYSFT | 201 WVRQAPGQGLEWMG | 208 RVTMTRDTSTSTVYMELSSLRSEDTAVYYCAR | 218 WGKGTTVTVSS |
| 26 | 185 EVQLLESGGGLVQPGGSRLSCAASGFTFS | 203 WVRQAPGKGLEWVS | 209 RFTISRDNSKNTLYLQMNSLRAEDTAVYYCAR | 220 WGQGTLVTVSS |
| 27 | 185 EVQLLESGGGLVQPGGSRLSCAASGFTFS | 204 WVRQAPGKGLEWVA | 209 RFTISRDNSKNTLYLQMNSLRAEDTAVYYCAR | 220 WGQGTLVTVSS |
| 28 | 185 EVQLLESGGGLVQPGGSRLSCAASGFTFS | 203 WVRQAPGKGLEWVS | 214 RFTISRDNSKNTLYLQNEQPGAEDTAVYYCAR | 216 WGQGTTVTVSS |
| 29 | 186 QVQLVQSGAEVKKPGASVKVSCKASGYTLT | 201 WVRQAPGQGLEWMG | 210 RVTMTRDTSTSTVYMELSSLRSEDTAVYYCTR | 220 WGQGTLVTVSS |
| 30 | 196 QVQLVQSGAEVKKPGASVKVSCKASGGTGS | 201 WVRQAPGQGLEWMG | 208 RVTMTRDTSTSTVYMELSSLRSEDTAVYYCAR | 221 WGKGTLVTVSS |
| 31 | 182 QVQLVQSGAEVKKPGASVKVSCKASGYTFT | 201 WVRQAPGQGLEWMG | 208 RVTMTRDTSTSTVYMELSSLRSEDTAVYYCAR | 220 WGQGTLVTVSS |
| 32 | 189 QVQLVQSGAEVKKPGSSVKVSCKASGYTFT | 206 WVRQAPGKGLEWMG | 211 RVTITADESTSTAYMELSSLRSEDTAVYYCAR | 220 WGQGTLVTVSS |
| 33 | 197 QVQLVQSGAEVKKPGASVKVSCKASGDTFS | 201 WVRQAPGQGLEWMG | 208 RVTMTRDTSTSTVYMELSSLRSEDTAVYYCAR | 220 WGQGTLVTVSS |
| 34 | 189 QVQLVQSGAEVKKPGSSVKVSCKASGYTFT | 201 WVRQAPGQGLEWMG | 211 RVTITADESTSTAYMELSSLRSEDTAVYYCAR | 219 WGQGTMVTVSS |
| 35 | 182 QVQLVQSGAEVKKPGASVKVSCKASGYTFT | 201 WVRQAPGQGLEWMG | 208 RVTMTRDTSTSTVYMELSSLRSEDTAVYYCAR | 216 WGQGTTVTVSS |
| 36 | 182 QVQLVQSGAEVKKPGASVKVSCKASGYTFT | 201 WVRQAPGQGLEWMG | 208 RVTMTRDTSTSTVYMELSSLRSEDTAVYYCAR | 216 WGQGTTVTVSS |
| 37 | 198 EVQLLESGGGLVKPGGSRLSCAASGFTLS | 203 WVRQAPGKGLEWVS | 212 RFTISRDDSKNTLYLQMNSLKTEDTAVYYCAR | 222 LGPGNPVTVSS |
| 38 | 199 QVQLVQSGAEVKKPGSSVKVSCKASGYTFS | 201 WVRQAPGQGLEWMG | 215 RVTITADESTSTAYMELSSLRSEDTAVYYCTR | 220 WGQGTLVTVSS |
| 39 | 182 QVQLVQSGAEVKKPGASVKVSCKASGYTFT | 201 WVRQAPGQGLEWMG | 208 RVTMTRDTSTSTVYMELSSLRSEDTAVYYCAR | 216 WGQGTTVTVSS |
| 40 | 200 QVQLVQSGAEVKKPGASVKVSCKASGYTFS | 207 WVRQAPGQGLEWMA | 208 RVTMTRDTSTSTVYMELSSLRSEDTAVYYCAR | 220 WGQGTLVTVSS |

TABLE 3

| Binding Agent | SEQ ID LFW1 | SEQ ID LFW2 | SEQ ID LFW3 | SEQ ID LFW4 |
|---|---|---|---|---|
| 1 | 223 DIQMTQSPSSLSASVGDRVTITC | 228 WYQQKPGKAPKLLIY | 233 GVPSRFSGSGSGTDFTLTISSLQPEDFATYYC | 237 FGQGTKVEIK |
| 2 | 223 DIQMTQSPSSLSASVGDRVTITC | 228 WYQQKPGKAPKLLIY | 233 GVPSRFSGSGSGTDFTLTISSLQPEDFATYYC | 238 FGPGTKVDIK |
| 3 | 223 DIQMTQSPSSLSASVGDRVTITC | 228 WYQQKPGKAPKLLIY | 233 GVPSRFSGSGSGTDFTLTISSLQPEDFATYYC | 239 FGGGTKVEIK |

TABLE 3-continued

| Binding Agent | SEQ ID LFW1 | SEQ ID LFW2 | SEQ ID LFW3 | SEQ ID LFW4 |
|---|---|---|---|---|
| 4 | 223 DIQMTQSPSSLSASVGDRVTITC | 228 WYQQKPGKAPKLLIY | 233 GVPSRFSGSGSGTDFTLTISSLQPEDFATYYC | 237 FGQGTKVEIK |
| 5 | 223 DIQMTQSPSSLSASVGDRVTITC | 228 WYQQKPGKAPKLLIY | 233 GVPSRFSGSGSGTDFTLTISSLQPEDFATYYC | 240 FGQGTRLEIK |
| 6 | 223 DIQMTQSPSSLSASVGDRVTITC | 228 WYQQKPGKAPKLLIY | 233 GVPSRFSGSGSGTDFTLTISSLQPEDFATYYC | 239 FGGGTKVEIK |
| 7 | 223 DIQMTQSPSSLSASVGDRVTITC | 228 WYQQKPGKAPKLLIY | 233 GVPSRFSGSGSGTDFTLTISSLQPEDFATYYC | 241 FGQGTKLEIK |
| 8 | 223 DIQMTQSPSSLSASVGDRVTITC | 228 WYQQKPGKAPKLLIY | 233 GVPSRFSGSGSGTDFTLTISSLQPEDFATYYC | 239 FGGGTKVEIK |
| 9 | 223 DIQMTQSPSSLSASVGDRVTITC | 228 WYQQKPGKAPKLLIY | 233 GVPSRFSGSGSGTDFTLTISSLQPEDFATYYC | 239 FGGGTKVEIK |
| 10 | 223 DIQMTQSPSSLSASVGDRVTITC | 228 WYQQKPGKAPKLLIY | 233 GVPSRFSGSGSGTDFTLTISSLQPEDFATYYC | 238 FGPGTKVDIK |
| 11 | 223 DIQMTQSPSSLSASVGDRVTITC | 228 WYQQKPGKAPKLLIY | 233 GVPSRFSGSGSGTDFTLTISSLQPEDFATYYC | 241 FGQGTKLEIK |
| 12 | 224 DIVMTQSPDSLAVSLGERATINC | 229 WYQQKPGQPPKLLIY | 234 GVPDRFSGSGSGTDFTLTISSLQAEDVAVYYC | 237 FGQGTKVEIK |
| 13 | 223 DIQMTQSPSSLSASVGDRVTITC | 228 WYQQKPGKAPKLLIY | 233 GVPSRFSGSGSGTDFTLTISSLQPEDFATYYC | 241 FGQGTKLEIK |
| 14 | 223 DIQMTQSPSSLSASVGDRVTITC | 228 WYQQKPGKAPKLLIY | 233 GVPSRFSGSGSGTDFTLTISSLQPEDFATYYC | 241 FGQGTKLEIK |
| 15 | 225 EIVMTQSPATLSVSPGERATLSC | 230 WYQQKPGQAPRLLIY | 235 GIPARFSGSGSG1EFTLTISSLQSEDFAVYYC | 240 FGQGTRLEIK |
| 16 | 223 DIQMTQSPSSLSASVGDRVTITC | 228 WYQQKPGKAPKLLIY | 233 GVPSRFSGSGSGTDFTLTISSLQPEDFATYYC | 238 FGPGTKVDIK |
| 17 | 223 DIQMTQSPSSLSASVGDRVTITC | 228 WYQQKPGKAPKLLIY | 233 GVPSRFSGSGSGTDFTLTISSLQPEDFATYYC | 237 FGQGTKVEIK |
| 18 | 223 DIQMTQSPSSLSASVGDRVTITC | 231 WYHQKPGKAPKLLIY | 233 SGVPSRFSGSGSGTDFTLTISSLQPEDFATYYC | 241 FGQGTKLEIK |
| 19 | 226 DIVMTQSPLFLPVTPGEPASISC | 232 WYLQKPGQSPQLLIY | 236 GVPDRFSGSGSGTDFTLKISRVEAEDVGVYYC | 241 FGQGTKLEIK |
| 20 | 223 DIQMTQSPSSLSASVGDRVTITC | 228 WYQQKPGKAPKLLIY | 233 GVPSRFSGSGSGTDFTLTISSLQPEDFATYYC | 237 FGQGTKVEIK |
| 21 | 223 DIQMTQSPSSLSASVGDRVTITC | 228 WYQQKPGKAPKLLIY | 233 GVPSRFSGSGSGTDFTLTISSLQPEDFATYYC | 239 FGGGTKVEIK |
| 22 | 227 DIVMTQSPLSLPVTPGEPASISC | 232 WYLQKPGQSPQLLIY | 236 GVPDRFSGSGSGTDFTLKISRVEAEDVGVYYC | 239 FGGGTKVEIK |
| 23 | 223 DIQMTQSPSSLSASVGDRVTITC | 228 WYQQKPGKAPKLLIY | 233 GVPSRFSGSGSGTDFTLTISSLQPEDFATYYC | 239 FGGGTKVEIK |
| 23a | 223 DIQMTQSPSSLSASVGDRVTITC | 228 WYQQKPGKAPKLLIY | 233 GVPSRFSGSGSGTDFTLTISSLQPEDFATYYC | 239 FGGGTKVEIK |
| 23b | 223 DIQMTQSPSSLSASVGDRVTITC | 228 WYQQKPGKAPKLLIY | 233 GVPSRFSGSGSGTDFTLTISSLQPEDFATYYC | 239 FGGGTKVEIK |
| 24 | 223 DIQMTQSPSSLSASVGDRVTITC | 228 WYQQKPGKAPKLLIY | 233 GVPSRFSGSGSGTDFTLTISSLQPEDFATYYC | 239 FGGGTKVEIK |
| 25 | 223 DIQMTQSPSSLSASVGDRVTITC | 228 WYQQKPGKAPKLLIY | 233 GVPSRFSGSGSGTDFTLTISSLQPEDFATYYC | 238 FGPGTKVDIK |
| 26 | 223 DIQMTQSPSSLSASVGDRVTITC | 228 WYQQKPGKAPKLLIY | 233 GVPSRFSGSGSGTDFTLTISSLQPEDFATYYC | 238 FGPGTKVDIK |
| 27 | 223 DIQMTQSPSSLSASVGDRVTITC | 228 WYQQKPGKAPKLLIY | 233 GVPSRFSGSGSGTDFTLTISSLQPEDFATYYC | 237 FGQGTKVEIK |

TABLE 3-continued

| Binding Agent | SEQ ID | LFW1 | SEQ ID | LFW2 | SEQ ID | LFW3 | SEQ ID | LFW4 |
|---|---|---|---|---|---|---|---|---|
| 28 | 223 | DIQMTQSPSSLSASVGDRVTITC | 228 | WYQQKPGKAPKLLIY | 233 | GVPSRFSGSGSGTDFTLTISSLQPEDFATYYC | 239 | FGGGTKVEIK |
| 29 | 223 | DIQMTQSPSSLSASVGDRVTITC | 228 | WYQQKPGKAPKLLIY | 233 | GVPSRFSGSGSGTDFTLTISSLQPEDFATYYC | 238 | FGPGTKVDIK |
| 30 | 223 | DIQMTQSPSSLSASVGDRVTITC | 228 | WYQQKPGKAPKLLIY | 233 | GVPSRFSGSGSGTDFTLTISSLQPEDFATYYC | 241 | FGQGTKLEIK |
| 31 | 223 | DIQMTQSPSSLSASVGDRVTITC | 228 | WYQQKPGKAPKLLIY | 233 | GVPSRFSGSGSGTDFTLTISSLQPEDFATYYC | 241 | FGQGTKLEIK |
| 32 | 223 | DIQMTQSPSSLSASVGDRVTITC | 228 | WYQQKPGKAPKLLIY | 233 | GVPSRFSGSGSGTDFTLTISSLQPEDFATYYC | 237 | FGQGTKVEIK |
| 33 | 224 | DIVMTQSPDSLAVSLGERATINC | 229 | WYQQKPGQPPKLLIY | 234 | GVPDRFSGSGSGTDFTLTISSLQAEDVAVYYC | 239 | FGQGTKVEIK |
| 34 | 224 | DIVMTQSPDSLAVSLGERATINC | 229 | WYQQKPGQPPKLLIY | 234 | GVPDRFSGSGSGTDFTLTISSLQAEDVAVYYC | 237 | FGQGTKVEIK |
| 35 | 223 | DIQMTQSPSSLSASVGDRVTITC | 228 | WYQQKPGKAPKLLIY | 233 | GVPSRFSGSGSGTDFTLTISSLQPEDFATYYC | 238 | FGPGTKVDIK |
| 36 | 223 | DIQMTQSPSSLSASVGDRVTITC | 228 | WYQQKPGKAPKLLIY | 233 | GVPSRFSGSGSGTDFTLTISSLQPEDFATYYC | 239 | FGGGTKVEIK |
| 37 | 224 | DIVMTQSPDSLAVSLGERATINC | 229 | WYQQKPGQPPKLLIY | 234 | GVPDRFSGSGSGTDFTLTISSLQAEDVAVYYC | 241 | FGQGTKLEIK |
| 38 | 227 | DIVMTQSPLSLPVTPGEPASISC | 232 | WYLQKPGQSPQLLIY | 236 | GVPDRFSGSGSGTDFTLKISRVEAEDVGVYYC | 240 | FGQGTRLEIK |
| 39 | 223 | DIQMTQSPSSLSASVGDRVTITC | 228 | WYQQKPGKAPKLLIY | 233 | GVPSRFSGSGSGTDFTLTISSLQPEDFATYYC | 242 | FGGGTKLEIK |
| 40 | 223 | DIQMTQSPSSLSASVGDRVTITC | 228 | WYQQKPGKAPKLLIY | 233 | GVPSRFSGSGSGTDFTLTISSLQPEDFATYYC | 237 | FGQGTKVEIK |

TABLE 4

| Binding Agent | SEQ ID | VH |
|---|---|---|
| 1 | 243 | QVQLVQSGAEVKKPGASVKVSCKASGYTFTSYYMQWVRQAPGQGLEWMGWINPKSGGTNYAQKFQGRVTMTRDTSTSTVYMELSSLRSEDTAVYYCARGTYLRTGSSLSGYYYGMDVWGQGTTVTVSS |
| 2 | 244 | QVQLVQSGAEVKKPGASVKVSCKASGYIFTTYYMHWVRQAPGQGLEWMGIINPSGGSTSYAQKFQGRVTMTRDTSTSTVYMELSSLRSEDTAVYYCARSHYGDLNGGFDLWGRGTLVTVSS |
| 3 | 245 | QVQLVQSGAEVKKPGASVKVSCKASGGTLNNFGINWVRQAPGQGLEWMGWINPNSGGANYAQKFQGRVTMTRDTSTSTVYMELSSLRSEDTAVYYCARGVVAARYYYMDVWGKGTTVTVSS |
| 4 | 246 | QVQLVQSGAEVKKPGASVKVSCKASGYTFTSYDINWVRQAPGQGLEWLGWINPNSGATNSAQKFQGRVTMTRDTSTSTVYMELSSLRSEDTAVYYCARAGYSSSWDGYYYYGMDVWGQGTTVTVSS |
| 5 | 247 | QVQLVQSGAEVKKPGASVKVSCKASGYTFTGYYVHWVRQAPGQGLEWMGIIHPNGGSTSYAQKFQGRVTMTRDTSTSTVYMELSSLRSEDTAVYYCARDQAGTGGHGMDVWGQGTMVTVSS |
| 6 | 248 | EVQLLESGGGLVQPGGSLRLSCAASGFTFSSYWMSWVRQAPGKGLEWVSDISGSGRSTYYADSVKGRFTISRDNSKNTLYLQMNSLRAEDTAVYYCARGRYLEWVLSSEDYYFGMDVWGQGTTVTVSS |
| 7 | 249 | EVQLLESGGGLVQPGGSLRLSCAASGFTFSSYWMSWVRQAPGKGLEWVSAISGSGGSTYYADSVKGRFTISRDNSKNTLYLQMNSLRAEDTAVYYCARGRYSRSWERWYFDLWGRGTLVTVSS |
| 8 | 250 | QVQLVQSGAEVKKPGASVKVSCKASGYTFTSQYMHWVRQAPGQGLEWMGWMNPNSGNTGYAQKFQGRVTMTRDTSTSTVYMELSSLRSEDTAVYYCARGQYDSSGYYYFDYWGQGTLVTVSS |
| 9 | 251 | QVQLVQSGAEVKKPGASVKVSCKASGYTFTTYYMNWVRQAPGQGLEWMGILSPSGGGTSYAPKFQGRVTMTRDTSTSTVYMELSSLRSEDTAVYYCARATYYDFWSGSLDYWGQGTLVTVSS |
| 10 | 252 | QVQLVQSGAEVKKPGASVKVSCKASGYTFTSYFMHWVRQAPGQGLEWMGWMNPNNGNTGYAQKFQGRVTMTRDTSTSTVYMELSSLRSEDTAVYYCTRQAGYSSGWDYWGQGTLVTVSS |

TABLE 4-continued

| Binding Agent | SEQ ID | VH |
|---|---|---|
| 11 | 253 | QVQLVQSGAEVKKPGASVKVSCKASGYTLTTWYMQWVRQAPGQGLEWMGWISPYTGNTIYAPNVQGRVTMTRDTSTSTVYMELSSLRSEDTAVYYCTRAVYDILTGAYYFDYWGQGTLVTVSS |
| 12 | 254 | QVQLVQSGAEVKKPGASVKVSCKASGGTFSSYAISWVRQAPGQGLEWMGWISTYNGNTNYAQKFQGRVTMTRDTSTSTVYMELSSLRSEDTAVYYCARGRLPPYYYGMDVWGQGTTVTVSS |
| 13 | 255 | QVQLVQSGVRWRSLGPPVKVSCKASGDTFSRYYLHWVRQAPGQGLEWMGRIIPILGIANYAQKFQGRVTITADESTSTAYMELSSLRSEDTAVYYCARMATVTKHTYWYFDLWGRGTLVTVSS |
| 14 | 256 | EVQLLESGGGLVQPGGSLRLSCAASGFTFSGQWVHWVRQAPGKGLEWVALISYDGGSTYYADSVKGRFTISRDNSKNTLYLQMNSLRAEDTAVYYCARAGRSTSRYYYYYMDVWGKGTTVTVSS |
| 15 | 257 | QVQLVQSGAEVKKPGASVKVSCKASGYIFTPNYIQWVRQAPGQGLEWMGIINPSGRSTSYAQKFQGRVTMTRDTSTSTVYMELSSLRSEDTAVYYCARSSSGYTTDAFDIWGQGTTVTVSS |
| 16 | 258 | QVQLVQSGAEVKKPGSSVKVSCKASGYTFTASYIEIWVRQAPGQGLEWMGGIIPIFGSPNYAQKFQGRVTITADESTSTAYMELSSLRSEDTAVYYCAREYQLMNVGMDVWGQGTTVTVSS |
| 17 | 259 | EVQLLESGGGLVQPGGSLRLSCAASGFIFSDSHLHWVRQAPGKGLEWLSVIYAGGSRYYADSVKGRFTISRDNSKNTLYLQMNSLRAEDTAVYYCARGKQRADAFDIWGQGTLVTVSS |
| 18 | 256 | EVQLLESGGGLVQPGGSLRLSCAASGFTFSGQWVHWVRQAPGKGLEWVALISYDGGSTYYADSVKGRFTISRDNSKNTLYLQMNSLRAEDTAVYYCARAGRSTSRYYYYYMDVWGKGTTVTVSS |
| 19 | 260 | EVQLLESGGGLVKPGGSLRLSCAASGFTFSSYWMHWVRQAPGKGLEWVSTISGSGAGTWYADSVKGRFTISRDDSKNTLYLQMNSLKTEDTAVYYCARDVDPSRQSYYHGVDVWGQGTTVTVSS |
| 20 | 261 | QVQLVQSGAEVKKPGASVKVSCKASGYIFTNYWIQWVRQAPGQGLEWMGWINPNSGGTRYARNFQGRVTMTRDTSTSTVYMELSSLRSEDTAVYYCARGRYYYGSGSQYHAFDIWGQGTMVTVSS |
| 21 | 262 | QVQLVQSGAEVKKPGASVKVSCKASEYTFTNYYMHWVRQAPGQGLEWMGWLNPNSGTNYAQKFQGRVTMTRDTSTSTVYMELSSLRSEDTAVYYCARGRYDSSGYYYFDYWGQGTLVTVSS |
| 22 | 263 | QVQLVQSGAEVKKPGSSVKVSCKASGDTFTGYDMQWVRQAPGQGLEWMGIINPSGAGTNYAQKFQGRVTITADESTSTAYMELSSLRSEDTAVYYCAGTVTTPYQYYGMDVWGQGTTVTVSS |
| 23 | 264 | EVQLLESGGGLVQPGGSLRLSCAASTFPFSSYSMNWVRQAPGKGLEWVAVISYDGRIKDYADSVKGRFTISRDNSKNTLYLQMNSLRAEDTAVYYCARVRGFSFWFDPWGQGTLVTVSS |
| 23a | 265 | EVQLLESGGGLVQPGGSLRLSCAASGFTFSSYSMNWVRQAPGKGLEWVAVISYDGRIKDYADSVKGRFTISRDNSKNTLYLQMNSLRAEDTAVYYCARVRGFSFWFDPWGQGTLVTVSS |
| 23b | 324 | EVQLLESGGGLVQPGGSLRLSCAASGFTFSSYSMNWVRQAPGKGLEWVAVISYDGRIKDYADSVKGRFTISRDNSKNTLYLQMNSLRAEDTAVYYCARVRGFSFWFEPWGQGTLVTVSS |
| 24 | 266 | EVQLLESGGGLVQPGGSLRLSCAASGFTFSSYWMSWVRQAPGKGLEWVSGISWNGGKTHYADSVKGRFTISRDNSKNTLYLQMNSLRAEDTAVYYCARGGGYFDYWGQGTLVTVSS |
| 25 | 267 | QVQLVQSGAEVKKPGASVKVSCKASGYSFKAYYIHWVRQAPGQGLEWMGWMNPNSGNTGYAQKFQGRVTMTRDTSTSTVYMELSSLRSEDTAVYYCARGRYGSSGWSPGYYYYYMDVWGKGTTVTVSS |
| 26 | 268 | EVQLLESGGGLVQPGGSLRLSCAASGFTFSSYWMSWVRQAPGKGLEWVSAISGSGGSTYYADSVKGRFTISRDNSKNTLYLQMNSLRAEDTAVYYCARARDSGSPKDFDYWGQGTLVTVSS |
| 27 | 269 | EVQLLESGGGLVQPGGSLRLSCAASGFTFSSYAMHWVRQAPGKGLEWVAGTSLDGNKNYYADSVKGRFTISRDNSKNTLYLQMNSLRAEDTAVYYCARGTMARGSWGQGTLVTVSS |
| 28 | 270 | EVQLLESGGGLVQPGGSLRLSCAASGFTFSSYWMSWVRQAPGKGLEWVSTISGSGGTTYYADSVKGRFTISRDNSKNTLYLQNEQPGAEDTAVYYCARATDYPGMDVWGQGTTVTVSS |
| 29 | 271 | QVQLVQSGAEVKKPGASVKVSCKASGYTLTNYYMHWVRQAPGQGLEWMGWINPHSGGTNYAQKFQGRVTMTRDTSTSTVYMELSSLRSEDTAVYYCTRGRMHYDSSVHYYYYGMDVWGQGTLVTVSS |
| 30 | 272 | QVQLVQSGAEVKKPGASVKVSCKASGGTGSSYAISWVRQAPGQGLEWMGL1DPSPGTTYYAQKFQGRVTMTRDTSTSTVYMELSSLRSEDTAVYYCARVSIVGATPDYYYGMDVWGKGTLVTVSS |
| 31 | 273 | QVQLVQSGAEVKKPGASVKVSCKASGYTFTSYDINWVRQAPGQGLEWMGRINPNSGGTNFAQKFQGRVTMTRDTSTSTVYMELSSLRSEDTAVYYCARVIRGGKFDPWGQGTLVTVSS |
| 32 | 274 | QVQLVQSGAEVKKPGSSVKVSCKASGYTFTNYGITWVRQAPGKGLEWMGWMNPNSANTGYAQKFQGRVTITADESTSTAYMELSSLRSEDTAVYYCARGLYAAAGDQYYYGMDVWGQGTLVTVSS |
| 33 | 275 | QVQLVQSGAEVKKPGASVKVSCKASGDTFSSYAISWVRQAPGQGLEWMGVINPSGGGTTYAKKFQGRVTMTRDTSTSTVYMELSSLRSEDTAVYYCARGAAFDYWGQGTLVTVSS |
| 34 | 276 | QVQLVQSGAEVKKPGSSVKVSCKASGYTFTGYYMHWVRQAPGQGLEWMGWINPDSGDTNFAQKFQGRVTITADESTSTAYMELSSLRSEDTAVYYCAREYGDYGYYYYGMDVWGQGTMVTVSS |

TABLE 4-continued

| Binding Agent | SEQ ID | VH |
|---|---|---|
| 35 | 277 | QVQLVQSGAEVKKPGASVKVSCKASGYTFTNYYIHWVRQAPGQGLEWMGWMNPNSANTGYAQKFQGRVTMTR DTSTSTVYMELSSLRSEDTAVYYCARGIYYYDSSGGSYYYGMDVWGQGTTVTVSS |
| 36 | 278 | QVQLVQSGAEVKKPGASVKVSCKASGYTFTGYYMHWVRQAPGQGLEWMGWMNPNSGNTGYAQKFQGRVTMT RDTSTSTVYMELSSLRSEDTAVYYCARELSSSWYSYGMDVWGQGTTVTVSS |
| 37 | 279 | EVQLLESGGGLVKPGGSLRLSCAASGFTLSDYGMYWVRQAPGKGLEWVSYISSSGSTIYYADSVKGRFTISRDDSK NTLYLQMNSLKTEDTAVYYCARVSGGSWYDRLLGPGNPVTVSS |
| 38 | 280 | QVQLVQSGAEVKKPGSSVKVSCKASGYTFSSYGINWVRQAPGQGLEWMGRIIPIFGAANYAQKFQGRVTITADEST STAYMELSSLRSEDTAVYYCTRTYFDWFFFDYWGQGTLVTVSS |
| 39 | 281 | QVQLVQSGAEVKKPGASVKVSCKASGYTFTSYGISWVRQAPGQGLEWMGWINPNNGGTNYAQKFQGRVTMTRD TSTSTVYMELSSLRSEDTAVYYCARGRYSGHFGVYYYGMDVWGQGTTVTVSS |
| 40 | 282 | QVQLVQSGAEVKKPGASVKVSCKASGYTFSSYYME1WVRQAPGQGLEWMAWMNPNSGNTGYAQKFQGRVTMT RDTSTSTVYMELSSLRSEDTAVYYCAREPYGDYGFDYWGQGTLVTVSS |

TABLE 5

| Binding Agent | SEQ ID | VL |
|---|---|---|
| 1 | 283 | DIQMTQSPSSLSASVGDRVTITCQASQDISNYLNWYQQKPGKAPKLLIYAASSLQSGVPSRFSGSGSGTDFTLTIS SLQPEDFATYYCQQTDSIPITFGQGTKVEIK |
| 2 | 284 | DIQMTQSPSSLSASVGDRVTITCRASQYISSYLAWYQQKPGKAPKLLIYAASTLQSGVPSRFSGSGSGTDFTLTISS LQPEDFATYYCQQSYSTPLTFGPGTKVDIK |
| 3 | 285 | DIQMTQSPSSLSASVGDRVTITCRASQNIGSYLNWYQQKPGKAPKLLIYAASSLQSGVPSRFSGSGSGTDFTLTIS SLQPEDFATYYCQQTNSFPLTFGGGTKVEIK |
| 4 | 286 | DIQMTQSPSSLSASVGDRVTITCRASQSISSHLNWYQQKPGKAPKLLIYAASTLQSGVPSRFSGSGSGTDFTLTISS LQPEDFATYYCQQSYSTPLTFGQGTKVEIK |
| 5 | 287 | DIQMTQSPSSLSASVGDRVTITCRASQSINNWLAWYQQKPGKAPKLLIYAASTLQSGVPSRFSGSGSGTDFTLTIS SLQPEDFATYYCEQNYRLPITFGQGTRLEIK |
| 6 | 288 | DIQMTQSPSSLSASVGDRVTITCQASQDISNYLNWYQQKPGKAPKLLIYAASSLHPGVPSRFSGSGSGTDFTLTIS SLQPEDFATYYCQQSDSFPLTFGGGTKVEIK |
| 7 | 289 | DIQMTQSPSSLSASVGDRVTITCQASQDISNYLNWYQQKPGKAPKLLIYAASNLESGVPSRFSGSGSGTDFTLTIS SLQPEDFATYYCQQTNSFPITFGQGTKLEIK |
| 8 | 290 | DIQMTQSPSSLSASVGDRVTITCQASQDIRNYLNWYQQKPGKAPKLLIYAASTLQSGVPSRFSGSGSGTDFTLTIS SLQPEDFATYYCQQSYSFPLTFGGGTKVEIK |
| 9 | 291 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 10 | 292 | DIQMTQSPSSLSASVGDRVTITCQASQDISNYLNWYQQKPGKAPKLLIYAAFNLQGGVPSRFSGSGSGTDFTLTIS SLQPEDFATYYCQQAHSFPLTFGPGTKVDIK |
| 11 | 293 | DIQMTQSPSSLSASVGDRVTITCRASQSISSYLNWYQQKPGKAPKLLIYGASTLESGVPSRFSGSGSGTDFTLTISS LQPEDFATYYCQQSYSTPITFGQGTKLEIK |
| 12 | 294 | DIVNITQSPDSLAVSLGERATINCKSSQSVLYSSNNKNYLAWYQQKPGQPPKWYWASTRESGVPDRFSGSGSG TDFTLTISSLQAEDVAVYYCQQYYSTPLTFGQGTKVE1K |
| 13 | 295 | DIQMTQSPSSLSASVGDRVTITCQASQDISNYLNWYQQKPGKAPKLLIYATSTLQSGVPSRFSGSGSGTDFTLTIS SLQPEDFATYYCQQANSLPYSFGQGTKLEIK |
| 14 | 296 | DIQMTQSPSSLSASVGDRVTITCRASENIGNWLAWYQQKPGKAPKLLIYAASTLQSGVPSRFSGSGSGTDFTLTIS SLQPEDFATYYCQQGYSTPYTFGQGTKLEIK |
| 15 | 297 | EIVIVITQSPATLSVSPGERATLSCRASQSVSSNLAWYQQKPGQAPRLLIYGASTRATGIPARFSGSGSGTEFTLTISS LQSEDFAVYYCQQYGTSPFTFGQGTRLEIK |
| 16 | 298 | DIQMTQSPSSLSASVGDRVTITCRASQGISNNLNWYQQKPGKAPKLLIYAASILQSGVPSRFSGSGSGTDFTLTISS LQPEDFATYYCQQSYTTTLTFGPGTKVDIK |
| 17 | 299 | DIQMTQSPSSLSASVGDRVTITCRASQSISKFLNWYQQKPGKAPKWYSASNLQSGVPSRFSGSGSGTDFTLTISS LQPEDFATYYCQQANSFPLTFGQGTKVEIK |

TABLE 5-continued

| Binding Agent | SEQ ID | VL |
|---|---|---|
| 18 | 300 | DIQMTQSPSSLSASVGDRVTITCRASENIGNWLAWYHQKPGKAPKLLIYAASTLQSGVPSRFSGSGSGTDFTLTISSLQPEDFATYYCQQGYSTPYTFGQGTKLEIK |
| 19 | 301 | DIVNITQSPLFLPVTPGEPASISCRSSQSLLHSNGYNYLDWYLQKPGQSPQLLIYLGSNRASGVPDRFSGSGSGTDFTLKISRVEAEDVGVYYCMQGAHWPYTFGQGTKLEIK |
| 20 | 302 | DIQMTQSPSSLSASVGDRVTITCRASQSIGSYLNWYQQKPGKAPKLLIYAASRLQSGVPSRFSGSGSGTDFTLTISSLQPEDFATYYCQQSYSTPLTFGQGTKVEIK |
| 21 | 303 | DIQMTQSPSSLSASVGDRVTITCQASQEIGNYLNWYQQKPGKAPKWYGASSLQSGVPSRFSGSGSGTDFTLTISSLQPEDFATYYCQQSYSTPLTFGGGTKVEIK |
| 22 | 304 | DIVNITQSPLSLPVTPGEPASISCRSSQSLLHSNGYNYLDWYLQKPGQSPQLLIYAASSLQSGVPDRFSGSGSGTDFTLKISRVEAEDVGVYYCMQALQTPLTFGGGTKVEIK |
| 23 | 305 | DIQMTQSPSSLSASVGDRVTITCRASQSISSYLNWYQQKPGKAPKWYLASSLQSGVPSRFSGSGSGTDFTLTISSLQPEDFATYYCQQSYGIPLTFGGGTKVEIK |
| 23a | 305 | DIQMTQSPSSLSASVGDRVTITCRASQSISSYLNWYQQKPGKAPKWYLASSLQSGVPSRFSGSGSGTDFTLTISSLQPEDFATYYCQQSYGIPLTFGGGTKVEIK |
| 23b | 305 | DIQMTQSPSSLSASVGDRVTITCRASQSISSYLNWYQQKPGKAPKWYLASSLQSGVPSRFSGSGSGTDFTLTISSLQPEDFATYYCQQSYGIPLTFGGGTKVEIK |
| 24 | 306 | DIQMTQSPSSLSASVGDRVTITCQASQDISNYLNWYQQKPGKAPKWYKASSLESGVPSRFSGSGSGTDFTLTISSLQPEDFATYYCQQANTFPLTFGGGTKVEIK |
| 25 | 307 | DIQMTQSPSSLSASVGDRVTITCQASQDITNFLNWYQQKPGKAPKLLIYAASSLQSGVPSRFSGSGSGTDFTLTISSLQPEDFATYYCQQTYSFPLTFGPGTKVDIK |
| 26 | 308 | DIQMTQSPSSLSASVGDRVTITCRASQSISTFLNWYQQKPGKAPKLLIYAASSLQTGVPSRFSGSGSGTDFTLTISSLQPEDFATYYCQQSYSTPPFGPGTKVDIK |
| 27 | 309 | DIQMTQSPSSLSASVGDRVTITCQASQDISKYLNWYQQKPGKAPKLLIYAASNLQKGVPSRFSGSGSGTDFTLTISSLQPEDFATYYCQQANSFPRTFGQGTKVEIK |
| 28 | 310 | DIQMTQSPSSLSASVGDRVTITCQASQDIGNYLNWYQQKPGKAPKLLIYAASSLQSGVPSRFSGSGSGTDFTLTISSLQPEDFATYYCLQHNSFPPTFGGGTKVEIK |
| 29 | 311 | DIQMTQSPSSLSASVGDRVTITCRASQDIRNYLAWYQQKPGKAPKLLIYAASTLQSGVPSRFSGSGSGTDFTLTISSLQPEDFATYYCLQAISFPFTFGPGTKVDIK |
| 30 | 312 | DIQMTQSPSSLSASVGDRVTITCQASQDIRNYLNWYQQKPGKAPKLLIYDTSNLETGVPSRFSGSGSGTDFTLTISSLQPEDFATYYCQQAYSLPWTFGQGTKLEIK |
| 31 | 313 | DIQMTQSPSSLSASVGDRVTITCQASQDISNYLNWYQQKPGKAPKLLIYSASNLQSGVPSRFSGSGSGTDFTLTISSLQPEDFATYYCQQSYTTPYTFGQGTKLEIK |
| 32 | 314 | DIQMTQSPSSLSASVGDRVTITCRASQSISSYLNWYQQKPGKAPKLLIYAASTLQSGVPSRFSGSGSGTDFTLTISSLQPEDFATYYCQQSDSFPLTFGQGTKVEIK |
| 33 | 315 | DIVMTQSPDSLAVSLGERATINCKSSQSVLYSSNNKNYLAWYQQKPGQPPKLLIYWASFRESGVPDRFSGSGSGTDFTLTISSLQAEDVAVYYCQQYYTTPLTFGGGTKVEIK |
| 34 | 316 | DIVMTQSPDSLAVSLGERATINCKSSQSVLYSSNNKNYLAWYQQKPGQPPKLLIYWASARESGVPDRFSGSGSGTDFTLTISSLQAEDVAVYYCQQYKSAPYTFGQGTKVEIK |
| 35 | 317 | DIQMTQSPSSLSASVGDRVTITCRASQSISSYLNWYQQKPGKAPKLLIYAASSLQSGVPSRFSGSGSGTDFTLTISSLQPEDFATYYCQQSNSFPLTFGPGTKVDIK |
| 36 | 318 | DIQMTQSPSSLSASVGDRVTITCRASQSISRHLNWYQQKPGKAPKLLIYAASSLQSGVPSRFSGSGSGTDFTLTISSLQPEDFATYYCQQSYQTPLTFGGGTKVEIK |
| 37 | 319 | DIVMTQSPDSLAVSLGERATINCKSSQSVLYSSNNKNYLAWYQQKPGQPPKLLIYWASIRESGVPDRFSGSGSGTDFTLTISSLQAEDVAVYYCQQYYSSPFTFGQGTKLEIK |
| 38 | 320 | DIVMTQSPLSLPVTPGEPASISCRSSQSLLHSNGYNYLDWYLQKPGQSPQLLIYDASNLHAGVPDRFSGSGSGTDFTLKISRVEAEDVGVYYCMQALQAPVTFGQGTRLEIK |
| 39 | 321 | DIQMTQSPSSLSASVGDRVTITCQASQDISKYLNWYQQKPGKAPKLLIYAASSLQSGVPSRFSGSGSGTDFTLTISSLQPEDFATYYCQQSNSFPLTFGGGTKLEIK |
| 40 | 322 | DIQMTQSPSSLSASVGDRVTITCRASQTVRSYLNWYQQKPGKAPKLLIYAASTLQSGVPSRFSGSGSGTDFTLTISSLQPEDFATYYCQQTYRTPLTFGQGTKVEIK |

TABLE 6

| Binding Agent | SEQ ID | Light Chain Sequence |
|---|---|---|
| 1 | 325 | DIQMTQSPSSLSASVGDRVTITCQASQDISNYLNWYQQKPGKAPKLLIYAASSLQSGVPSRFSGSGSGTDFTLTISS<br>LQPEDFATYYCQQTDSIPITFGQGTKVEIKRTVAAPSVFIFPPSDEQLKSGTASVVCLLNNFYPREAKVQWKVDNA<br>LQSGNSQESVTEQDSKDSTYSLSSTLTLSKADYEKHKVYACEVTHQGLSSPVTKSFNRGEC |
| 20 | 326 | DIQMTQSPSSLSASVGDRVTITCRASQSIGSYLNWYQQKPGKAPKLLIYAASRLQSGVPSRFSGSGSGTDFTLTISS<br>LQPEDFATYYCQQSYSTPLTFGQGTKVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSPVTKSFNRGEC |
| 23a & 23b | 327 | DIQMTQSPSSLSASVGDRVTITCRASQSISSYLNWYQQKPGKAPKLLIYLASSLQSGVPSRFSGSGSGTDFTLTISSL<br>QPEDFATYYCQQSYGIPLTFGGGTKVEIKRTVAAPSVFIFPPSDEQLKSGTASVVCLLNNFYPREAKVQWKVDNA<br>LQSGNSQESVTEQDSKDSTYSLSSTLTLSKADYEKHKVYACEVTHQGLSSPVTKSFNRGEC |

TABLE 7

| Binding Agent | SEQ ID | Fc mod. | Heavy Chain Sequence |
|---|---|---|---|
| 1 | 328 | (none) | QVQLVQSGAEVKKPGASVKVSCKASGYTFTSYYMQWVRQAPGQGLEWMGWINPKSGGTNYAQKFQ<br>GRVTMTRDTSTSTVYMELSSLRSEDTAVYYCARGTYLRTGSSLSGYYYGMDVWGQGTTVTVSSASTK<br>GPSVFPLAPSSKSTSGGTAALGCLVKDYFPEPVTVSWNSGALTSGVHTFPAVLQSSGLYSLSSVVTVPSS<br>SLGTQTYICNVNHKPSNTKVDKRVEPKSCDKTHTCPPCPAPELLGGPSVFLFPPKPKDTLMISRTPEVTC<br>VVVDVSHEDPEVKFNWYVDGVEVHNAKTKPREEQYNSTYRVVSVLTVLHQDWLNGKEYKCKVSNK<br>ALPAPIEKTISKAKGQPREPQVYTLPPSREEMTKNQVSLTCLVKGFYPSDIAVEWESNGQPENNYKTTPP<br>VLDSDGSFFLYSKLTVDKSRWQQGNVFSCSVMHEALHNHYTQKSLSLSPGK |
| 1 | 329 | SE | QVQLVQSGAEVKKPGASVKVSCKASGYTFTSYYMQWVRQAPGQGLEWMGWINPKSGGTNYAQKFQ<br>GRVTMTRDTSTSTVYMELSSLRSEDTAVYYCARGTYLRTGSSLSGYYYGMDVWGQGTTVTVSSASTK<br>GPSVFPLAPSSKSTSGGTAALGCLVKDYFPEPVTVSWNSGALTSGVHTFPAVLQSSGLYSLSSVVTVPSS<br>SLGTQTYICNVNHKPSNTKVDKRVEPKSCDKTHTCPPCPAPELLGGPSVFLFPPKPKDTLMISRTPEVTC<br>VVVDVEHEDPEVKFNWYVDGVEVHNAKTKPREEQYNSTYRVVSVLTVLHQDWLNGKEYKCKVSNK<br>ALPAPIEKTISKAKGQPREPQVYTLPPSREEMTKNQVSLTCLVKGFYPSDIAVEWESNGQPENNYKTTPP<br>VLDSDGSFFLYSKLTVDKSRWQQGNVFSCSVMHEALHNHYTQKSLSLSPGK |
| 1 | 330 | ER | QVQLVQSGAEVKKPGASVKVSCKASGYTFTSYYMQWVRQAPGQGLEWMGWINPKSGGTNYAQKFQ<br>GRVTMTRDTSTSTVYMELSSLRSEDTAVYYCARGTYLRTGSSLSGYYYGMDVWGQGTTVTVSSASTK<br>GPSVFPLAPSSKSTSGGTAALGCLVKDYFPEPVTVSWNSGALTSGVHTFPAVLQSSGLYSLSSVVTVPSS<br>SLGTQTYICNVNHKPSNTKVDKRVEPKSCDKTHTCPPCPAPELLGGPSVFLFPPKPKDTLMISRTPEVTC<br>VVVDVSHEDPEVKFNWYVDGVEVHNAKTKPREEQYNSTYRVVSVLTVLHQDWLNGKEYKCKVSNK<br>ALPAPIEKTISKAKGQPRRPQVYTLPPSREEMTKNQVSLTCLVKGFYPSDIAVEWESNGQPENNYKTTPP<br>VLDSDGSFFLYSKLTVDKSRWQQGNVFSCSVMHEALHNHYTQKSLSLSPGK |
| 1 | 331 | SEER | QVQLVQSGAEVKKPGASVKVSCKASGYTFTSYYMQWVRQAPGQGLEWMGWINPKSGGTNYAQKFQ<br>GRVTMTRDTSTSTVYMELSSLRSEDTAVYYCARGTYLRTGSSLSGYYYGMDVWGQGTTVTVSSASTK<br>GPSVFPLAPSSKSTSGGTAALGCLVKDYFPEPVTVSWNSGALTSGVHTFPAVLQSSGLYSLSSVVTVPSS<br>SLGTQTYICNVNHKPSNTKVDKRVEPKSCDKTHTCPPCPAPELLGGPSVFLFPPKPKDTLMISRTPEVTC<br>VVVDVEHEDPEVKFNWYVDGVEVHNAKTKPREEQYNSTYRVVSVLTVLHQDWLNGKEYKCKVSNK<br>ALPAPIEKTISKAKGQPRRPQVYTLPPSREEMTKNQVSLTCLVKGFYPSDIAVEWESNGQPENNYKTTPP<br>VLDSDGSFFLYSKLTVDKSRWQQGNVFSCSVMHEALHNHYTQKSLSLSPGK |
| 1 | 332 | NA | QVQLVQSGAEVKKPGASVKVSCKASGYTFTSYYMQWVRQAPGQGLEWMGWINPKSGGTNYAQKFQ<br>GRVTMTRDTSTSTVYMELSSLRSEDTAVYYCARGTYLRTGSSLSGYYYGMDVWGQGTTVTVSSASTK<br>GPSVFPLAPSSKSTSGGTAALGCLVKDYFPEPVTVSWNSGALTSGVHTFPAVLQSSGLYSLSSVVTVPSS<br>SLGTQTYICNVNHKPSNTKVDKRVEPKSCDKTHTCPPCPAPELLGGPSVFLFPPKPKDTLMISRTPEVTC<br>VVVDVSHEDPEVKFNWYVDGVEVHNAKTKPREEQYASTYRVVSVLTVLHQDWLNGKEYKCKVSNK<br>ALPAPIEKTISKAKGQPREPQVYTLPPSREEMTKNQVSLTCLVKGFYPSDIAVEWESNGQPENNYKTTPP<br>VLDSDGSFFLYSKLTVDKSRWQQGNVFSCSVMHEALHNHYTQKSLSLSPGK |
| 1 | 333 | GA | QVQLVQSGAEVKKPGASVKVSCKASGYTFTSYYMQWVRQAPGQGLEWMGWINPKSGGTNYAQKFQ<br>GRVTMTRDTSTSTVYMELSSLRSEDTAVYYCARGTYLRTGSSLSGYYYGMDVWGQGTTVTVSSASTK<br>GPSVFPLAPSSKSTSGGTAALGCLVKDYFPEPVTVSWNSGALTSGVHTFPAVLQSSGLYSLSSVVTVPSS<br>SLGTQTYICNVNHKPSNTKVDKRVEPKSCDKTHTCPPCPAPELLAGPSVFLFPPKPKDTLMISRTPEVTC<br>VVVDVSHEDPEVKFNWYVDGVEVHNAKTKPREEQYNSTYRVVSVLTVLHQDWLNGKEYKCKVSNK<br>ALPAPIEKTISKAKGQPREPQVYTLPPSREEMTKNQVSLTCLVKGFYPSDIAVEWESNGQPENNYKTTPP<br>VLDSDGSFFLYSKLTVDKSRWQQGNVFSCSVMHEALHNHYTQKSLSLSPGK |
| 20 | 334 | (none) | QVQLVQSGAEVKKPGASVKVSCKASGYIFTNYWIQWVRQAPGQGLEWMGWINPNSGGTRYARNFQG<br>RVTMTRDTSTSTVYMELSSLRSEDTAVYYCARGRYYYGSGSQYHAFDIWGQGTMVTVSSASTKGPSV<br>FPLAPSSKSTSGGTAALGCLVKDYFPEPVTVSWNSGALTSGVHTFPAVLQSSGLYSLSSVVTVPSSSLGT<br>QTYICNVNHKPSNTKVDKRVEPKSCDKTHTCPPCPAPELLGGPSVFLFPPKPKDTLMISRTPEVTCVVV<br>DVSHEDPEVKFNWYVDGVEVHNAKTKPREEQYNSTYRVVSVLTVLHQDWLNGKEYKCKVSNKALPA<br>PIEKTISKAKGQPREPQVYTLPPSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPGK |

TABLE 7-continued

| Binding Agent | SEQ ID | Fc mod. | Heavy Chain Sequence |
|---|---|---|---|
| 20 | 335 | GA | QVQLVQSGAEVKKPGASVKVSCKASGYIFTNYWIQWVRQAPGQGLEWMGWINPNSGGTRYARNFQG<br>RVTMTRDTSTSTVYMELSSLRSEDTAVYYCARGRYYYGSGSQYHAFDIWGQGTMVTVSSASTKGPSV<br>FPLAPSSKSTSGGTAALGCLVKDYFPEPVTVSWNSGALTSGVHTFPAVLQSSGLYSLSSVVTVPSSSLGT<br>QTYICNVNHKPSNTKVDKVEPKSCDKTHTCPPCPAPELLAGPSVFLFPPKPKDTLMISRTPEVTCVVV<br>DVSHEDPEVKFNWYVDGVEVHNAKTKPREEQYNSTYRVVSVLTVLHQDWLNGKEYKCKVSNKALPA<br>PIEKTISKAKGQPREPQVYTLPPSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPGK |
| 20 | 336 | LALA | QVQLVQSGAEVKKPGASVKVSCKASGYIFTNYWIQWVRQAPGQGLEWMGWINPNSGGTRYARNFQG<br>RVTMTRDTSTSTVYMELSSLRSEDTAVYYCARGRYYYGSGSQYHAFDIWGQGTMVTVSSASTKGPSV<br>FPLAPSSKSTSGGTAALGCLVKDYFPEPVTVSWNSGALTSGVHTFPAVLQSSGLYSLSSVVTVPSSSLGT<br>LALAQTYICNVNHKPSNTKVDKRVEPKSCDKTHTCPPCPAPEAAGGPSVFLFPPKPKDTLMISRTPEVTCVVV<br>DVSHEDPEVKFNWYVDGVEVHNAKTKPREEQYNSTYRVVSVLTVLHQDWLNGKEYKCKVSNKALPA<br>PIEKTISKAKGQPREPQVYTLPPSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPGK |
| 20 | 337 | NA | QVQLVQSGAEVKKPGASVKVSCKASGYIFTNYWIQWVRQAPGQGLEWMGWINPNSGGTRYARNFQG<br>RVTMTRDTSTSTVYMELSSLRSEDTAVYYCARGRYYYGSGSQYHAFDIWGQGTMVTVSSASTKGPSV<br>FPLAPSSKSTSGGTAALGCLVKDYFPEPVTVSWNSGALTSGVHTFPAVLQSSGLYSLSSVVTVPSSSLGT<br>QTYICNVNHKPSNTKVDKRVEPKSCDKTHTCPPCPAPELLGGPSVFLFPPKPKDTLMISRTPEVTCVVV<br>DVSHEDPEVKFNWYVDGVEVHNAKTKPREEQYASTYRVVSVLTVLHQDWLNGKEYKCKVSNKALPA<br>PIEKTISKAKGQPREPQVYTLPPSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPGK |
| 20 | 338 | CS (IgG2) | QVQLVQSGAEVKKPGASVKVSCKASGYIFTNYWIQWVRQAPGQGLEWMGWINPNSGGTRYARNFQG<br>RVTMTRDTSTSTVYMELSSLRSEDTAVYYCARGRYYYGSGSQYHAFDIWGQGTMVTVSSASTKGPSV<br>FPLAPCSRSTSESTAALGCLVKDYFPEPVTVSWNSGALTSGVHTFPAVLQSSGLYSLSSVVTVPSSNFGT<br>QTYTCNVDHKPSNTKVDKTVERKSCVECPPCPAPPVAGPSVFLFPPKPKDTLMISRTPEVTCVVVDVSH<br>EDPEVQFNWYVDGVEVHNAKTKPREEQFNSTFRVVSVLTVVHQDWLNGKEYKCKVSNKGLPAPIEKT<br>ISKTKGQPREPQVYTLPPSREEMTKNQVSLTCLVKGFYPSDIAVEWESNGQPENNYKTTPPMLDSDGSF<br>FLYSKLTVDKSRWQQGNVFSCSVMHEALHNHYTQKSLSLSPGK |
| 20 | 339 | ER | QVQLVQSGAEVKKPGASVKVSCKASGYIFTNYWIQWVRQAPGQGLEWMGWINPNSGGTRYARNFQG<br>RVTMTRDTSTSTVYMELSSLRSEDTAVYYCARGRYYYGSGSQYHAFDIWGQGTMVTVSSASTKGPSV<br>FPLAPSSKSTSGGTAALGCLVKDYFPEPVTVSWNSGALTSGVHTFPAVLQSSGLYSLSSVVTVPSSSLGT<br>QTYICNVNHKPSNTKVDKRVEPKSCDKTHTCPPCPAPELLGGPSVFLFPPKPKDTLMISRTPEVTCVVV<br>DVSHEDPEVKFNWYVDGVEVHNAKTKPREEQYNSTYRVVSVLTVLHQDWLNGKEYKCKVSNKALPA<br>PIEKTISKAKGQPRRPQVYTLPPSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPGK |
| 23a | 340 | (none) | EVQLLESGGGLVQPGGSLRLSCAASGFTFSSYSMNWVRQAPGKGLEWVAVISYDGRIKDYADSVKGR<br>FTISRDNSKNTLYLQMNSLRAEDTAVYYCARVRGFSFWFDPWGQGTLVTVSSASTKGPSVFPLAPSSKS<br>TSGGTAALGCLVKDYFPEPVTVSWNSGALTSGVHTFPAVLQSSGLYSLSSVVTVPSSSLGTQTYICNVN<br>HKPSNTKVDKRVEPKSCDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSNKALPAPIEKTISKA<br>KGQPREPQVYTLPPSREEMTKNQVSLTCLVKGFYPSDIAVEWESNGQPENNYKTTPPVLDSDGSFFLYS<br>KLTVDKSRWQQGNVFSCSVMHEALHNHYTQKSLSLSPGK |
| 23a | 341 | ER | EVQLLESGGGLVQPGGSLRLSCAASGFTFSSYSMNWVRQAPGKGLEWVAVISYDGRIKDYADSVKGR<br>FTISRDNSKNTLYLQMNSLRAEDTAVYYCARVRGFSFWFDPWGQGTLVTVSSASTKGPSVFPLAPSSKS<br>TSGGTAALGCLVKDYFPEPVTVSWNSGALTSGVHTFPAVLQSSGLYSLSSVVTVPSSSLGTQTYICNVN<br>HKPSNTKVDKRVEPKSCDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSNKALPAPIEKTISKA<br>KGQPRRPQVYTLPPSREEMTKNQVSLTCLVKGFYPSDIAVEWESNGQPENNYKTTPPVLDSDGSFFLYS<br>KLTVDKSRWQQGNVFSCSVMHEALHNHYTQKSLSLSPGK |
| 23a | 342 | GA | EVQLLESGGGLVQPGGSLRLSCAASGFTFSSYSMNWVRQAPGKGLEWVAVISYDGRIKDYADSVKGR<br>FTISRDNSKNTLYLQMNSLRAEDTAVYYCARVRGFSFWFDPWGQGTLVTVSSASTKGPSVFPLAPSSKS<br>TSGGTAALGCLVKDYFPEPVTVSWNSGALTSGVHTFPAVLQSSGLYSLSSVVTVPSSSLGTQTYICNVN<br>HKPSNTKVDKRVEPKSCDKTHTCPPCPAPELLAGPSVFLFPPKPKDTLMISRTPEVTCVVVDVSHEDPE<br>VKFNWYVDGVEVHNAKTKPREEQYNSTYRVVSVLTVLHQDWLNGKEYKCKVSNKALPAPIEKTISKA<br>KGQPREPQVYTLPPSREEMTKNQVSLTCLVKGFYPSDIAVEWESNGQPENNYKTTPPVLDSDGSFFLYS<br>KLTVDKSRWQQGNVFSCSVMHEALHNHYTQKSLSLSPGK |
| 23a | 343 | CS | EVQLLESGGGLVQPGGSLRLSCAASGFTFSSYSMNWVRQAPGKGLEWVAVISYDGRIKDYADSVKGR<br>FTISRDNSKNTLYLQMNSLRAEDTAVYYCARVRGFSFWFDPWGQGTLVTVSSASTKGPSVFPLAPCSR<br>STSESTAALGCLVKDYFPEPVTVSWNSGALTSGVHTFPAVLQSSGLYSLSSVVTVPSSNFGTQTYTCNV<br>DHKPSNTKVDKTVERKSCVECPPCPAPPVAGPSVFLFPPKPKDTLMISRTPEVTCVVVDVSHEDPEVQF<br>NWYVDGVEVHNAKTKPREEQFNSTFRVVSVLTVVHQDWLNGKEYKCKVSNKGLPAPIEKTISKTKGQ<br>PREPQVYTLPPSREEMTKNQVSLTCLVKGFYPSDIAVEWESNGQPENNYKTTPPMLDSDGSFFLYSKLT<br>VDKSRWQQGNVFSCSVMHEALHNHYTQKSLSLSPGK |
| 23a | 344 | LALA | EVQLLESGGGLVQPGGSLRLSCAASGFTFSSYSMNWVRQAPGKGLEWVAVISYDGRIKDYADSVKGR<br>FTISRDNSKNTLYLQMNSLRAEDTAVYYCARVRGFSFWFDPWGQGTLVTVSSASTKGPSVFPLAPSSKS<br>TSGGTAALGCLVKDYFPEPVTVSWNSGALTSGVHTFPAVLQSSGLYSLSSVVTVPSSSLGTQTYICNVN<br>HKPSNTKVDKRVEPKSCDKTHTCPPCPAPEAAGGPSVFLFPPKPKDTLMISRTPEVTCVVVDVSHEDPE |

TABLE 7-continued

| Binding Agent | SEQ ID | Fc mod. | Heavy Chain Sequence |
|---|---|---|---|
| | | | VKFNWYVDGVEVHNAKTKPREEQYNSTYRVVSVLTVLHQDWLNGKEYKCKVSNKALPAPIEKTISKA<br>KGQPREPQVYTLPPSREEMTKNQVSLTCLVKGFYPSDIAVEWESNGQPENNYKTTPPVLDSDGSFFLYS<br>KLTVDKSRWQQGNVFSCSVMHEALHNHYTQKSLSLSPGK |
| 23b | 345 | (none) | EVQLLESGGGLVQPGGSLRLSCAASGFTFSSYSMNWVRQAPGKGLEWVAVISYDGRIKDYADSVKGR<br>FTISRDNSKNTLYLQMNSLRAEDTAVYYCARVRGFSFWFEPWGQGTLVTVSSASTKGPSVFPLAPSSKS<br>TSGGTAALGCLVKDYFPEPVTVSWNSGALTSGVHTFPAVLQSSGLYSLSSVVTVPSSSLGTQTYICNVN<br>HKPSNTKVDKRVEPKSCDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSNKALPAPIEKTISKA<br>KGQPREPQVYTLPPSREEMTKNQVSLTCLVKGFYPSDIAVEWESNGQPENNYKTTPPVLDSDGSFFLYS<br>KLTVDKSRWQQGNVFSCSVMHEALHNHYTQKSLSLSPGK |

As mentioned above, the binding agent can comprise an Ig heavy and/or light chain variable region with at least about 90% identity (e.g. at least about 91%, at least about 92%, at least about 93%, at least about 94%, at least about 95%, at least about 96%, at least about 97%, at least about 98%, or at least about 99% identity) to a specific heavy or light chain variable region sequence provided herein. Similarly, the CDRs of the Ig heavy and/or light chain variable region can have at least about 90% identity (e.g. at least about 91%, at least about 92%, at least about 93%, at least about 94%, at least about 95%, at least about 96%, at least about 97%, at least about 98%, or at least about 99% identity) to a specific CDR sequence provided herein. Thus, the Ig heavy and light chain variable region or CDR sequence can comprise at least one (e.g., 1 or more, 2 or more, 3 or more, 4 or more, 5 or more, 6 or more, 7 or more, 8 or more, 9 or more, or 10 or more, etc., as applicable based on the length of the sequence) amino acid modification (e.g., substitution, addition, or deletion) as compared to the specific sequences provided herein, provided the binding agent maintains the ability to specifically bind Dectin-2, optionally wherein the binding agent maintains the affinity of a binding agent with the specified sequences and/or competes with a binding agent having the specified sequences for binding to Dectin-2.

The amino acids of the sequences provided can be substituted with any other amino acid. Amino acids include naturally-occurring α-amino acids and their stereoisomers, as well as non-naturally occurring amino acids and their stereoisomers. "Stereoisomers" of a given amino acid refer to isomers having the same molecular formula and intramolecular bonds but different three-dimensional arrangements of bonds and atoms (e.g., an L-amino acid and the corresponding D-amino acid). The amino acids can be glycosylated (e.g., N-linked glycans, O-linked glycans, phosphoglycans, C-linked glycans, or glypiation) or deglycosylated.

Naturally-occurring amino acids are those encoded by the genetic code, as well as those amino acids that are later modified, e.g., hydroxyproline, γ-carboxyglutamate, and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Non-naturally occurring amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, and methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either the commonly known three letter symbols or by the one-letter symbols recommended by the IUPAC-IUB Biochemical Nomenclature Commission.

The amino acid substitution can be conservative, semi-conservative, or non-conservative with respect to the basic properties of the original amino acid residue. A "conservative" substitution refers to the replacement of one amino acid by another amino acid with a common property. A functional way to define common properties between individual amino acids is to analyze the normalized frequencies of amino acid changes between corresponding proteins of homologous organisms (Schulz and Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (D or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free —NH$_2$ can be maintained.

"Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

In addition, one or more amino acids can be inserted into the aforementioned immunoglobulin heavy or light chain variable region polypeptides. Any number of any suitable amino acids can be inserted into the amino acid sequence of the immunoglobulin heavy or light chain variable region polypeptide. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the immunoglobulin heavy or light chain variable region polypeptide. Preferably, 1-10 amino acids (e.g., 1, 2, 3, 4, 5, 6, 7, 8, 9, or 10 amino acids) are inserted into the amino acid sequence of the immunoglobulin heavy or light chain variable region polypeptide. In this respect, the amino acid(s) can be inserted into any one of the aforementioned immunoglobulin heavy or light chain variable region polypeptides in any suitable location. In some embodiments, the amino acid(s) are inserted into a CDR (e.g., CDR1, CDR2, or CDR3) of the immunoglobulin heavy or light chain variable region polypeptide; in other embodiments, the amino acids are inserted into a framework region.

Further provided is a Dectin-2 binding agent (e.g., antibody or antibody fragment) that competes with a Dectin-2 binding agent (e.g., antibody or antibody fragment) having an immunoglobulin heavy and light chain variable region specifically provided herein (e.g., one of the binding agents provided herein), and preferably retains the biological activity of the Dectin-2 binding agent.

The "biological activity" of a Dectin-2 binding agent refers to, for example, binding affinity for Dectin-2 or a particular Dectin-2 epitope, pharmacokinetics, and cross-reactivity (e.g., with non-human homologs or orthologs of the Dectin-2 protein, or with other proteins or tissues). In some embodiments, the biological activity of the Dectin-2 binding agent includes the ability to increase Dectin-2 activity in vivo and/or in vitro. Examples of Dectin-2 activity include increased or enhanced expression and/or production of pro-inflammatory cytokines, increased expression of costimulatory molecules, such as CD40, CD86, and major histocompatibility complex (MHC) molecules, and increased phagocytosis. Examples of pro-inflammatory cytokines include Tumor Necrosis Factor (TNF) alpha, IL-1β, IL-2, IL-6, IL-23p19, IFNγ, IL-12p40, and IL-12p70.

The term "increase" or "enhance" as used in reference to Dectin-2 activity (e.g., Dectin-2 mediated signaling) means to increase or enhance such binding or signaling in any way and to any degree (e.g., act as an agonist). In some embodiments, Dectin-2 mediated signaling is increased sufficiently to reduce or alleviate any symptom of a disease or condition associated with deficient Dectin-2 activity, or which benefits from enhanced Dectin-2 activity, or to reverse, slow, or stop the progression or severity of such a disease or condition. The Dectin-2 binding agent of the invention preferably increases the activity of Dectin-2 by at least about 20%, about 30%, about 40%, about 50%, about 60%, about 70%, about 80%, about 90%, about 95%, about 100%, about 150%, about 200%, about 300%, or a range defined by any two of the foregoing values, as compared to the activity of Dectin-2 in Dectin-2 expressing cells in the absence of the Dectin-2 agent.

Other biological properties or characteristics of an antigen-binding agent recognized in the art include, for example, avidity, selectivity, solubility, folding, immunotoxicity, expression, and formulation. The aforementioned properties or characteristics can be observed, measured, and/or assessed using standard techniques including, but not limited to, ELISA, competitive ELISA, surface plasmon resonance analysis (BIACORE™), or KINEXA™, in vitro or in vivo neutralization assays, receptor-ligand binding assays, cytokine or growth factor production and/or secretion assays, and signal transduction and immunohistochemistry assays.

In some embodiments, the Dectin-2 binding agent (e.g., antibody or antibody fragment) increases or enhances Dectin-2 expression in cells of myeloid lineage, such as, for example, monocytes, macrophages, and dendritic cells, in comparison to Dectin-2 expression in cells of myeloid lineage not exposed to the Dectin-2 binding agent. This increase or enhancement in Dectin-2 expression can lead to an increased innate immune response. Without wishing to be bound by any particular theory, activation of the Dectin-2 signaling pathway is known to, for example, increase phagocytic activity and to activate MAPK and NF-κB signaling pathways, leading to the production of pro-inflammatory cytokines such as, for instance, TNFα, IL-1β, IL-2, IL-6, IL-23p19, IFNγ, IL-12p40, and IL-12p70.

In some embodiments, the Dectin-2 binding agent (e.g., antibody or antibody fragment) exhibits antibody dependent cell-mediated cytotoxicity (ADCC). ADCC is a mechanism of cell-mediated immune defense whereby an effector cell of the immune system lyses a target cell whose membrane-surface antigens have been bound by specific antibodies. ADCC is independent of the immune complement system that also lyses targets but does not require any other cell and is part of the adaptive immune response.

In some embodiments, the Dectin-2 binding agent (e.g., antibody or antibody fragment) promotes antibody dependent cell-mediated phagocytosis (ADCP). ADCP is a cellular process by which effector cells with phagocytic potential, such as monocytes and macrophages, can internalize target cells. Once phagocytosed, the target cell resides in a phagosome, which fuses with a lysosome to begin degradation of the target cell via an oxygen-dependent or independent mechanism. This function is dependent on opsonization, or identification of the target cell with a binding agent, which then also serves as a bridge between the target cell and the phagocytic cell. Mechanistically, the binding agent binds its cognate antigen on the target cell through its antigen recognition domain, and then recruits the phagocytic cell to the target with its Fc region. Once bound to the Fc receptor of the phagocytic cell, the target cell is ingested and degraded. This process also leads to the production of soluble factors by the effector cells that help initiate and drive the immune response.

In some embodiments, the Dectin-2 binding agent (e.g., antibody or antibody fragment) exhibits complement dependent cytotoxicity (CDC). CDC is an effector function of IgG and IgM antibodies. When the binding agents are bound to surface antigen, the classical complement pathway is triggered, resulting in formation of a membrane attack complex (MAC) and target cell lysis.

In some embodiments, the binding agents comprise an Fc region containing one or more modifications (e.g., amino acid insertion, deletion, and/or substitution) in the Fc region that results in modulated binding (e.g., increased binding or decreased binding) to one or more Fc receptors (e.g., FcγRI (CD64), FcγRIIA (CD32A), FcγRIIB (CD32B), FcγRIIIA (CD16a), and/or FcγRIIIB (CD16b)) as compared to a binding agent or antibody with the native Fc region lacking the mutation. In some embodiments, the binding agents contain one or more modifications (e.g., amino acid insertion, deletion, and/or substitution) in the Fc region that reduce the binding of the Fc region to FcγRIIB In some embodiments, the binding agents contain one or more modifications (e.g., amino acid insertion, deletion, and/or substitution) in the Fc region of the antibody that reduce the binding to FcγRIIB while maintaining the same binding or having increased binding to FcγRI (CD64), FcγRIIA (CD32A), and/or FcRγIIIA (CD16a) as compared to a binding agent or antibody with a native Fc region lacking the mutation. In some embodiments, the binding agents contain one of more modifications in the Fc region that increase the binding of the Fc region to FcγRIIB In some embodiments, the modifications substantially reduce or eliminate antibody effector functions.

The Fc region mutations can be in a CH2 domain, a CH3 domain, or a combination thereof. A "native Fc region" is synonymous with a "wild-type Fc region" and comprises an amino acid sequence that is identical to the amino acid sequence of an Fc region found in nature or identical to the amino acid sequence of the Fc region found in a native antibody. Native human Fc regions include a native sequence human IgG1 Fc region, native sequence human IgG2 Fc region, native sequence human IgG3 Fc region, and native sequence human IgG4 Fc region, as well as naturally occurring variants thereof. Native sequence Fc includes the various allotypes of Fcs (see, e.g., Jefferis et al., *mAbs,* 1(4): 332-338 (2009)).

In some embodiments, the Dectin-2 binding agent comprises an IgG (e.g., IgG1) Fc region or at least the CH2 domain thereof (e.g., a chimeric Fc comprising CH1, CH2, and CH3 regions of IgG1, but hinge region from a different Ig, such as IgG2). In some embodiments, the Dectin-2 binding agent comprises one or more of the following mutations or groups of mutations: SD (S239D), SDIE (S239D/I332E), SE (S267E), SEER (S267E/E345R), SELF (S267E/L328F), SDIEAL (S239D/I332E/A330L), GA (G236A), ALIE (A330L/I332E), GASDALIE (G236A/S239D/A330L/I332E), V9 (G237D/P238D/P271G/A330R), LALA (L234A/L235A), CS (C219S), NA (N297A), and V11 (G237D/P238D/H268D/P271G/A330R), and/or one or more mutations at the following amino acids: E345R, E233, G237, P238, H268, P271, N297, L328 and A330. All numbering refers to the EU numbering of human IgG (e.g., IgG1); however, the same mutations at corresponding positions of a different Ig (e.g., a chimeric Ig) can be used. In an embodiment, the mutation is SD. In an embodiment, the mutation is SDIE. In an embodiment, the mutation is SE. In an embodiment, the mutation is SELF. In an embodiment, the mutation is SDIEAL. In an embodiment, the mutation is GA. In an embodiment, the mutation is ALIE. In an embodiment, the mutation is GASDALIE. In an embodiment, the mutation is V9. In an embodiment, the mutation is LALA. In an embodiment, the mutation is CS. In an embodiment, the mutation is V11. In an embodiment, the mutation is E345R. In an embodiment, the mutation is NA. In an embodiment, the mutation is SEER. In an embodiment, the Dectin-2 binding agent comprises an Fc region with G236A, LALA and/or CS mutations, optionally wherein the Fc region is afucosylated (i.e., non-fucosylated). In some embodiments, the Dectin-2 binding agent comprises an Fc region with one or more of the above-listed mutations or groups of mutations, wherein the Fc region is afucosylated. Additional Fc region modifications for modulating Fc receptor binding are described in, for example, U.S. Patent Application Publication 2016/0145350 and U.S. Pat. Nos. 7,416,726 and 5,624,821, which are hereby incorporated by reference in their entireties herein.

In an embodiment, the Dectin-2 binding agent is Binding Agent 1 disclosed herein (VH and VL regions respectively SEQ ID NOs: 243 and 283). In an embodiment, the Dectin-2 binding agent is Binding Agent 1 further comprising an Fc region. In another embodiment, the Dectin-2 binding agent is Binding Agent 1, wherein the Fc region is IgG1. In another embodiment, the Dectin-2 binding agent is Binding Agent 1, wherein the Fc region is IgG2. In another embodiment, the Dectin-2 binding agent is Binding Agent 1, wherein the Fc region is IgG1, and comprises the SE mutation. In another embodiment, the Dectin-2 binding agent is Binding Agent 1, wherein the Fc region is IgG1, and comprises the E345R mutation. In another embodiment, the Dectin-2 binding agent is Binding Agent 1, wherein the Fc region is IgG1, and comprises the SEER mutation. In another embodiment, the Dectin-2 binding agent is Binding Agent 1, wherein the Fc region is IgG1, and comprises the NA mutation. In another embodiment, the Dectin-2 binding agent is Binding Agent 1, wherein the Fc region is IgG1, and comprises the GA mutation. In another embodiment, the Dectin-2 binding agent is Binding Agent 1, wherein the Fc region is IgG1, comprises the GA mutation, and is also afucosylated. In another embodiment, the Dectin-2 binding agent is Binding Agent 1, wherein the Fc region is IgG1, and is afucosylated.

In an embodiment, the Dectin-2 binding agent is Binding Agent 20 disclosed herein (VH and VL regions respectively SEQ ID NOs: 261 and 302). In an embodiment, the Dectin-2 binding agent is Binding Agent 20 further comprising an Fc region. In another embodiment, the Dectin-2 binding agent is Binding Agent 20, wherein the Fc region is IgG1. In another embodiment, the Dectin-2 binding agent is Binding Agent 20, wherein the Fc region is IgG2. In another embodiment, the Dectin-2 binding agent is Binding Agent 20, wherein the Fc region is IgG1, and is afucosylated. In another embodiment, the Dectin-2 binding agent is Binding Agent 20, wherein the Fc region is IgG1, and comprises the GA mutation. In another embodiment, the Dectin-2 binding agent is Binding Agent 20, wherein the Fc region is IgG1, and comprises the LALA mutation. In another embodiment, the Dectin-2 binding agent is Binding Agent 20, wherein the Fc region is IgG1, and comprises the NA mutation. In another embodiment, the Dectin-2 binding agent is Binding Agent 20, wherein the Fc region is IgG1, and comprises the CS mutation. In another embodiment, the Dectin-2 binding agent is Binding Agent 20, wherein the Fc region is IgG2, and comprises the CS mutation. In another embodiment, the Dectin-2 binding agent is Binding Agent 20, wherein the Fc region comprises the E345R mutation. In another embodiment, the Dectin-2 binding agent is Binding Agent 20, wherein the Fc region is IgG1, comprises the GA mutation, and is also afucosylated.

In an embodiment, the Dectin-2 binding agent is Binding Agent 23a disclosed herein (VH and VL regions respectively SEQ ID NOs: 265 and 305). In an embodiment, the Dectin-2 binding agent is Binding Agent 23a further comprising an Fc region. In another embodiment, the Dectin-2 binding agent is Binding Agent 23a, wherein the Fc region is IgG1. In another embodiment, the Dectin-2 binding agent is Binding Agent 23a, wherein the Fc region is IgG2. In another embodiment, the Dectin-2 binding agent is Binding Agent 23a, wherein the Fc region is IgG1, and is afucosylated. In another embodiment, the Dectin-2 binding agent is Binding Agent 23a, wherein the Fc region is IgG1, and comprises the E345R mutation. In another embodiment, the Dectin-2 binding agent is Binding Agent 23a, wherein the Fc region is IgG1, and comprises the GA mutation. In another embodiment, the Dectin-2 binding agent is Binding Agent 23a, wherein the Fc region comprises the NA mutation. In another embodiment, the Dectin-2 binding agent is Binding Agent 23a, wherein the Fc region is IgG1, comprises the GA mutation, and is also afucosylated. In another embodiment, the Dectin-2 binding agent is Binding Agent 23a, wherein the Fc region is IgG2, and comprises the CS mutation. In another embodiment, the Dectin-2 binding agent is Binding Agent 23a, wherein the Fc region comprises the LALA mutation. In another embodiment, the Dectin-2 binding agent is Binding Agent 23b disclosed herein (VH and VL regions respectively SEQ ID NOs: 324 and 305), wherein the Fc region is IgG1, and wherein the heavy chain variable region includes a D101E mutation (Kabat numbering).

In some embodiments, the Fc region of the binding agents are modified to have an altered glycosylation pattern of the Fc region compared to the native non-modified Fc region.

Human immunoglobulin is glycosylated at the Asn297 residue in the Cγ2 domain of each heavy chain. This N-linked oligosaccharide is composed of a core heptasaccharide, N-acetylglucosamine4Mannose3 (GlcNAc4Man3). Removal of the heptasaccharide with endoglycosidase or PNGase F is known to lead to conformational changes in the Fc region, which can significantly reduce binding affinity to activating FcγR and lead to decreased effector function. The core heptasaccharide is often decorated with galactose, bisecting GlcNAc, fucose, or sialic acid, which differentially impacts Fc binding to activating and inhibitory FcγR. Additionally, it has been demonstrated that α2,6-sialyation enhances anti-inflammatory activity in vivo, while defucosylation leads to improved FcγRIIIa binding and a 10-fold increase in antibody-dependent cellular cytotoxicity and antibody-dependent phagocytosis. Specific glycosylation patterns, therefore, can be used to control inflammatory effector functions.

In some embodiments, the modification to alter the glycosylation pattern is a mutation. For example, a substitution at Asn297. In some embodiments, Asn297 is mutated to glutamine (N297Q). Methods for controlling immune response with antibodies that modulate FcγR-regulated signaling are described, for example, in U.S. Pat. No. 7,416,726 and U.S. Patent Application Publications 2007/0014795 and 2008/0286819, which are hereby incorporated by reference in their entireties.

In some embodiments, the binding agents are modified to contain an engineered Fab region with a non-naturally occurring glycosylation pattern. For example, hybridomas can be genetically engineered to secrete afucosylated mAb, desialylated mAb or deglycosylated Fc with specific mutations that enable increased FcRγIIIa binding and effector function. In some embodiments, the binding agents are engineered to be afucosylated.

In some embodiments, the entire Fc region is exchanged with a different Fc region, so that the Fab region is conjugated to a non-native Fc region. For example, the Fab region of atezolizumab, which normally comprises an IgG1 Fc region, can be conjugated to IgG2, IgG3, IgG4, or IgA, or the Fab region of nivolumab, which normally comprises an IgG4 Fc region, can be conjugated to IgG1, IgG2, IgG3, IgA1, or IgG2. In some embodiments, the Fc modified binding agent with a non-native Fc domain also comprises one or more additional amino acid modification, such as the S228P mutation within the IgG4 Fc, that modulate the stability of the Fc domain described. In some embodiments, the Fc modified binding agent with a non-native Fc domain also comprises one or more amino acid modifications described herein that modulate Fc binding to FcR.

In some embodiments, the modifications that modulate the binding of the Fc region to FcR do not alter the binding of the Fab region to its antigen when compared to the non-modified Fab. In other embodiments, the modifications that modulate the binding of the Fc region to FcR also increase the binding of the Fab region to its antigen when compared to the non-modified Fab.

In some embodiments, the Fc region is modified by attachment or inclusion of a transforming growth factor beta 1 (TGFβ1) receptor, or a fragment thereof, that is capable of binding TGFβ1. For example, the receptor can be TGFβ receptor II (TGFβRII) (see U.S. Pat. No. 9,676,863, incorporated herein in its entirety). In some embodiments, the TGFβ receptor is a human TGFβ receptor. In some embodiments, the Fc region (e.g., IgG) has a C-terminal fusion to a TGFβ receptor (e.g., TGFβRII) extracellular domain (ECD; e.g., amino acids 24-159 of SEQ ID NO: 9 of U.S. Pat. No. 9,676,863). An "Fc linker" may be used to attach the TGFβR extracellular domain to the Fc region (e.g., IgG), for example, a $G_4S_4G$ linker. The Fc linker may be a short, flexible peptide that allows for the proper three-dimensional folding of the molecule while maintaining the binding-specificity to the targets. In some embodiments, the N-terminus of the TGFβ receptor is fused to the Fc region (with or without an Fc linker). In some embodiments, the C-terminus of the immunoglobulin heavy chain is fused to the TGFβ receptor (with or without an Fc linker), such as at the N-terminus of the TGFβ receptor. In some embodiments, the C-terminal lysine residue of the antibody heavy chain is mutated to alanine.

The Dectin-2 binding agent can have any suitable affinity to a Dectin-2 protein or an epitope thereof. The term "affinity" refers to the equilibrium constant for the reversible binding of two agents and is expressed as the dissociation constant ($K_D$). Affinity of a binding agent to a ligand, such as affinity of an antibody for an epitope, can be, for example, from about 1 picomolar (pM) to about 1 micromolar (μM) (e.g., from about 1 picomolar (pM) to about 1 nanomolar (nM), or from about 1 nM to about 1 micromolar (μM)). In one embodiment, the Dectin-2 binding agent can bind to a human Dectin-2 protein with a $K_D$ less than or equal to 1 micromolar (e.g., 0.9 μM, 0.8 μM, 0.7 μM, 0.6 μM, 0.5 μM, 0.4 μM, 0.3 μM, 0.2 μM, 0.1 μM, 0.05 μM, 0.025 μM, 0.01 μM, 0.001 μM, or a range defined by any two of the foregoing values). In one embodiment, the Dectin-2 binding agent can bind to a human Dectin-2 protein with a $K_D$ less than or equal to 200 nanomolar (e.g., 190 nM, 175 nM, 150 nM, 125 nM, 110 nM, 100 nM, 90 nM, 80 nM, 75 nM, 60 nM, 50 nM, 40 nM, 30 nM, 25 nM, 20 nM, 15 nM, 10 nM, 5 nM, 1 nM, or a range defined by any two of the foregoing values). In one embodiment, the Dectin-2 binding agent can bind to a human Dectin-2 protein with a $K_D$ less than or equal to 1 nanomolar (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values). In another embodiment, the Dectin-2 binding agent can bind to human Dectin-2 with a $K_D$ less than or equal to 200 pM (e.g., 190 pM, 175 pM, 150 pM, 125 pM, 110 pM, 100 pM, 90 pM, 80 pM, 75 pM, 60 pM, 50 pM, 40 pM, 30 pM, 25 pM, 20 pM, 15 pM, 10 pM, 5 pM, 1 pM, or a range defined by any two of the foregoing values).

In some embodiments, the Dectin-2 binding agent also binds to a non-human species of Dectin-2 protein that is useful for development in animal models (e.g., tox screens and the like). In some embodiments, the Dectin-2 binding agent has an affinity for human Dectin-2 as described above, and also has an affinity for cynomolgus monkey or rat Dectin-2 that is within the above-mentioned ranges of affinity for human Dectin-2.

Immunoglobulin affinity for an antigen or epitope of interest can be measured using any art-recognized assay. Such methods include, for example, fluorescence activated cell sorting (FACS), separable beads (e.g., magnetic beads), surface plasmon resonance (SPR), solution phase competition (KINEXA™), antigen panning, and/or ELISA (see, Janeway et al. (eds.), *Immunobiology,* 9th Ed., Garland Publishing, New York, N.Y. (2017)). In some embodiments, the binding agent (e.g., an antibody or antigen-binding antibody fragment) has an affinity to human Dectin-2 as described above as determined by SPR or as determined by solution-phase competition assay. In some embodiments, the binding agent (e.g., an antibody or antigen-binding antibody fragment) has an affinity to human Dectin-2 as described above as determined by ELISA or as determined by FACs.

Nucleic Acids

The invention also provides nucleic acids that encode the immunoglobulin heavy chain polypeptide and/or the immunoglobulin light chain polypeptide of the Dectin-2 binding agent.

The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

The nucleic acid can be part of a vector. Thus, also provided is a vector comprising one or more nucleic acid sequences encoding the immunoglobulin heavy chain polypeptide, the immunoglobulin light chain polypeptide, or both, of the Dectin-2 binding agent. Any type of vector can be used, particularly an expression vector useful for expressing the polypeptides in a cell. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual,* 3rd edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)).

The vector preferably comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the American Type Culture Collection (ATCC) as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include, for example, the Tet system (U.S. Pat. Nos. 5,464,758 and 5,814,618), the Ecdysone inducible system (No et al., *Proc. Natl. Acad. Sci.,* 93: 3346-3351 (1996)), the T-REX™ system (Invitrogen, Carlsbad, Calif.), LACSWITCH™ system (Stratagene, San Diego, Calif.), and the Cre-ERT tamoxifen inducible recombinase system (Indra et al., *Nuc. Acid. Res.,* 27: 4324-4327 (1999); *Nuc. Acid. Res.,* 28: e99 (2000); U.S. Pat. No. 7,112,715; and Kramer & Fussenegger, *Methods Mol. Biol.,* 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences.

The vector also can comprise a "selectable marker gene." The term "selectable marker gene," as used herein, refers to a nucleic acid sequence that allow cells expressing the nucleic acid sequence to be specifically selected for or against, in the presence of a corresponding selective agent. Suitable selectable marker genes are known in the art and described in, e.g., International Patent Application Publications WO 1992/008796 and WO 1994/028143; Wigler et al., *Proc. Natl. Acad. Sci. USA*, 77: 3567-3570 (1980); O'Hare et al., *Proc. Natl. Acad. Sci. USA*, 78: 1527-1531 (1981); Mulligan & Berg, *Proc. Natl. Acad. Sci. USA*, 78: 2072-2076 (1981); Colberre-Garapin et al., *J. Mol. Biol.*, 150: 1-14 (1981); Santerre et al., *Gene*, 30: 147-156 (1984); Kent et al., *Science*, 237: 901-903 (1987); Wigler et al., *Cell*, 11: 223-232 (1977); Szybalska & Szybalski, *Proc. Natl. Acad. Sci. USA*, 48: 2026-2034 (1962); Lowy et al., *Cell*, 22: 817-823 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy*, 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), UCOE from Millipore (Billerica, Mass.), and pCI or pFN10A (ACT) FLEXI™ from Promega (Madison, Wis.).

Viral vectors also can be used. Representative commercially available viral expression vectors include, but are not limited to, the adenovirus-based Per.C6 system available from Crucell, Inc. (Leiden, The Netherlands), the lentiviral-based pLP1 from Invitrogen (Carlsbad, Calif.), and the retroviral vectors pFB-ERV plus pCFB-EGSH from Stratagene (La Jolla, Calif.).

Cells

Nucleic acid sequences encoding the heavy and light chain immunoglobulin sequences can be provided to a cell on the same vector (i.e., in cis). A unidirectional promoter can be used to control expression of each nucleic acid sequence. In another embodiment, a combination of bidirectional and unidirectional promoters can be used to control expression of multiple nucleic acid sequences. Nucleic acid sequences encoding the inventive amino acid sequences alternatively can be provided to the population of cells on separate vectors (i.e., in trans). Each of the nucleic acid sequences in each of the separate vectors can comprise the same or different expression control sequences. The separate vectors can be provided to cells simultaneously or sequentially.

The vector(s) comprising the nucleic acid(s) encoding the inventive amino acid sequences can be introduced into a host cell that is capable of expressing the polypeptides encoded thereby, including any suitable prokaryotic or eukaryotic cell. As such, the invention provides an in vitro (isolated) cell or cell line comprising the inventive vector, which expresses the immunoglobulin heavy and light chain polypeptides. Preferred host cells are those that can be easily and reliably grown, have reasonably fast growth rates, have well characterized expression systems, and can be transformed or transfected easily and efficiently.

Examples of suitable prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella*, and *Erwinia*. Particularly useful prokaryotic cells include the various strains of *Escherichia coli* (e.g., K12, HB101 (ATCC No. 33694), DH5a, DH10, MC1061 (ATCC No. 53338), and CC102).

Preferably, the vector is introduced into a eukaryotic cell. Suitable eukaryotic cells are known in the art and include, for example, yeast cells, insect cells, and mammalian cells. Examples of suitable yeast cells include those from the genera *Kluyveromyces, Pichia, Rhinosporidium, Saccharomyces*, and *Schizosaccharomyces*. Preferred yeast cells include, for example, *Saccharomyces cerivisae* and *Pichia pastoris*.

Suitable insect cells are described in, for example, Kitts et al., *Biotechniques*, 14: 810-817 (1993); Lucklow, *Curr. Opin. Biotechnol.*, 4: 564-572 (1993); and Lucklow et al., *J. Virol.*, 67: 4566-4579 (1993). Preferred insect cells include Sf-9 and HI5 (Invitrogen, Carlsbad, Calif.).

Preferably, mammalian cells are utilized in the invention. A number of suitable mammalian host cells are known in the art, and many are available from ATCC. Examples of suitable mammalian cells include, but are not limited to, Chinese hamster ovary cells (CHO) cells, such as CHO-K1 cells (ATCC No. CCL61), CHO DHFR-cells (Urlaub et al., *Proc. Natl. Acad. Sci. USA*, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Suitable cell lines also include hybridomas. Methods for selecting suitable mammalian host cells and methods for transformation, culture, amplification, screening, and purification of cells are known in the art.

The mammalian cell can be a human cell. For example, the mammalian cell can be a human lymphoid or lymphoid derived cell line, such as a cell line of pre-B lymphocyte origin. Examples of human lymphoid cells lines include, without limitation, RAMOS (CRL-1596), Daudi (CCL-213), EB-3 (CCL-85), DT40 (CRL-2111), 18-81 (Jack et al., *Proc. Natl. Acad. Sci. USA,* 85: 1581-1585 (1988)), Raji cells (CCL-86), and derivatives thereof.

A nucleic acid sequence encoding the inventive amino acid sequence may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols*, Humana Press (1991)); DEAE-dextran; electroporation; cationic liposome-mediated transfection; tungsten particle-facilitated microparticle bombardment (Johnston, *Nature*, 346: 776-777 (1990)); and Strontium phosphate DNA co-precipitation (Brash et al., *Mol. Cell Biol.*, 7: 2031-2034 (1987)). Phage or viral vectors can be introduced into host cells, after growth of infectious particles in suitable packaging cells, many of which are commercially available.

Compositions

The invention provides a composition comprising the Dectin-2 binding agent or nucleic acid(s) encoding same optionally in a vector. Preferably, the composition is a pharmaceutically acceptable (e.g., physiologically acceptable) composition, which comprises a carrier, preferably a pharmaceutically acceptable (e.g., physiologically acceptable) carrier, and the Dectin-2 binding agent or nucleic acid(s) encoding same. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., Remington: *The Science and Practice of Pharmacy,* 21st Edition, Lippincott Williams & Wilkins, Philadelphia, Pa. (2001).

The composition can be formulated for parenteral administration, such as IV administration or administration into a body cavity or lumen of an organ. Alternatively, the composition can be injected intra-tumorally. Compositions for injection will commonly comprise the active ingredient dissolved or suspended in a pharmaceutically acceptable carrier. Among the acceptable vehicles and solvents that can be employed are water and an isotonic solution of one or more salts such as sodium chloride, e.g., Ringer's solution. In addition, sterile fixed oils can conventionally be employed as a solvent or suspending medium. For this purpose, any bland fixed oil can be employed, including synthetic monoglycerides or diglycerides. In addition, fatty acids such as oleic acid can likewise be used in the preparation of injectables. These compositions desirably are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The composition can contain any suitable concentration of the Dectin-2 binding agent or nucleic acid(s) encoding same optionally in a vector, in some embodiments, a concentration effective to elicit a therapeutic response. The concentration can vary widely, and will be selected primarily based on fluid volumes, viscosities, body weight, and the like, in accordance with the particular mode of administration selected and the patient's needs. In certain embodiments, the concentration of the inventive immunoglobulin heavy chain polypeptide, the inventive immunoglobulin light chain polypeptide, the inventive Dectin-2 binding agent, the inventive nucleic acid sequence encoding any of the foregoing, or the inventive vector comprising the inventive nucleic acid sequence in a solution formulation for injection will range from about 0.1% (w/w) to about 10% (w/w).

Methods

The Dectin-2 binding agents provided herein can be used for any suitable purpose. For instance, the Dectin-2 binding agents can agonistically bind Dectin-2 expressing cells, and be used to activate or enhance Dectin-2 signaling therein (e.g., for therapeutic purposes). Accordingly, one aspect of the disclosure provides a method of treating a disease, condition, or disorder responsive to the activation and/or enhancement of Dectin-2 signaling in a mammal by administering a Dectin-2 binding agent, or composition comprising same, as described herein, to the mammal.

In some embodiments, the Dectin-2 binding agents can stimulate an antigen presenting cell (APC). Stimulation can occur by contacting an APC with a Dectin-2 binding agent at a dose and for a period of time sufficient to enhance Dectin-2 signaling in the APC, thereby generating a stimulated APC. In some embodiments, the APC is a cell of myeloid lineage. Examples of cells of myeloid lineage include monocytes, macrophages, and dendritic cells. In some embodiments, stimulated APCs produce at least one pro-inflammatory cytokine, examples of which include Tumor Necrosis Factor alpha, IL-10, IL-2, IL-6, IL-23p19, IFNγ, IL-12p40, and IL-12p70. In some embodiments, stimulated APCs exhibit increased phagocytosis in comparison to APCs that have not been contacted by a Dectin-2 binding agent. In some embodiments, the stimulated APC is contacted with a cancer antigen to produce an antigen-contacted APC. The cancer antigen can be, for example, present in a cancer cell lysate or be part of a cancer cell. The cancer cell lysate or cancer cell can be taken or derived from an individual. In some embodiments, the individual has cancer.

In some embodiments, the stimulated APC or the antigen-contacted APC is introduced into an individual. In embodiments wherein the antigen used to contact the APC is taken or derived from an individual to produce an antigen-contacted APC, the antigen-contacted APC can be introduced into the individual. Such a stimulated APC or antigen-contacted APC can be autologous to the individual.

In some embodiments, the antigen-contacted APC is contacted with a T cell. The T cell can be introduced into an individual. The T cell and the antigen-contacted APC, with which the T cell is contacted, can each be autologous to the individual. In some embodiments, the individual has cancer.

As used herein, the terms "treat," "treatment," and "treating" refer to any indicia of success in the treatment or amelioration of an injury, pathology, condition (e.g., cancer), or symptom, including any objective or subjective parameter such as abatement; remission; diminishing of symptoms or making the symptom, injury, pathology, or condition more tolerable to the patient; reduction in the rate of symptom progression; decreasing the frequency or duration of the symptom or condition; or, in some situations, preventing the onset of the symptom. The treatment or amelioration of symptoms can be based on any objective or subjective parameter, including, for example, the result of a physical examination.

The terms "reduce" or "alleviate," as used herein with respect to the activity of a Dectin-2 binding agent, refer to the ability to substantially prohibit, prevent, restrain, slow, disrupt, alter, eliminate, stop, or reverse the progression or severity of a disease or condition (e.g., cancer) associated with a Dectin-2 protein.

The terms "cancer," "neoplasm," and "tumor" are used herein to refer to cells which exhibit autonomous, unregulated growth, such that the cells exhibit an aberrant growth phenotype characterized by a significant loss of control over cell proliferation. Cells of interest for detection, analysis, and/or treatment in the context of the invention include cancer cells (e.g., cancer cells from an individual with cancer), malignant cancer cells, pre-metastatic cancer cells, metastatic cancer cells, and non-metastatic cancer cells. Cancers of virtually every tissue are known. The phrase "cancer burden" refers to the quantum of cancer cells or cancer volume in a subject. Reducing cancer burden accordingly refers to reducing the number of cancer cells or the cancer cell volume in a subject. The term "cancer cell" as used herein refers to any cell that is a cancer cell (e.g., from any of the cancers for which an individual can be treated, e.g., isolated from an individual having cancer) or is derived from a cancer cell, e.g., clone of a cancer cell. For example, a cancer cell can be from an established cancer cell line, can be a primary cell isolated from an individual with cancer, can be a progeny cell from a primary cell isolated from an individual with cancer, and the like. In some embodiments, the term can also refer to a portion of a cancer cell, such as a sub-cellular portion, a cell membrane portion, or a cell lysate of a cancer cell. Many types of cancers are known to those of skill in the art, including solid tumors such as carcinomas, sarcomas, glioblastomas, melanomas, lymphomas, and myelomas, and circulating cancers such as leukemias.

As used herein, the term "cancer" includes any form of cancer, including but not limited to, solid tumor cancers (e.g., skin, lung, prostate, breast, gastric, bladder, colon, ovarian, pancreas, kidney, liver, glioblastoma, medulloblastoma, leiomyosarcoma, head & neck squamous cell carcinomas, melanomas, and neuroendocrine) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors.

Any cancer that can be influenced by cells expressing Dectin-2 is a suitable cancer to be treated by the subject methods and compositions. As used herein "Dectin-2 expression" refers to a cell that has a Dectin-2 receptor on the cell's surface.

Carcinomas are malignancies that originate in the epithelial tissues. Epithelial cells cover the external surface of the body, line the internal cavities, and form the lining of glandular tissues. Examples of carcinomas include, but are not limited to, adenocarcinoma (cancer that begins in glandular (secretory) cells such as cancers of the breast, pancreas, lung, prostate, stomach, gastroesophageal junction, and colon); adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma (e.g., head and neck squamous cell carcinoma); transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like. Carcinomas may be found in prostrate, pancreas, colon, brain (usually as secondary metastases), lung, breast, and skin.

Soft tissue tumors are a highly diverse group of rare tumors that are derived from connective tissue. Examples of soft tissue tumors include, but are not limited to, alveolar soft part sarcoma; angiomatoid fibrous histiocytoma; chondromyoxid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); fibrosarcoma, infantile; gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma; osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DF SP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; pleomorphic adenoma of soft tissue; and neoplasias derived from fibroblasts, myofibroblasts, histiocytes, vascular cells/endothelial cells, and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to, askin's tumor; sarcoma botryoides; chondrosarcoma; ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; and undifferentiated pleomorphic sarcoma).

A teratoma is a type of germ cell tumor that may contain several different types of tissue (e.g., can include tissues derived from any and/or all of the three germ layers: endoderm, mesoderm, and ectoderm), including, for example, hair, muscle, and bone. Teratomas occur most often in the ovaries in women, the testicles in men, and the tailbone in children.

Melanoma is a form of cancer that begins in melanocytes (cells that make the pigment melanin). Melanoma may begin in a mole (skin melanoma), but can also begin in other pigmented tissues, such as in the eye or in the intestines.

Merkel cell carcinoma is a rare type of skin cancer that usually appears as a flesh-colored or bluish-red nodule. It frequently appears on the face, head or neck. Merkel cell carcinoma is also called neuroendocrine carcinoma of the skin. In some embodiments, the Merkel cell carcinoma has metastasized when administration occurs.

Leukemias are cancers that start in blood-forming tissue, such as the bone marrow, and cause large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is affected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to, Acute myeloid leukemia (AML), Acute lymphoblastic leukemia (ALL), Chronic myeloid leukemia (CIVIL), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One category of lymphoma is Hodgkin lymphoma (HL), which is marked by the presence of a type of cell called the Reed-Sternberg cell. There are currently 6 recognized types of HL. Examples of Hodgkin lymphomas include nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to, AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to, gliomas (e.g., glioblastomas, astrocytomas, oligodendrogliomas, ependymomas, and the like), meningiomas, pituitary adenomas, and vestibular schwannomas, primitive neuroectodermal tumors (medulloblastomas).

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, and invasion of surrounding or distant tissues or organs, such as lymph nodes.

As used herein, the phrases "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs, therefore, tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part that is not directly connected to the organ of the original cancerous tumor. Metastasis can also be defined as several steps of a process, such as the departure of cancer cells from an original tumor site, and migration and/or invasion of cancer cells to other parts of the body.

As used herein the phrases "effective amount" and "therapeutically effective amount" refer to a dose of a substance such as a binding agent that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); *Goodman & Gilman's The Pharmacological Basis of Therapeutics*, $11^{th}$ Edition (McGraw-Hill, 2006); and *Remington: The Science and Practice of Pharmacy*, $22^{nd}$ Edition, (Pharmaceutical Press, London, 2012)).

As used herein, the terms "recipient," "individual," "subject," "host," and "patient" are used interchangeably and refer to any mammalian subject for whom diagnosis, treatment, or therapy is desired (e.g., humans). "Mammal" for purposes of treatment refers to any animal classified as a mammal, including humans, domestic and farm animals, and zoo, sports, or pet animals, such as dogs, horses, cats, cows, sheep, goats, pigs, camels, etc. In certain embodiments, the mammal is human.

As used herein, the term "administering" refers to parenteral, intravenous, intraperitoneal, intramuscular, intratumoral, intralesional, intranasal, or subcutaneous administration, oral administration, administration as a suppository, topical contact, intrathecal administration, or the implantation of a slow-release device, e.g., a mini-osmotic pump, to the subject.

Administration of a composition comprising the inventive immunoglobulin heavy chain polypeptide, the inventive immunoglobulin light chain polypeptide, the inventive Dectin-2 binding agent, the inventive nucleic acid sequence encoding any of the foregoing, or the inventive vector comprising the inventive nucleic acid sequence induces an immune response against a cancer in a mammal. An "immune response" can entail, for example, activation (induction) of one or more Dectin-2-associated pathways (signaling) in Dectin-2 expressing cells, which can lead to the expression of pro-inflammatory cytokines and/or increased phagocytosis in Dectin-2 expressing cells.

The inventive methods comprise administering a "therapeutically effective amount" of the binding agent. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the binding agent to elicit a desired response in the individual. For example, a therapeutically effective amount of a binding agent of the invention is an amount enhances the immune response against a cancer.

Alternatively, the pharmacologic and/or physiologic effect may be prophylactic, i.e., the effect completely or partially prevents a disease or symptom thereof. In this respect, the inventive method comprises administering a "prophylactically effective amount" of the binding agent. A "prophylactically effective amount" refers to an amount effective, at dosages and for periods of time necessary, to achieve a desired prophylactic result (e.g., prevention of disease onset).

A typical dose can be, for example, in the range of 1 µg/kg to 20 mg/kg of animal or human body weight; however, doses below or above this exemplary range are within the scope of the invention. The daily parenteral dose can be about 0.00001 µg/kg to about 20 mg/kg of total body weight (e.g., about 0.001 µg/kg, about 0.1 µg/kg, about 1 µg/kg, about 5 µg/kg, about 10 µg/kg, about 100 µg/kg, about 500 µg/kg, about 1 mg/kg, about 5 mg/kg, about 10 mg/kg, or a range defined by any two of the foregoing values), preferably from about 0.1 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), more preferably from about 1 µg/kg to 5 mg/kg of total body weight (e.g., about 3 µg/kg, about 15 µg/kg, about 75 µg/kg, about 300 µg/kg, about 900 µg/kg, about 2 mg/kg, about 4 mg/kg, or a range defined by any two of the foregoing values), and even more preferably from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

The composition comprising an effective amount of the inventive immunoglobulin heavy chain polypeptide, the inventive immunoglobulin light chain polypeptide, the inventive binding agent, the inventive nucleic acid sequence encoding any of the foregoing, or the inventive vector comprising the inventive nucleic acid sequence can be administered to a mammal using standard administration techniques, including oral, intravenous, intraperitoneal, sub- cutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

Once administered to a mammal (e.g., a human), the biological activity of the inventive binding agent can be measured by any suitable method known in the art. For example, the biological activity can be assessed by determining the stability of a particular binding agent. In one embodiment of the invention, the binding agent (e.g., an antibody) has an in vivo half life between about 30 minutes and 45 days (e.g., about 30 minutes, about 45 minutes, about 1 hour, about 2 hours, about 4 hours, about 6 hours, about 10 hours, about 12 hours, about 1 day, about 5 days, about 10 days, about 15 days, about 25 days, about 35 days, about 40 days, about 45 days, or a range defined by any two of the foregoing values). In another embodiment, the Dectin-2 binding agent has an in vivo half life between about 2 hours and 20 days (e.g., about 5 hours, about 10 hours, about 15 hours, about 20 hours, about 2 days, about 3 days, about 7 days, about 12 days, about 14 days, about 17 days, about 19 days, or a range defined by any two of the foregoing values). In another embodiment, the binding agent has an in vivo half life between about 10 days and about 40 days (e.g., about 10 days, about 13 days, about 16 days, about 18 days, about 20 days, about 23 days, about 26 days, about 29 days, about 30 days, about 33 days, about 37 days, about 38 days, about 39 days, about 40 days, or a range defined by any two of the foregoing values).

In addition to therapeutic uses, the binding agent described herein can be used in diagnostic or research applications. In this respect, the binding agent can be used in a method to diagnose a cancer. In a similar manner, the binding agent can be used in an assay to monitor Dectin-2 protein levels in a subject being tested for a disease or disorder that is associated with abnormal Dectin-2 expression. Research applications include, for example, methods that utilize the binding agent and a label to detect a Dectin-2 protein in a sample, e.g., in a human body fluid or in a cell or tissue extract. The binding agent can be used with or without modification, such as covalent or non-covalent labeling with a detectable moiety. For example, the detectable moiety can be a radioisotope (e.g., $^{3}$H, $^{14}$C, $^{32}$P, $^{35}$S, or $^{125}$I) a fluorescent or chemiluminescent compound (e.g., fluorescein isothiocyanate, rhodamine, or luciferin), an enzyme (e.g., alkaline phosphatase, beta-galactosidase, or horseradish peroxidase), or prosthetic groups. Any method known in the art for separately conjugating an antigen-binding agent (e.g., an antibody) to a detectable moiety may be employed in the context of the invention (see, e.g., Hunter et al., *Nature,* 194: 495-496 (1962); David et al., *Biochemistry,* 13: 1014-1021 (1974); Pain et al., *J. Immunol. Meth.,* 40: 219-230 (1981); and Nygren, *J. Histochem. and Cytochem.,* 30: 407-412 (1982)).

Dectin-2 protein levels can be measured using the inventive binding agent by any suitable method known in the art. Such methods include, for example, immunohistochemistry, immunofluorescence, radioimmunoassay (MA), and FACS. Normal or standard expression values of Dectin-2 protein can be established using any suitable technique, e.g., by combining a sample comprising, or suspected of comprising, a Dectin-2 polypeptide with a Dectin-2 specific antibody under conditions suitable to form an antigen-antibody complex. The antibody is directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, *Monoclonal Antibodies: A Manual of Techniques*, CRC Press, Inc. (1987)). The amount of Dectin-2 polypeptide expressed in a sample is then compared with a standard value.

Kits

The binding agent can be provided in a kit, i.e., a packaged combination of reagents in predetermined amounts with instructions for performing a diagnostic assay. If the binding agent is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

Examples of Non-Limiting Aspects of the Disclosure

Aspects, including embodiments, of the invention described herein may be beneficial alone or in combination, with one or more other aspects or embodiments. Without limiting the foregoing description, certain non-limiting aspects of the disclosure numbered (1)-(33) are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

(1) A Dectin-2 binding agent comprising an immunoglobulin heavy chain variable region polypeptide and an immunoglobulin light chain variable region polypeptide, wherein:

the immunoglobulin heavy chain variable region polypeptide comprises a complementarity determining region 1 (HCDR1) comprising any one of SEQ ID NOs: 1-30, a complementarity determining region 2 (HCDR2) comprising any one of SEQ ID NOs: 31-64, and a complementarity determining region 3 (HCDR3) comprising any one of SEQ ID NOs: 65-103 or 323; or the immunoglobulin light chain variable region polypeptide comprises a complementarity determining region 1 (LCDR1) comprising any one of SEQ ID NOs: 104-125, a complementarity determining region 2 (LCDR2) comprising any one of SEQ ID NOs: 126-148, and a complementarity determining region 3 (LCDR3) comprising any one of SEQ ID NOs: 149-181.

(2) A Dectin-2 binding agent comprising an immunoglobulin heavy chain variable region of any one of SEQ ID NOs: 243-282 or 324, or at least the CDRs thereof; and an immunoglobulin light chain variable region of any one of SEQ ID NOs: 283-322 or at least the CDRs thereof.

(3) A Dectin-2 binding agent comprising an immunoglobulin heavy chain variable region polypeptide with an amino acid sequence that is at least 90% identical to any one of SEQ ID NOs: 243-282 or 324, and an immunoglobulin light chain variable region polypeptide with an amino acid sequence that is at least 90% identical to any one of SEQ ID NOs: 284-322.

(4) The Dectin-2 binding agent of any one of aspects 1-3, which comprises the heavy and light chain immunoglobulin polypeptides, or at least the CDRs thereof, of a Dectin-2 binding agent of Table 1.

(5) The Dectin-2 binding agent of any one of aspects 1-4, wherein the binding agent is an antibody, an antibody conjugate, or an antigen-binding fragment thereof.

(6) The Dectin-2 binding agent of aspect 5, wherein the binding agent is an antibody fragment selected from F(ab')2, Fab', Fab, Fv, scFv, dsFv, dAb, and a single chain binding polypeptide.

(7) The Dectin-2 binding agent of aspect 5, wherein the binding agent is an antibody.

(8) The Dectin-2 binding agent of any one of aspects 5-7, wherein the antibody is an IgG, IgM, IgA, IgD or IgE antibody.

(9) The Dectin-2 binding agent of any one of aspects 5-8, wherein the antibody is an IgG antibody.

(10) The Dectin-2 binding agent of aspect 9, wherein the IgG antibody comprises one or more mutations in the Fc region that result in modulated binding to one or more Fc receptors.

(11) The Dectin-2 binding agent of any one of aspects 7-10, wherein the antibody exhibits antibody dependent cell-mediated cytotoxicity (ADCC), antibody-dependent cell-mediated phagocytosis (ADCP), or complement dependent cytotoxicity (CDC).

(12) The Dectin-2 binding agent of any of aspects 1-11, wherein the binding agent is part of a bispecific antibody, chimeric antigen receptor, chimeric T cell receptor, or bispecific T-cell engager.

(13) A nucleic acid encoding the heavy chain immunoglobulin polypeptide of the Dectin-2 binding agent of any one of aspects 1-12.

(14) A nucleic acid encoding the light chain immunoglobulin polypeptide of the Dectin-2 binding agent of any one of aspects 1-12.

(15) A nucleic acid encoding the heavy chain immunoglobulin polypeptide and the light chain immunoglobulin polypeptide of the Dectin-2 binding agent of any one of aspects 1-12.

(16) A vector comprising the nucleic acid sequence of any one of aspects 13-15.

(17) An isolated cell comprising the nucleic acid of any one of aspects 13-15, optionally in a vector.

(18) A method of providing a Dectin-2 binding agent of any of aspects 1-12, the method comprising expressing in a cell in vitro one or more nucleic acids encoding the immunoglobulin heavy and light chain polypeptides thereof.

(19) A composition comprising the Dectin-2 binding agent of any one of aspects 1-12 or nucleic acid of any one of aspects 13-15, optionally in a vector, and a pharmaceutically acceptable carrier.

(20) The Dectin-2 binding agent of any one of aspects 1-12 or conjugate comprising same, or the composition of aspect 19, for use as a medicament for treating a disease, disorder, or condition in a mammal that is responsive to Dectin-2 inhibition or binding.

(21) The Dectin-2 binding agent or composition of aspect 20, wherein the disease, disorder, or condition is cancer.

(22) The Dectin-2 binding agent of any one of aspects 1-12 or the composition of aspect 19 for use as a medicament for enhancing an immune response in a mammal.

(23) The Dectin-2 binding agent for use according to aspect 22, wherein the immune response is an anti-tumor immune response.

(24) A method for treating a disease, disorder, or condition in a mammal that is responsive to Dectin-2 binding or inhibition, the method comprising administering the Dectin-2 binding agent of any one of aspects 1-12 or conjugate comprising same, or the composition of aspect 19, to the mammal.

(25) The method of aspect 24, wherein the disease, disorder, or condition is cancer.

(26) A hybridoma or cell line that expresses a Dectin-2 binding agent of any of aspects 1-12.

(27) A method of stimulating an antigen presenting cell (APC), the method comprising contacting an APC with a Dectin-2 binding agent of aspects 1-12 at a dose and for a period of time sufficient to enhance Dectin-2 signaling in the APC, thereby generating a stimulated APC.

(28) The method according to aspect 27, wherein the APC is a cell of myeloid lineage.

(29) The method according to aspect 28, wherein the myeloid cell is a monocyte, macrophage, or a dendritic cell.

(30) The method according to aspects 27-29, wherein the stimulated APC produces at least one pro-inflammatory cytokine and/or exhibits increased phagocytosis as compared to an APC that has not been contacted by a Dectin-2 binding agent.

(31) The method according to aspect 30, wherein the at least one pro-inflammatory cytokine is selected from the group consisting of TNFα, IL-1β, IL-2, IL-6, IL-23p19, IFNγ, IL-12p40, and IL-12p70.

(32) The method according to any of aspects 27-31, comprising contacting the stimulated APC with a cancer antigen to produce an antigen-contacted APC.

(33) The method according to any of aspects 28-32, wherein the cancer antigen is present in a cancer cell lysate or is part of a cancer cell.

EXAMPLES

Human monocytes were isolated from LRS chambers obtained from the Stanford Blood Center (Palo Alto, Calif.; chamber is a byproduct from leukapheresis) using RosetteSep™ Human Monocyte Enrichment Cocktail (STEMCELL Technologies Inc.) followed by the EasySep™ Human Monocyte Enrichment Kit without CD16 Depletion (STEMCELL Technologies Inc.) according to the manufacturer's instructions. The isolated human monocytes were used in the following experiments.

Example 1

In a first experiment, the isolated human monocytes were cultured in complete RPMI medium (10% FBS, P/S, glutamine) supplemented with 100 ng/mL hGM-CSF (PeproTech, Inc.). Following two days' incubation, the treated monocytes were harvested with a cell scraper and added to TC-treated 96-well plates (Corning Inc., Corning, N.Y.) which were pre-coated with one of the antibody clones listed in FIG. 1. The antibody-coated 96-well plates used in this experiment were prepared by diluting the indicated antibody to 25 µg/mL in PBS, and incubating overnight at 4° C., followed by several PBS washes. After an 18 hour incubation, supernatants were collected and TNFα levels were measured by ELISA according to the manufacturer's instructions (Invitrogen eBioscience Human TNF alpha ELISA Ready-SET-Go!). The results of the first experiment are shown in FIG. 1. As can be seen in FIG. 1, a number of the tested antibodies triggered a significant increase in TNFα expression.

The tested antibodies correspond to Binding Agents 1-40 disclosed herein, as follows:

TABLE 8

| Tested Antibody | Binding Agent (VH and VL SEQ ID NOs) | Tested Antibody | Binding Agent (VH and VL SEQ ID NOs) |
| --- | --- | --- | --- |
| R3H-P1C02 | 1 (SEQ ID NOs: 243 and 283) | R3H-P1E01 | 21 (SEQ ID NOs: 262 and 303) |
| R3H-P3A02 | 2 (SEQ ID NOs: 244 and 284) | R3C-P2B08 | 22 (SEQ ID NOs: 263 and 304) |
| R3H-P3H07 | 3 (SEQ ID NOs: 245 and 285) | R3C-P1G05 | 23 (SEQ ID NOs: 264 and 305) |
| R3M-P2C06 | 4 (SEQ ID NOs: 246 and 286) | R3H-P1B11 | 24 (SEQ ID NOs: 266 and 306) |
| R3C-P1E10 | 5 (SEQ ID NOs: 247 and 287) | R3H-P2B10 | 25 (SEQ ID NOs: 267 and 307) |
| R3H-P1D01 | 6 (SEQ ID NOs: 248 and 288) | R3C-P3C07 | 26 (SEQ ID NOs: 268 and 308) |
| R3H-P1C10 | 7 (SEQ ID NOs: 249 and 289) | R3H-P3A06 | 27 (SEQ ID NOs: 269 and 309) |
| R3H-P2D03 | 8 (SEQ ID NOs: 250 and 290) | R3H-P3D01 | 28 (SEQ ID NOs: 270 and 310) |
| R4H-P1G05 | 9 (SEQ ID NOs: 251 and 291) | R3M-P2D05 | 29 (SEQ ID NOs: 271 and 311) |
| R3M-P1C03 | 10 (SEQ ID NOs: 252 and 292) | R3C-P2D05 | 30 (SEQ ID NOs: 272 and 312) |
| R3H-P2G03 | 11 (SEQ ID NOs: 253 and 293) | R3H-P2D12 | 31 (SEQ ID NOs: 273 and 313) |
| R4H-P1G11 | 12 (SEQ ID NOs: 254 and 294) | R3H-P2A09 | 32 (SEQ ID NOs: 274 and 314) |
| R3H-P1B01 | 13 (SEQ ID NOs: 255 and 295) | R3H-P2G01 | 33 (SEQ ID NOs: 275 and 315) |
| R3C-P1C09 | 14 (SEQ ID NOs: 256 and 296) | R3M-P3E03 | 34 (SEQ ID NOs: 276 and 316) |
| R3H-P1G03 | 15 (SEQ ID NOs: 257 and 297) | R3H-P3B09 | 35 (SEQ ID NOs: 277 and 317) |
| R3M-P3B04 | 16 (SEQ ID NOs: 258 and 298) | R4C-P1F06 | 36 (SEQ ID NOs: 278 and 318) |
| R3H-P2F02 | 17 (SEQ ID NOs: 259 and 299) | R3H-P2D07 | 37 (SEQ ID NOs: 279 and 319) |
| R3M-P3B11 | 18 (SEQ ID NOs: 256 and 300) | R3M-P3C04 | 38 (SEQ ID NOs: 280 and 320) |
| R3M-P1D05 | 19 (SEQ ID NOs: 260 and 301) | R3H-P1C12 | 39 (SEQ ID NOs: 281 and 321) |
| R3H-P1F05 | 20 (SEQ ID NOs: 261 and 302) | R3C-P1C01 | 40 (SEQ ID NOs: 282 and 322) |

Example 2

Figure 2:
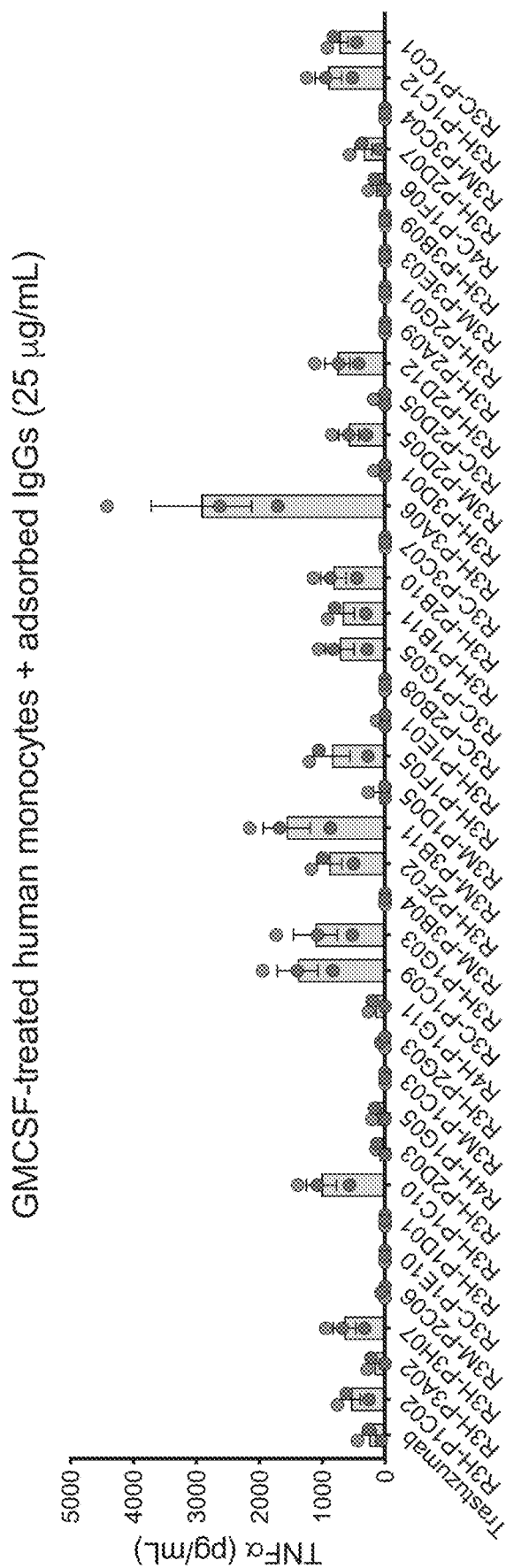
FIG. 2 is a bar graph of TNFα (pg/mL) secreted by GM-CSF-treated human monocytes which have been exposed to certain plate-adsorbed anti-Dectin-2 antibodies at a concentration of 25 μg/mL.

In a second experiment, isolated human monocytes were cultured in complete RPMI medium (10% FBS, P/S, glutamine) supplemented with 200 ng/mL hGM-CSF (PeproTech, Inc.). Following three days' incubation, the treated monocytes were harvested with a cell scraper and added to TC-treated 96 well plates (Corning Inc., Corning, N.Y.), wherein the monocytes were stimulated with one of the antibody clones listed in FIG. 2 (in soluble form) at 100 µg/mL. After an 18 hour incubation, supernatants were collected and TNFα levels were measured by ELISA according to the manufacturer's instructions (Invitrogen eBioscience Human TNF alpha ELISA Ready-SET-Go!). The results of the first experiment are shown in FIG. 2. As can be seen in FIG. 2, a number of the tested antibodies triggered a significant increase in TNFα expression. The tested antibodies correspond to the Binding Agents disclosed herein as shown in Table 8.

Example 3

Figure 3:
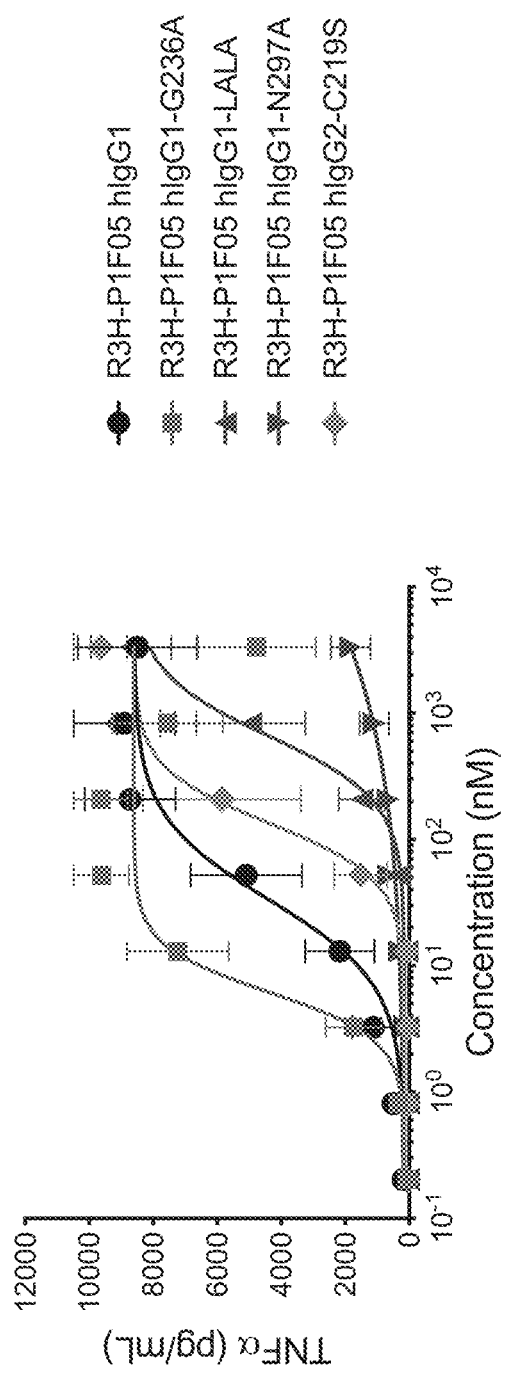
FIG. 3 is a graph of TNFα (pg/mL) secreted by GM-CSF-treated human monocytes stimulated with different concentrations (nM) of each of the indicated antibodies.

In a third experiment, isolated human monocytes were cultured in complete RPMI medium (10% FBS, P/S, glutamine) supplemented with human GM-CSF (PeproTech, Inc.). Following 6 days of incubation, macrophages were harvested and added to TC-treated 96 well plates (Corning Inc., Corning, N.Y.), wherein the macrophages were stimulated with a dose titration of each of the indicated antibodies. After an 18 hour incubation, supernatants were collected and TNFα levels were measured by ELISA according to the manufacturer's instructions (Invitrogen eBioscience Human TNF alpha ELISA Ready-SET-Go!). As can be seen in FIG. 3, a number of the tested antibodies triggered a significant increase in TNFα expression. The tested antibodies were each R3H-P1F05 (corresponding to Binding Agent 20 disclosed herein, (i.e., comprising VH and VL regions respectively SEQ ID NOs: 261 and 302)), each with or without certain modifications to the Fc region of the antibody as shown on FIG. 3, including, for example, use of an IgG2 Fc domain instead of an IgG1 Fc domain.

Specifically, R3H-P1F05 comprises SEQ ID NOs: 326 and 334, R3H-P1F05 hIgG1-G236A comprises SEQ ID NOs 326 and 335, R3H-P1F05 hIgG1-LALA comprises SEQ ID NOs: 326 and 336, R3H-P1F05 hIgG1-N297A comprises SEQ ID NOs: 326 and 337, and R3H-P1F05 hIgG1-C219S comprises SEQ ID NOs: 326 and 338.

Example 4

Figure 4:
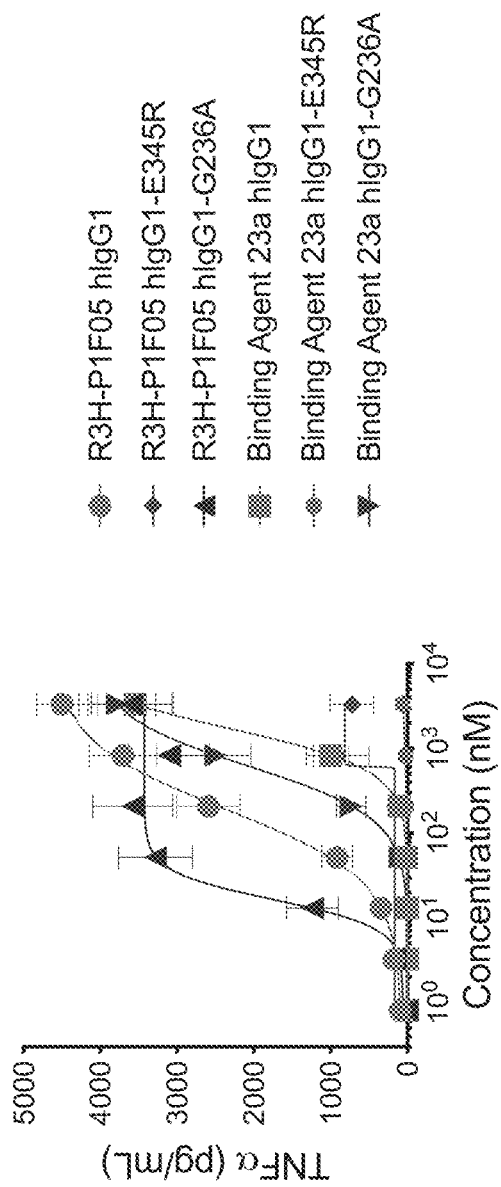
FIG. 4 is a graph of TNFα (pg/mL) secreted by GM-CSF-treated human monocytes stimulated with different concentrations (nM) of each of the indicated antibodies.

In a fourth experiment, isolated human monocytes were cultured in complete RPMI medium (10% FBS, P/S, glutamine) supplemented with human GM-CSF (PeproTech, Inc.). Following 5 days of incubation, macrophages were harvested and added to TC-treated 96 well plates (Corning Inc., Corning, N.Y.), wherein the macrophages were stimulated with a dose titration of each of the indicated antibodies. After a 20 hour incubation, supernatants were collected and TNFα levels were measured by ELISA according to the manufacturer's instructions (Invitrogen eBioscience Human TNF alpha ELISA Ready-SET-Go!). As can be seen in FIG. 4, a number of the tested antibodies triggered a significant increase in TNFα expression. The tested antibodies were each R3H-P1F05 (corresponding to Binding Agent 20 disclosed herein (VH and VL regions respectively SEQ ID NOs: 261 and 302)), or an antibody corresponding to Binding Agent 23a disclosed herein (i.e., comprising VH and VL regions respectively SEQ ID NOs: 265 and 305), each with or without certain modifications to the Fc region of the antibody as shown in FIG. 4.

Specifically, R3H-P1F05 comprises SEQ ID NOs: 326 and 334, R3H-P1F05-E345R comprises SEQ ID NOs: 326 and 339, R3H-P1F05 hIgG1-G236A comprises SEQ ID NOs 326 and 335, Binding Agent 23a hIgG1 comprises SEQ ID NOs: 327 and 340, Binding Agent 23a hIgG1-E345R comprises SEQ ID NOs: 327 and 341, and Binding Agent 23a hIgG1-G236A comprises SEQ ID NOs: 327 and 342.

Example 5

In a fifth experiment, isolated human monocytes were cultured in complete RPMI medium (10% FBS, P/S, glutamine) supplemented with human M-CSF (PeproTech, Inc.). Following 6 days incubation, macrophages were harvested and added to TC-treated 96 well plates (Corning Inc., Corning, N.Y.), wherein the macrophages were stimulated with a dose titration of each of the indicated antibodies. After a 20 hour incubation, supernatants were collected and TNFα levels were measured by ELISA according to the manufacturer's instructions (Invitrogen eBioscience Human TNF alpha ELISA Ready-SET-Go!). As can be seen in FIGS. 5A and 5B, a number of the tested antibodies triggered a significant increase in TNFα expression. The tested antibodies were each R3H-P1F05 (FIG. 5A) (corresponding to Binding Agent 20 disclosed herein (i.e., comprising VH and VL regions respectively SEQ ID NOs: 261 and 302)), or Binding Agent 23a disclosed herein (FIG. 5B) (i.e., comprising VH and VL regions respectively SEQ ID NOs: 265 and 305), each with or without certain modifications to the Fc region of the antibody as shown in FIGS. 5A and 5B, wherein "nf" stands for non-fucosylated (i.e, afucosylated).

Specifically, in FIG. 5A, R3H-P1F05 and R3H-P1F05-nf each comprise SEQ ID NOs: 326 and 334, and R3H-P1F05 hIgG1-G236A and R3H-P1F05 hIgG1-G236A-nf each comprise SEQ ID NOs 326 and 335. In FIG. 5B, Binding Agent 23a hIgG1 and Binding Agent 23a hIgG1-nf each comprise SEQ ID NOs: 327 and 340, and Binding Agent 23a hIgG1-G236A and Binding Agent 23a hIgG1-G236A-nf each comprise SEQ ID NOs: 327 and 342.

Example 6

Figure 6:
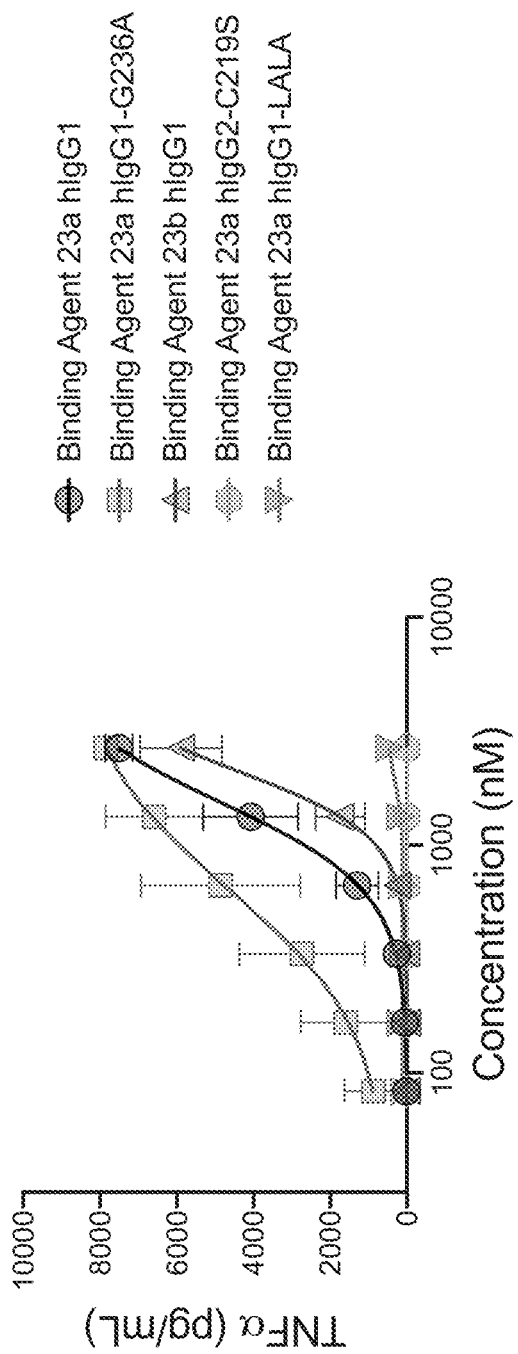
FIG. 6 is a graph of TNFα (pg/mL) secreted by M-CSF-treated human monocytes stimulated with different concentrations (nM) of each of the indicated antibodies.

In a sixth experiment, isolated human monocytes were cultured in complete RPMI medium (10% FBS, P/S, glutamine) supplemented with human M-CSF (PeproTech, Inc.). Following 5 days incubation, macrophages were harvested and added to TC-treated 96 well plates (Corning Inc., Corning, N.Y.), wherein the macrophages were stimulated with a dose titration of each of the indicated antibodies. After a 20 hour incubation, supernatants were collected and TNFα levels were measured by ELISA according to the manufacturer's instructions (Invitrogen eBioscience Human TNF alpha ELISA Ready-SET-Go!). As can be seen in FIG. 6, a number of the tested antibodies triggered a significant increase in TNFα expression. The tested antibodies were each an antibody corresponding to Binding Agent 23a disclosed herein (i.e., comprising VH and VL regions respectively SEQ ID NOs: 265 and 305), or an antibody corresponding to Binding Agent 23b disclosed herein (i.e., comprising VH and VL regions respectively SEQ ID NOs: 324 and 305), each with or without certain modifications to the Fc region of the antibody as shown in FIG. 6, including use of an IgG2 domain instead of an IgG1 domain.

Specifically, Binding Agent 23a hIgG1 comprises SEQ ID NOs: 327 and 340, Binding Agent 23a hIgG1-G236A comprises SEQ ID NOs: 327 and 342, Binding Agent 23b hIgG1 comprises SEQ ID NOs: 327 and 345, Binding Agent 23a hIgG2-C219S comprises SEQ ID NOs: 327 and 343, and Binding Agent 23a hIgG1-LALA comprises SEQ ID NOs: 327 and 344.

Example 7

Figure 7:
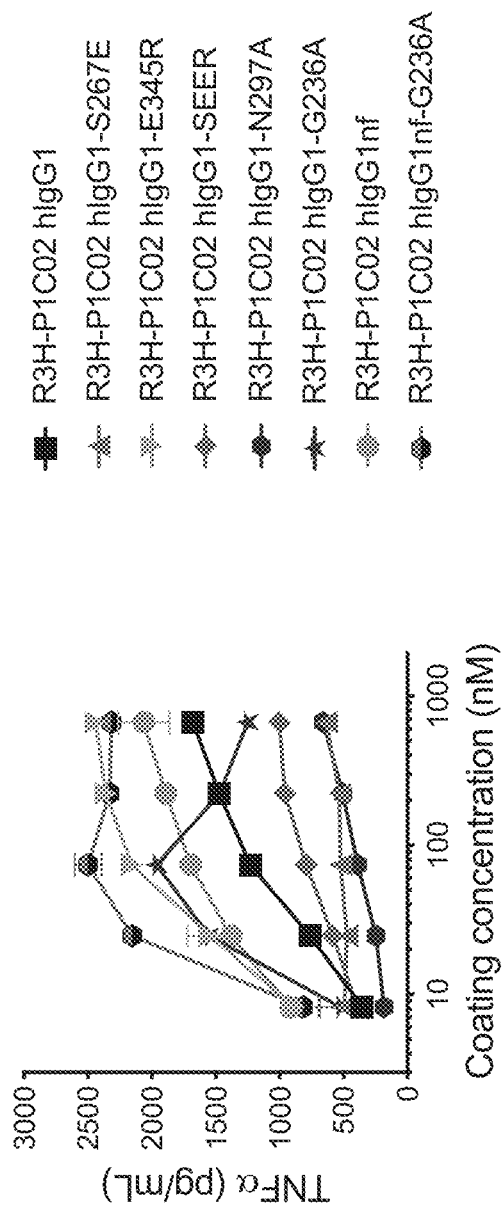
FIG. 7 is a graph of TNFα (pg/mL) secreted by GM-CSF-treated human monocytes stimulated with different concentrations (nM) of each of the indicated antibodies.

In a seventh experiment, isolated human monocytes were cultured in complete RPMI medium (10% FBS, P/S, glutamine) supplemented with human GM-CSF (PeproTech, Inc.). Following 3 days incubation, macrophages were harvested and added to TC-treated 96 well plates (Corning Inc., Corning, N.Y.), which were pre-coated with the indicated antibodies. The antibody-coated 96-well plates used in this experiment were prepared by diluting the indicated antibody in PBS and incubating overnight at 4° C., followed by several PBS washes. After a 20 hour incubation, supernatants were collected and TNFα levels were measured by ELISA according to the manufacturer's instructions (Invitrogen eBioscience Human TNF alpha ELISA Ready-SET-Go!). As can be seen in FIG. 7, a number of the tested antibodies triggered a significant increase in TNFα expression. The tested antibodies were each R3H-P1C02 (corresponding to Binding Agent 1 disclosed herein (i.e., comprising VH and VL regions respectively SEQ ID NOs: 243 and 283)), with or without certain modifications to the Fc region of the antibody as shown in FIG. 7, wherein "nf" stands for non-fucosylated (i.e, afucosylated).

Specifically, each of R3H-P1C02 hIgG1 and R3H-P1C02 hIgG1nf comprises SEQ ID NOs: 325 and 328, R3H-P1C02 hIgG1-S267E comprises SEQ ID NOs: 325 and 329, R3H-P1C02 hIgG1-E345R comprises SEQ ID NOs: 325 and 330, R3H-P1C02 hIgG1-SEER comprises SEQ ID NOs: 325 and 331, R3H-P1C02 hIgG1-N297A comprises SEQ ID NOs: 325 and 332, and each of R3H-P1C02 hIgG1-G236A and R3H-P1C02 hIgG1nf-G236A comprises SEQ ID NOs: 325 and 333.

The terms "about" and "around," as used herein to modify a numerical value, indicate a close range surrounding the numerical value. Thus, if "X" is the value, "about X" or "around X" indicates a value of from 0.9X to 1.1X, e.g., from 0.95X to 1.05X or from 0.99X to 1.01X. A reference to "about X" or "around X" specifically indicates at least the values X, 0.95X, 0.96X, 0.97X, 0.98X, 0.99X, 1.01X, 1.02X, 1.03X, 1.04X, and 1.05X. Accordingly, "about X" and "around X" are intended to teach and provide written description support for a claim limitation of, e.g., "0.98X."

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A Dectin-2 binding agent comprising an immunoglobulin heavy chain variable region polypeptide and an immunoglobulin light chain variable region polypeptide, wherein, according to Kabat numbering:

the immunoglobulin heavy chain variable region polypeptide comprises a complementarity determining region 1 (HCDR1) comprising SEQ ID NO: 18, a complementarity determining region 2 (HCDR2) comprising SEQ ID NO: 49, and a complementarity determining region 3 (HCDR3) comprising SEQ ID NO: 83, and the immunoglobulin light chain variable region polypeptide comprises a complementarity determining region 1 (LCDR1) comprising SEQ ID NO: 117, a complementarity determining region 2 (LCDR2) SEQ ID NO: 138, and a complementarity determining region 3 (LCDR3) comprising SEQ ID NO: 150.

2. A Dectin-2 binding agent comprising an immunoglobulin heavy chain variable region polypeptide comprising complementarity determining regions of SEQ ID NO: 261 and an immunoglobulin light chain variable region polypeptide comprising complementarity determining regions of SEQ ID NO: 302.

3. A Dectin-2 binding agent of claim 1, wherein the immunoglobulin heavy chain variable region polypeptide has an amino acid sequence that is at least 901% identical to SEQ ID NO: 261, and the immunoglobulin light chain variable region polypeptide has an amino acid sequence that is at least 90% identical to SEQ ID NO: 302.

4. A Dectin-2 binding agent comprising an immunoglobulin heavy chain variable region polypeptide of SEQ ID NO: 261 and an immunoglobulin light chain variable region polypeptide of SEQ ID NO: 302.

5. The Dectin-2 binding agent of claim 1, wherein the binding agent is an antibody, an antibody conjugate, or an antigen-binding fragment thereof.

6. The Dectin-2 binding agent of claim 5, wherein the binding agent is an antibody fragment selected from F(ab')$_2$, Fab', Fab, Fv, scFv, dsFv, and a single chain binding polypeptide.

7. The Dectin-2 binding agent of claim 5, wherein the binding agent is an antibody.

8. The Dectin-2 binding agent of claim 5, wherein the antibody is an IgG, TgM, IgA, IgD or IgE antibody.

9. The Dectin-2 binding agent of claim 5, wherein the antibody is an IgG antibody.

10. The Dectin-2 binding agent of claim 9, wherein the IgG antibody comprises one or more mutations in the Fc region that result in modulated binding to one or more Fc receptors.

11. The Dectin-2 binding agent of claim 7, wherein the antibody exhibits antibody dependent cell-mediated cytotoxicity (ADCC), antibody-dependent cell-mediated phagocytosis (ADCP), or complement dependent cytotoxicity (CDC).

12. The Dectin-2 binding agent of claim 1, wherein the binding agent is, or is part of, a multispecific or bispecific antibody, chimeric antigen receptor, chimeric T cell receptor, bispecific T-cell engager, multivalent antibody, diabody, triabody, tetrabody, hexabody, bis-scFV fragment, Fab dimer, or Fab trimer.

13. A composition comprising the Dectin-2 binding agent of claim 1, and a pharmaceutically acceptable carrier.

14. A method for enhancing an immune response in a mammal, the method comprising administering the Dectin-2 binding agent of claim 1 to the mammal, wherein the mammal has a cancer selected from the group consisting of head and neck squamous cell carcinoma, breast cancer, colorectal cancer, non-small cell lung cancer, ovarian cancer, pancreatic ductal adenocarcinoma, and renal cell carcinoma.

15. The method of claim 14, wherein the immune response is an anti-tumor immune response.

16. A method for treating a disease, disorder, or condition in a mammal that is responsive to Dectin-2 binding or activation, the method comprising administering the Dectin-2 binding agent of claim 1 to the mammal, wherein the disease, disorder, or condition is a cancer selected from the group consisting of head and neck squamous cell carcinoma, breast cancer, colorectal cancer, non-small cell lung cancer, ovarian cancer, pancreatic ductal adenocarcinoma, and renal cell carcinoma.

17. The method of claim 16, wherein the cancer is head and neck squamous cell carcinoma.

18. A hybridoma or cell line that expresses a Dectin-2 binding agent of claim 1.

19. A method of stimulating an antigen presenting cell (APC) in a mammal having a cancer selected from the group consisting of head and neck squamous cell carcinoma, breast cancer, colorectal cancer, non-small cell lung cancer, ovarian cancer, pancreatic ductal adenocarcinoma, and renal cell carcinoma, the method comprising contacting an APC with a Dectin-2 binding agent of claim 1 at a dose and for a period of time sufficient to enhance Dectin-2 signaling in the APC, thereby generating a stimulated APC.

20. The method according to claim 19, wherein the APC is a cell of myeloid lineage.

21. The method according to claim 20, wherein the myeloid cell is a monocyte, macrophage, or a dendritic cell.

22. The method according to claim 19, wherein the stimulated APC produces at least one pro-inflammatory cytokine and/or exhibits increased phagocytosis as compared to an APC that has not been contacted by a Dectin-2 binding agent.

23. The method according to claim 22, wherein the at least one pro-inflammatory cytokine is selected from the group consisting of TNFα, IL-10, IL-2, IL-4, IL-23p19, IFNγ, IL-12p40, and IL-12p70.

24. The method according to claim 19, comprising contacting the stimulated APC with a cancer antigen to produce an antigen-contacted APC.

25. The method according to claim 24, wherein the cancer antigen is present in a cancer cell lysate or is part of a cancer cell.

26. The Dectin-2 binding agent of claim 2, wherein the binding agent is an antibody, an antibody conjugate, or an antigen-binding fragment thereof.

27. The Dectin-2 binding agent of claim 26, wherein the binding agent is an antibody fragment selected from F(ab')$_2$, Fab', Fab, Fv, scFv, dsFv, and a single chain binding polypeptide.

28. The Dectin-2 binding agent of claim 26, wherein the binding agent is an antibody.

29. The Dectin-2 binding agent of claim 26, wherein the antibody is an IgG, IgM, IgA, IgD or IgE antibody.

30. The Dectin-2 binding agent of claim 26, wherein the antibody is an IgG antibody.

31. The Dectin-2 binding agent of claim 26, wherein the IgG antibody comprises one or more mutations in the Fc region that result in modulated binding to one or more Fc receptors.

32. The Dectin-2 binding agent of claim 28, wherein the antibody exhibits antibody dependent cell-mediated cytotoxicity (ADCC), antibody-dependent cell-mediated phagocytosis (ADCP), or complement dependent cytotoxicity (CDC).

33. The Dectin-2 binding agent of claim 2, wherein the binding agent is, or is part of, a multispecific or bispecific antibody, chimeric antigen receptor, chimeric T cell receptor, bispecific T-cell engager, multivalent antibody, diabody, triabody, tetrabody, hexabody, bis-scFV fragment, Fab dimer, or Fab trimer.

34. The Dectin-2 binding agent of claim 3, wherein the binding agent is an antibody, an antibody conjugate, or an antigen-binding fragment thereof.

35. The Dectin-2 binding agent of claim 34, wherein the binding agent is an antibody fragment selected from F(ab')$_2$, Fab', Fab, Fv, scFv, dsFv, and a single chain binding polypeptide.

36. The Dectin-2 binding agent of claim 34, wherein the binding agent is an antibody.

37. The Dectin-2 binding agent of claim 34, wherein the antibody is an IgG, IgM, IgA, IgD or IgE antibody.

38. The Dectin-2 binding agent of claim 34, wherein the antibody is an IgG antibody.

39. The Dectin-2 binding agent of claim 38, wherein the IgG antibody comprises one or more mutations in the Fc region that result in modulated binding to one or more Fc receptors.

40. The Dectin-2 binding agent of claim 36, wherein the antibody exhibits antibody dependent cell-mediated cytotoxicity (ADCC), antibody-dependent cell-mediated phagocytosis (ADCP), or complement dependent cytotoxicity (CDC).

41. The Dectin-2 binding agent of claim 3, wherein the binding agent is, or is part of, a multispecific or bispecific antibody, chimeric antigen receptor, chimeric T cell receptor, bispecific T-cell engager, multivalent antibody, diabody, triabody, tetrabody, hexabody, bis-scFV fragment, Fab dimer, or Fab trimer.

42. The Dectin-2 binding agent of claim 4, wherein the binding agent is an antibody, an antibody conjugate, or an antigen-binding fragment thereof.

43. The Dectin-2 binding agent of claim 42, wherein the binding agent is an antibody fragment selected from F(ab')$_2$, Fab', Fab, Fv, scFv, dsFv, and a single chain binding polypeptide.

44. The Dectin-2 binding agent of claim 42, wherein the binding agent is an antibody.

45. The Dectin-2 binding agent of claim 42, wherein the antibody is an IgG, IgM, IgA, IgD or IgE antibody.

46. The Dectin-2 binding agent of claim 42, wherein the antibody is an IgG antibody.

47. The Dectin-2 binding agent of claim 46, wherein the IgG antibody comprises one or more mutations in the Fc region that result in modulated binding to one or more Fc receptors.

48. The Dectin-2 binding agent of claim 42, wherein the antibody exhibits antibody dependent cell-mediated cytotoxicity (ADCC), antibody-dependent cell-mediated phagocytosis (ADCP), or complement dependent cytotoxicity (CDC).

49. The Dectin-2 binding agent of claim 4, wherein the binding agent is, or is part of, a multispecific or bispecific antibody, chimeric antigen receptor, chimeric T cell receptor, bispecific T-cell engager, multivalent antibody, diabody, triabody, tetrabody, hexabody, bis-scFV fragment, Fab dimer, or Fab trimer.

50. The Dectin-2 binding agent of claim 46, wherein the IgG antibody is an IgG1 antibody comprising a Fc region with alanine at position 236.

51. The Dectin-2 binding agent of claim 50, wherein the Fc region of the IgG1 antibody is afucosylated.

52. The Dectin-2 binding agent of claim 46, wherein the IgG antibody is an IgG1 antibody comprising a Fc region that is afucosylated.

53. The method of claim 16, wherein the cancer is breast cancer.

54. The method of claim 53, wherein the breast cancer is triple-negative breast cancer.

55. The method of claim 16, wherein the cancer is colorectal cancer.

56. The method of claim 16, wherein the cancer is non-small cell lung cancer.

57. The method of claim 21, wherein the cancer is ovarian cancer.

58. The method of claim 16, wherein the cancer is pancreatic ductal adenocarcinoma.

59. The method of claim 16, wherein the cancer is renal cell carcinoma.

60. A method for enhancing an immune response in a mammal, the method comprising administering the Dectin-2 binding agent of claim 9 to the mammal, wherein the mammal has a cancer selected from the group consisting of head and neck squamous cell carcinoma, breast cancer, colorectal cancer, non-small cell lung cancer, ovarian cancer, pancreatic ductal adenocarcinoma, and renal cell carcinoma.

61. The method of claim 60, wherein the immune response is an anti-tumor immune response.

62. A method for treating a disease, disorder, or condition in a mammal that is responsive to Dectin-2 binding or activation, the method comprising administering the Dectin-2 binding agent of claim 9 to the mammal, wherein the disease, disorder, or condition is a cancer selected from the group consisting of head and neck squamous cell carcinoma, breast cancer, colorectal cancer, non-small cell lung cancer, ovarian cancer, pancreatic ductal adenocarcinoma, and renal cell carcinoma.

63. The method of claim 62, wherein the cancer is head and neck squamous cell carcinoma.

64. The method of claim 62, wherein the cancer is breast cancer.

65. The method of claim 64, wherein the breast cancer is triple-negative breast cancer.

66. The method of claim 62, wherein the cancer is colorectal cancer.

67. The method of claim 62, wherein the cancer is non-small cell lung cancer.

68. The method of claim 62, wherein the cancer is ovarian cancer.

69. The method of claim 62, wherein the cancer is pancreatic ductal adenocarcinoma.

70. The method of claim 62, wherein the cancer is renal cell carcinoma.

71. A method of stimulating an antigen presenting cell (APC) in a mammal having a cancer selected from the group consisting of head and neck squamous cell carcinoma, breast cancer, colorectal cancer, non-small cell lung cancer, ovarian cancer, pancreatic ductal adenocarcinoma, and renal cell carcinoma, the method comprising contacting an APC with a Dectin-2 binding agent of claim 9 at a dose and for a period of time sufficient to enhance Dectin-2 signaling in the APC, thereby generating a stimulated APC.

72. The method according to claim 71, wherein the APC is a cell of myeloid lineage.

73. The method according to claim 72, wherein the myeloid cell is a monocyte, macrophage, or a dendritic cell.

74. The method according to claim 71, wherein the stimulated APC produces at least one pro-inflammatory cytokine and/or exhibits increased phagocytosis as compared to an APC that has not been contacted by a Dectin-2 binding agent.

75. The method according to claim 74, wherein the at least one pro-inflammatory cytokine is selected from the group consisting of TNFα, IL-1β, IL-2, IL-6, IL-23p19, IFNγ, IL-12p40, and IL-12p70.

76. The method according to claim 71, comprising contacting the stimulated APC with a cancer antigen to produce an antigen-contacted APC.

77. The method according to claim 76, wherein the cancer antigen is present in a cancer cell lysate or is part of a cancer cell.

78. A method for enhancing an immune response in a mammal, the method comprising administering the Dectin-2 binding agent of claim 50 to the mammal, wherein the mammal has a cancer selected from the group consisting of head and neck squamous cell carcinoma, breast cancer, colorectal cancer, non-small cell lung cancer, ovarian cancer, pancreatic ductal adenocarcinoma, and renal cell carcinoma.

79. The method of claim 78, wherein the immune response is an anti-tumor immune response.

80. A method for treating a disease, disorder, or condition in a mammal that is responsive to Dectin-2 binding or activation, the method comprising administering the Dectin-2 binding agent of claim 50 to the mammal, wherein the disease, disorder, or condition is a cancer selected from the group consisting of head and neck squamous cell carcinoma, breast cancer, colorectal cancer, non-small cell lung cancer, ovarian cancer, pancreatic ductal adenocarcinoma, and renal cell carcinoma.

81. The method of claim 80, wherein the cancer is head and neck squamous cell carcinoma.

82. The method of claim 80, wherein the cancer is breast cancer.

83. The method of claim 82, wherein the breast cancer is triple-negative breast cancer.

84. The method of claim 80, wherein the cancer is colorectal cancer.

85. The method of claim 80, wherein the cancer is non-small cell lung cancer.

86. The method of claim 80, wherein the cancer is ovarian cancer.

87. The method of claim 80, wherein the cancer is pancreatic ductal adenocarcinoma.

88. The method of claim 80, wherein the cancer is renal cell carcinoma.

89. A method of stimulating an antigen presenting cell (APC) in a mammal having a cancer selected from the group consisting of head and neck squamous cell carcinoma, breast cancer, colorectal cancer, non-small cell lung cancer, ovarian cancer, pancreatic ductal adenocarcinoma, and renal cell carcinoma, the method comprising contacting an APC with a Dectin-2 binding agent of claim 50 at a dose and for a period of time sufficient to enhance Dectin-2 signaling in the APC, thereby generating a stimulated APC.

90. The method according to claim 89, wherein the APC is a cell of myeloid lineage.

91. The method according to claim 90, wherein the myeloid cell is a monocyte, macrophage, or a dendritic cell.

92. The method according to claim 89, wherein the stimulated APC produces at least one pro-inflammatory cytokine and/or exhibits increased phagocytosis as compared to an APC that has not been contacted by a Dectin-2 binding agent.

93. The method according to claim 92, wherein the at least one pro-inflammatory cytokine is selected from the group consisting of TNFα, IL-1β, IL-2, IL-6, IL-23p19, IFNγ, IL-12p40, and IL-12p70.

94. The method according to claim 89, comprising contacting the stimulated APC with a cancer antigen to produce an antigen-contacted APC.

95. The method according to claim 94, wherein the cancer antigen is present in a cancer cell lysate or is part of a cancer cell.

96. A method for enhancing an immune response in a mammal, the method comprising administering the Dectin-2 binding agent of claim 51 to the mammal, wherein the mammal has a cancer selected from the group consisting of head and neck squamous cell carcinoma, breast cancer, colorectal cancer, non-small cell lung cancer, ovarian cancer, pancreatic ductal adenocarcinoma, and renal cell carcinoma.

97. The method of claim 96, wherein the immune response is an anti-tumor immune response.

98. A method for treating a disease, disorder, or condition in a mammal that is responsive to Dectin-2 binding or activation, the method comprising administering the Dectin-2 binding agent of claim 51 to the mammal, wherein the disease, disorder, or condition is a cancer selected from the group consisting of head and neck squamous cell carcinoma, breast cancer, colorectal cancer, non-small cell lung cancer, ovarian cancer, pancreatic ductal adenocarcinoma, and renal cell carcinoma.

99. The method of claim 98, wherein the cancer is head and neck squamous cell carcinoma.

100. The method of claim 98, wherein the cancer is breast cancer.

101. The method of claim 98, wherein the breast cancer is triple-negative breast cancer.

102. The method of claim 98, wherein the cancer is colorectal cancer.

103. The method of claim 98, wherein the cancer is non-small cell lung cancer.

104. The method of claim 98, wherein the cancer is ovarian cancer.

105. The method of claim 98, wherein the cancer is pancreatic ductal adenocarcinoma.

106. The method of claim 98, wherein the cancer is renal cell carcinoma.

107. A method of stimulating an antigen presenting cell (APC) in a mammal having a cancer selected from the group consisting of head and neck squamous cell carcinoma, breast cancer, colorectal cancer, non-small cell lung cancer, ovarian cancer, pancreatic ductal adenocarcinoma, and renal cell carcinoma, the method comprising contacting an APC with a Dectin-2 binding agent of claim 51 at a dose and for a period of time sufficient to enhance Dectin-2 signaling in the APC, thereby generating a stimulated APC.

108. The method according to claim 107, wherein the APC is a cell of myeloid lineage.

109. The method according to claim 108, wherein the myeloid cell is a monocyte, macrophage, or a dendritic cell.

110. The method according to claim 107, wherein the stimulated APC produces at least one pro-inflammatory cytokine and/or exhibits increased phagocytosis as compared to an APC that has not been contacted by a Dectin-2 binding agent.

111. The method according to claim 110, wherein the at least one pro inflammatory cytokine is selected from the group consisting of TNFα, IL-1β, IL-2, IL-6, IL-23p19, IFNγ, IL-12p40, and IL-12p70.

112. The method according to claim 107, comprising contacting the stimulated APC with a cancer antigen to produce an antigen-contacted APC.

113. The method according to claim 112, wherein the cancer antigen is present in a cancer cell lysate or is part of a cancer cell.

114. A method for enhancing an immune response in a mammal, the method comprising administering the Dectin-2 binding agent of claim 52 to the mammal, wherein the mammal has a cancer selected from the group consisting of head and neck squamous cell carcinoma, breast cancer, colorectal cancer, non-small cell lung cancer, ovarian cancer, pancreatic ductal adenocarcinoma, and renal cell carcinoma.

115. The method of claim 114, wherein the immune response is an anti-tumor immune response.

116. A method for treating a disease, disorder, or condition in a mammal that is responsive to Dectin-2 binding or activation, the method comprising administering the Dectin-2 binding agent of claim 52 to the mammal, wherein the disease, disorder, or condition is a cancer selected from the group consisting of head and neck squamous cell carcinoma, breast cancer, colorectal cancer, non-small cell lung cancer, ovarian cancer, pancreatic ductal adenocarcinoma, and renal cell carcinoma.

117. The method of claim 116, wherein the cancer is head and neck squamous cell carcinoma.

118. The method of claim 116, wherein the cancer is breast cancer.

119. The method of claim 118, wherein the breast cancer is triple-negative breast cancer.

120. The method of claim 116, wherein the cancer is colorectal cancer.

121. The method of claim 116, wherein the cancer is non-small cell lung cancer.

122. The method of claim 116, wherein the cancer is ovarian cancer.

123. The method of claim 116, wherein the cancer is pancreatic ductal adenocarcinoma.

124. The method of claim 116, wherein the cancer is renal cell carcinoma.

125. A method of stimulating an antigen presenting cell (APC) in a mammal having a cancer selected from the group consisting of head and neck squamous cell carcinoma, breast cancer, colorectal cancer, non-small cell lung cancer, ovarian cancer, pancreatic ductal adenocarcinoma, and renal cell carcinoma, the method comprising contacting an APC with a Dectin-2 binding agent of claim 52 at a dose and for a period of time sufficient to enhance Dectin-2 signaling in the APC, thereby generating a stimulated APC.

126. The method according to claim 125, wherein the APC is a cell of myeloid lineage.

127. The method according to claim 126, wherein the myeloid cell is a monocyte, macrophage, or a dendritic cell.

128. The method according to claim 125, wherein the stimulated APC produces at least one pro-inflammatory cytokine and/or exhibits increased phagocytosis as compared to an APC that has not been contacted by a Dectin-2 binding agent.

129. The method according to claim 128, wherein the at least one pro inflammatory cytokine is selected from the group consisting of TNFα, IL-1β, IL-2, IL-6, IL-23p19, IFNγ, IL-12p40, and IL-12p70.

130. The method according to claim 125, comprising contacting the stimulated APC with a cancer antigen to produce an antigen-contacted APC.

131. The method according to claim 130, wherein the cancer antigen is present in a cancer cell lysate or is part of a cancer cell.

* * * * *

UNITED STATES PATENT AND TRADEMARK OFFICE
CERTIFICATE OF CORRECTION

PATENT NO. : 11,753,474 B2  
APPLICATION NO. : 17/592323  
DATED : September 12, 2023  
INVENTOR(S) : Ackerman et al.

Page 1 of 1

It is certified that error appears in the above-identified patent and that said Letters Patent is hereby corrected as shown below:

In the Claims

Claim 3, Column 271, Line 9, "901%" should be -- 90% --

Claim 8, Column 271, Line 27, "TgM" should be -- IgM --

Claim 23, Column 272, Line 23, "IL-10, IL-2, IL-4" should be -- IL-1β, IL-2, IL-6 --

Claim 31, Column 272, Line 44, "claim 26" should be -- claim 30 --

Claim 57, Column 273, Line 64, "claim 21" should be -- claim 16 --

Claim 101, Column 276, Line 20, "claim 98" should be -- claim 100 --

Signed and Sealed this  
Twenty-eighth Day of November, 2023

Katherine Kelly Vidal  
*Director of the United States Patent and Trademark Office*

SEQUENCE LISTING

```
<160> NUMBER OF SEQ ID NOS: 346

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ser Tyr Tyr Met Gln
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Thr Tyr Tyr Met His
1               5
```

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Asn Phe Gly Ile Asn
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Ser Tyr Asp Ile Asn
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic

<400> SEQUENCE: 5

Gly Tyr Tyr Val His
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Ser Tyr Trp Met Ser
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Ser Gln Tyr Met His
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic

<400> SEQUENCE: 8

Thr Tyr Tyr Met Asn
1               5

```
<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Ser Tyr Phe Met His
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Thr Trp Tyr Met Gln
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic

<400> SEQUENCE: 11

Ser Tyr Ala Ile Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Arg Tyr Tyr Leu His
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic

<400> SEQUENCE: 13

Gly Gln Trp Val His
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic

<400> SEQUENCE: 14

Pro Asn Tyr Ile Gln
1               5
```

```
<210> SEQ ID NO 15
<211> LENGTH: 5
<212> TYPE: PRT
<213> ORGANISM: Artificial Sequence
<220> FEATURE:
<223> OTHER INFORMATION: Synthetic

<400> SEQUENCE: 15

Ala Ser Tyr Ile His
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic

<400> SEQUENCE: 16

Asp Ser His Leu His
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic

<400> SEQUENCE: 17

Ser Tyr Trp Met His
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic

<400> SEQUENCE: 18

Asn Tyr Trp Ile Gln
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic

<400> SEQUENCE: 19

Asn Tyr Tyr Met His
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic

<400> SEQUENCE: 20

Gly Tyr Asp Met Gln
1               5

<210> SEQ ID NO 21
```

```
<211> LENGTH: 5
<212> TYPE: PRT
<213> ORGANISM: Artificial Sequence
<220> FEATURE:
<223> OTHER INFORMATION: Synthetic

<400> SEQUENCE: 21

Ser Tyr Ser Met Asn
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic

<400> SEQUENCE: 22

Gly Tyr Tyr Ile His
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic

<400> SEQUENCE: 23

Ser Tyr Ala Met His
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic

<400> SEQUENCE: 24

Asn Tyr Gly Ile Thr
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic

<400> SEQUENCE: 25

Gly Tyr Tyr Met His
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic

<400> SEQUENCE: 26

Asn Tyr Tyr Ile His
1               5

<210> SEQ ID NO 27
<211> LENGTH: 5
```

```
<212> TYPE: PRT
<213> ORGANISM: Artificial Sequence
<220> FEATURE:
<223> OTHER INFORMATION: Synthetic

<400> SEQUENCE: 27

Asp Tyr Gly Met Tyr
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic

<400> SEQUENCE: 28

Ser Tyr Gly Ile Asn
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic

<400> SEQUENCE: 29

Ser Tyr Gly Ile Ser
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic

<400> SEQUENCE: 30

Ser Tyr Tyr Met His
1               5

<210> SEQ ID NO 31
<211> LENGTH: 17
<212> TYPE: PRT
<213> ORGANISM: Artificial Sequence
<220> FEATURE:
<223> OTHER INFORMATION: Synthetic

<400> SEQUENCE: 31

Trp Ile Asn Pro Lys Ser Gly Gly Thr Asn Tyr Ala Gln Lys Phe Gln
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: Synthetic

<400> SEQUENCE: 32

Ile Ile Asn Pro Ser Gly Gly Ser Thr Ser Tyr Ala Gln Lys Phe Gln
1               5                   10                  15

Gly
```

```
<210> SEQ ID NO 33
<211> LENGTH: 17
<212> TYPE: PRT
<213> ORGANISM: Artificial Sequence
<220> FEATURE:
<223> OTHER INFORMATION: Synthetic

<400> SEQUENCE: 33

Trp Ile Asn Pro Asn Ser Gly Gly Ala Asn Tyr Ala Gln Lys Phe Gln
1               5                   10                  15

Gly

<210> SEQ ID NO 34
<211> LENGTH: 17
<212> TYPE: PRT
<213> ORGANISM: Artificial Sequence
<220> FEATURE:
<223> OTHER INFORMATION: Synthetic

<400> SEQUENCE: 34

Trp Ile Asn Pro Asn Ser Gly Ala Thr Asn Ser Ala Gln Lys Phe Gln
1               5                   10                  15

Gly

<210> SEQ ID NO 35
<211> LENGTH: 17
<212> TYPE: PRT
<213> ORGANISM: Artificial Sequence
<220> FEATURE:
<223> OTHER INFORMATION: Synthetic

<400> SEQUENCE: 35

Ile Ile His Pro Asn Gly Gly Ser Thr Ser Tyr Ala Gln Lys Phe Gln
1               5                   10                  15

Gly

<210> SEQ ID NO 36
<211> LENGTH: 17
<212> TYPE: PRT
<213> ORGANISM: Artificial Sequence
<220> FEATURE:
<223> OTHER INFORMATION: Synthetic

<400> SEQUENCE: 36

Asp Ile Ser Gly Ser Gly Arg Ser Thr Tyr Tyr Ala Asp Ser Val Lys
1               5                   10                  15

Gly

<210> SEQ ID NO 37
<211> LENGTH: 17
<212> TYPE: PRT
<213> ORGANISM: Artificial Sequence
<220> FEATURE:
<223> OTHER INFORMATION: Synthetic

<400> SEQUENCE: 37

Ala Ile Ser Gly Ser Gly Gly Ser Thr Tyr Tyr Ala Asp Ser Val Lys
1               5                   10                  15

Gly

<210> SEQ ID NO 38
<211> LENGTH: 17
<212> TYPE: PRT
```

<213> ORGANISM: Artificial Sequence
<220> FEATURE:
<223> OTHER INFORMATION: Synthetic

<400> SEQUENCE: 38

Trp Met Asn Pro Asn Ser Gly Asn Thr Gly Tyr Ala Gln Lys Phe Gln
1               5                   10                  15

Gly

<210> SEQ ID NO 39
<211> LENGTH: 17
<212> TYPE: PRT
<213> ORGANISM: Artificial Sequence
<220> FEATURE:
<223> OTHER INFORMATION: Synthetic

<400> SEQUENCE: 39

Ile Leu Ser Pro Ser Gly Gly Thr Ser Tyr Ala Pro Lys Phe Gln
1               5                   10                  15

Gly

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Trp Met Asn Pro Asn Asn Gly Asn Thr Gly Tyr Ala Gln Lys Phe Gln
1               5                   10                  15

Gly

<210> SEQ ID NO 41
<211> LENGTH: 17
<212> TYPE: PRT
<213> ORGANISM: Artificial Sequence
<220> FEATURE:
<223> OTHER INFORMATION: Synthetic

<400> SEQUENCE: 41

Trp Ile Ser Pro Tyr Thr Gly Asn Thr Ile Tyr Ala Pro Asn Val Gln
1               5                   10                  15

Gly

<210> SEQ ID NO 42
<211> LENGTH: 17
<212> TYPE: PRT
<213> ORGANISM: Artificial Sequence
<220> FEATURE:
<223> OTHER INFORMATION: Synthetic

<400> SEQUENCE: 42

Trp Ile Ser Thr Tyr Asn Gly Asn Thr Asn Tyr Ala Gln Lys Phe Gln
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: Synthetic

```
<400> SEQUENCE: 43

Arg Ile Ile Pro Ile Leu Gly Ile Ala Asn Tyr Ala Gln Lys Phe Gln
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: Synthetic

<400> SEQUENCE: 44

Leu Ile Ser Tyr Asp Gly Gly Ser Thr Tyr Tyr Ala Asp Ser Val Lys
1               5                   10                  15

Gly

<210> SEQ ID NO 45
<211> LENGTH: 17
<212> TYPE: PRT
<213> ORGANISM: Artificial Sequence
<220> FEATURE:
<223> OTHER INFORMATION: Synthetic

<400> SEQUENCE: 45

Ile Ile Asn Pro Ser Gly Arg Ser Thr Ser Tyr Ala Gln Lys Phe Gln
1               5                   10                  15

Gly

<210> SEQ ID NO 46
<211> LENGTH: 17
<212> TYPE: PRT
<213> ORGANISM: Artificial Sequence
<220> FEATURE:
<223> OTHER INFORMATION: Synthetic

<400> SEQUENCE: 46

Gly Ile Ile Pro Ile Phe Gly Ser Pro Asn Tyr Ala Gln Lys Phe Gln
1               5                   10                  15

Gly

<210> SEQ ID NO 47
<211> LENGTH: 16
<212> TYPE: PRT
<213> ORGANISM: Artificial Sequence
<220> FEATURE:
<223> OTHER INFORMATION: Synthetic

<400> SEQUENCE: 47

Val Ile Tyr Ala Gly Gly Ser Arg Tyr Tyr Ala Asp Ser Val Lys Gly
1               5                   10                  15

<210> SEQ ID NO 48
<211> LENGTH: 17
<212> TYPE: PRT
<213> ORGANISM: Artificial Sequence
<220> FEATURE:
<223> OTHER INFORMATION: Synthetic

<400> SEQUENCE: 48

Thr Ile Ser Gly Ser Gly Ala Gly Thr Trp Tyr Ala Asp Ser Val Lys
1               5                   10                  15

Gly
```

<210> SEQ ID NO 49
<211> LENGTH: 17
<212> TYPE: PRT
<213> ORGANISM: Artificial Sequence
<220> FEATURE:
<223> OTHER INFORMATION: Synthetic

<400> SEQUENCE: 49

Trp Ile Asn Pro Asn Ser Gly Gly Thr Arg Tyr Ala Arg Asn Phe Gln
1               5                   10                  15

Gly

<210> SEQ ID NO 50
<211> LENGTH: 16
<212> TYPE: PRT
<213> ORGANISM: Artificial Sequence
<220> FEATURE:
<223> OTHER INFORMATION: Synthetic

<400> SEQUENCE: 50

Trp Leu Asn Pro Asn Ser Gly Thr Asn Tyr Ala Gln Lys Phe Gln Gly
1               5                   10                  15

<210> SEQ ID NO 51
<211> LENGTH: 17
<212> TYPE: PRT
<213> ORGANISM: Artificial Sequence
<220> FEATURE:
<223> OTHER INFORMATION: Synthetic

<400> SEQUENCE: 51

Ile Ile Asn Pro Ser Gly Ala Gly Thr Asn Tyr Ala Gln Lys Phe Gln
1               5                   10                  15

Gly

<210> SEQ ID NO 52
<211> LENGTH: 17
<212> TYPE: PRT
<213> ORGANISM: Artificial Sequence
<220> FEATURE:
<223> OTHER INFORMATION: Synthetic

<400> SEQUENCE: 52

Val Ile Ser Tyr Asp Gly Arg Ile Lys Asp Tyr Ala Asp Ser Val Lys
1               5                   10                  15

Gly

<210> SEQ ID NO 53
<211> LENGTH: 17
<212> TYPE: PRT
<213> ORGANISM: Artificial Sequence
<220> FEATURE:
<223> OTHER INFORMATION: Synthetic

<400> SEQUENCE: 53

Gly Ile Ser Trp Asn Gly Gly Lys Thr His Tyr Ala Asp Ser Val Lys
1               5                   10                  15

Gly

<210> SEQ ID NO 54
<211> LENGTH: 17
<212> TYPE: PRT
<213> ORGANISM: Artificial Sequence
<220> FEATURE:
<223> OTHER INFORMATION: Synthetic

<400> SEQUENCE: 54

Gly Thr Ser Leu Asp Gly Asn Lys Asn Tyr Tyr Ala Asp Ser Val Lys
1               5                   10                  15
Gly

<210> SEQ ID NO 55
<211> LENGTH: 17
<212> TYPE: PRT
<213> ORGANISM: Artificial Sequence
<220> FEATURE:
<223> OTHER INFORMATION: Synthetic

<400> SEQUENCE: 55

Thr Ile Ser Gly Ser Gly Gly Thr Thr Tyr Tyr Ala Asp Ser Val Lys
1               5                   10                  15
Gly

<210> SEQ ID NO 56
<211> LENGTH: 17
<212> TYPE: PRT
<213> ORGANISM: Artificial Sequence
<220> FEATURE:
<223> OTHER INFORMATION: Synthetic

<400> SEQUENCE: 56

Trp Ile Asn Pro His Ser Gly Gly Thr Asn Tyr Ala Gln Lys Phe Gln
1               5                   10                  15
Gly

<210> SEQ ID NO 57
<211> LENGTH: 17
<212> TYPE: PRT
<213> ORGANISM: Artificial Sequence
<220> FEATURE:
<223> OTHER INFORMATION: Synthetic

<400> SEQUENCE: 57

Leu Ile Asp Pro Ser Pro Gly Thr Thr Tyr Tyr Ala Gln Lys Phe Gln
1               5                   10                  15
Gly

<210> SEQ ID NO 58
<211> LENGTH: 17
<212> TYPE: PRT
<213> ORGANISM: Artificial Sequence
<220> FEATURE:
<223> OTHER INFORMATION: Synthetic

<400> SEQUENCE: 58

Arg Ile Asn Pro Asn Ser Gly Gly Thr Asn Phe Ala Gln Lys Phe Gln
1               5                   10                  15
Gly

<210> SEQ ID NO 59
<211> LENGTH: 17
<212> TYPE: PRT
<213> ORGANISM: Artificial Sequence
<220> FEATURE:
<223> OTHER INFORMATION: Synthetic

```
<400> SEQUENCE: 59

Trp Met Asn Pro Asn Ser Ala Asn Thr Gly Tyr Ala Gln Lys Phe Gln
1               5                   10                  15

Gly

<210> SEQ ID NO 60
<211> LENGTH: 17
<212> TYPE: PRT
<213> ORGANISM: Artificial Sequence
<220> FEATURE:
<223> OTHER INFORMATION: Synthetic

<400> SEQUENCE: 60

Val Ile Asn Pro Ser Gly Gly Gly Thr Thr Tyr Ala Lys Lys Phe Gln
1               5                   10                  15

Gly

<210> SEQ ID NO 61
<211> LENGTH: 17
<212> TYPE: PRT
<213> ORGANISM: Artificial Sequence
<220> FEATURE:
<223> OTHER INFORMATION: Synthetic

<400> SEQUENCE: 61

Trp Ile Asn Pro Asp Ser Gly Asp Thr Asn Phe Ala Gln Lys Phe Gln
1               5                   10                  15

Gly

<210> SEQ ID NO 62
<211> LENGTH: 17
<212> TYPE: PRT
<213> ORGANISM: Artificial Sequence
<220> FEATURE:
<223> OTHER INFORMATION: Synthetic

<400> SEQUENCE: 62

Tyr Ile Ser Ser Ser Gly Ser Thr Ile Tyr Tyr Ala Asp Ser Val Lys
1               5                   10                  15

Gly

<210> SEQ ID NO 63
<211> LENGTH: 17
<212> TYPE: PRT
<213> ORGANISM: Artificial Sequence
<220> FEATURE:
<223> OTHER INFORMATION: Synthetic

<400> SEQUENCE: 63

Arg Ile Ile Pro Ile Phe Gly Ala Ala Asn Tyr Ala Gln Lys Phe Gln
1               5                   10                  15

Gly

<210> SEQ ID NO 64
<211> LENGTH: 17
<212> TYPE: PRT
<213> ORGANISM: Artificial Sequence
<220> FEATURE:
<223> OTHER INFORMATION: Synthetic
```

-continued

<400> SEQUENCE: 64

Trp Ile Asn Pro Asn Asn Gly Gly Thr Asn Tyr Ala Gln Lys Phe Gln
1               5                   10                  15
Gly

<210> SEQ ID NO 65
<211> LENGTH: 19
<212> TYPE: PRT
<213> ORGANISM: Artificial Sequence
<220> FEATURE:
<223> OTHER INFORMATION: Synthetic

<400> SEQUENCE: 65

Gly Thr Tyr Leu Arg Thr Gly Ser Ser Leu Ser Gly Tyr Tyr Gly
1               5                   10                  15
Met Asp Val

<210> SEQ ID NO 66
<211> LENGTH: 12
<212> TYPE: PRT
<213> ORGANISM: Artificial Sequence
<220> FEATURE:
<223> OTHER INFORMATION: Synthetic

<400> SEQUENCE: 66

Ser His Tyr Gly Asp Leu Asn Gly Gly Phe Asp Leu
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthetic

<400> SEQUENCE: 67

Gly Val Val Ala Ala Arg Tyr Tyr Tyr Met Asp Val
1               5                   10

<210> SEQ ID NO 68
<211> LENGTH: 17
<212> TYPE: PRT
<213> ORGANISM: Artificial Sequence
<220> FEATURE:
<223> OTHER INFORMATION: Synthetic

<400> SEQUENCE: 68

Ala Gly Tyr Ser Ser Ser Trp Asp Gly Tyr Tyr Tyr Gly Met Asp
1               5                   10                  15
Val

<210> SEQ ID NO 69
<211> LENGTH: 12
<212> TYPE: PRT
<213> ORGANISM: Artificial Sequence
<220> FEATURE:
<223> OTHER INFORMATION: Synthetic

<400> SEQUENCE: 69

Asp Gln Ala Gly Thr Gly Gly His Gly Met Asp Val
1               5                   10

<210> SEQ ID NO 70

```
<211> LENGTH: 19
<212> TYPE: PRT
<213> ORGANISM: Artificial Sequence
<220> FEATURE:
<223> OTHER INFORMATION: Synthetic

<400> SEQUENCE: 70

Gly Arg Tyr Leu Glu Trp Val Leu Ser Ser Glu Asp Tyr Tyr Phe Gly
1               5                   10                  15

Met Asp Val

<210> SEQ ID NO 71
<211> LENGTH: 14
<212> TYPE: PRT
<213> ORGANISM: Artificial Sequence
<220> FEATURE:
<223> OTHER INFORMATION: Synthetic

<400> SEQUENCE: 71

Gly Arg Tyr Ser Arg Ser Trp Glu Arg Trp Tyr Phe Asp Leu
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Synthetic

<400> SEQUENCE: 72

Gly Gln Tyr Asp Ser Ser Gly Tyr Tyr Tyr Phe Asp Tyr
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Synthetic

<400> SEQUENCE: 73

Ala Thr Tyr Tyr Asp Phe Trp Ser Gly Ser Leu Asp Tyr
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic

<400> SEQUENCE: 74

Gln Ala Gly Tyr Ser Ser Gly Trp Asp Tyr
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Synthetic

<400> SEQUENCE: 75

Ala Val Tyr Asp Ile Leu Thr Gly Ala Tyr Tyr Phe Asp Tyr
1               5                   10
```

```
<210> SEQ ID NO 76
<211> LENGTH: 12
<212> TYPE: PRT
<213> ORGANISM: Artificial Sequence
<220> FEATURE:
<223> OTHER INFORMATION: Synthetic

<400> SEQUENCE: 76

Gly Arg Leu Pro Pro Tyr Tyr Tyr Gly Met Asp Val
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Synthetic

<400> SEQUENCE: 77

Met Ala Thr Val Thr Lys His Thr Tyr Trp Tyr Phe Asp Leu
1               5                   10

<210> SEQ ID NO 78
<211> LENGTH: 15
<212> TYPE: PRT
<213> ORGANISM: Artificial Sequence
<220> FEATURE:
<223> OTHER INFORMATION: Synthetic

<400> SEQUENCE: 78

Ala Gly Arg Ser Thr Ser Arg Tyr Tyr Tyr Tyr Met Asp Val
1               5                   10                  15

<210> SEQ ID NO 79
<211> LENGTH: 12
<212> TYPE: PRT
<213> ORGANISM: Artificial Sequence
<220> FEATURE:
<223> OTHER INFORMATION: Synthetic

<400> SEQUENCE: 79

Ser Ser Ser Gly Tyr Thr Thr Asp Ala Phe Asp Ile
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic

<400> SEQUENCE: 80

Glu Tyr Gln Leu Met Asn Val Gly Met Asp Val
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthetic

<400> SEQUENCE: 81

Gly Lys Gln Arg Ala Asp Ala Phe Asp Ile
1               5                   10

<210> SEQ ID NO 82
```

```
<211> LENGTH: 15
<212> TYPE: PRT
<213> ORGANISM: Artificial Sequence
<220> FEATURE:
<223> OTHER INFORMATION: Synthetic

<400> SEQUENCE: 82

Asp Val Asp Pro Ser Arg Gln Ser Tyr Tyr His Gly Val Asp Val
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Synthetic

<400> SEQUENCE: 83

Gly Arg Tyr Tyr Tyr Gly Ser Gly Ser Gln Tyr His Ala Phe Asp Ile
1               5                   10                  15

<210> SEQ ID NO 84
<211> LENGTH: 13
<212> TYPE: PRT
<213> ORGANISM: Artificial Sequence
<220> FEATURE:
<223> OTHER INFORMATION: Synthetic

<400> SEQUENCE: 84

Gly Arg Tyr Asp Ser Ser Gly Tyr Tyr Tyr Phe Asp Tyr
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Synthetic

<400> SEQUENCE: 85

Thr Val Thr Thr Pro Tyr Gln Tyr Tyr Gly Met Asp Val
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic

<400> SEQUENCE: 86

Val Arg Gly Phe Ser Phe Trp Phe Asp Pro
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Synthetic

<400> SEQUENCE: 87

Gly Gly Gly Tyr Phe Asp Tyr
1               5

<210> SEQ ID NO 88
<211> LENGTH: 19
```

```
<212> TYPE: PRT
<213> ORGANISM: Artificial Sequence
<220> FEATURE:
<223> OTHER INFORMATION: Synthetic

<400> SEQUENCE: 88

Gly Arg Tyr Gly Ser Ser Gly Trp Ser Pro Tyr Tyr Tyr Tyr
1               5                   10                  15

Met Asp Val

<210> SEQ ID NO 89
<211> LENGTH: 12
<212> TYPE: PRT
<213> ORGANISM: Artificial Sequence
<220> FEATURE:
<223> OTHER INFORMATION: Synthetic

<400> SEQUENCE: 89

Ala Arg Asp Ser Gly Ser Pro Lys Asp Phe Asp Tyr
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Synthetic

<400> SEQUENCE: 90

Gly Thr Met Ala Arg Gly Ser
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic

<400> SEQUENCE: 91

Ala Thr Asp Tyr Pro Gly Met Asp Val
1               5

<210> SEQ ID NO 92
<211> LENGTH: 18
<212> TYPE: PRT
<213> ORGANISM: Artificial Sequence
<220> FEATURE:
<223> OTHER INFORMATION: Synthetic

<400> SEQUENCE: 92

Gly Arg Met His Tyr Asp Ser Ser Val His Tyr Tyr Tyr Gly Met
1               5                   10                  15

Asp Val

<210> SEQ ID NO 93
<211> LENGTH: 16
<212> TYPE: PRT
<213> ORGANISM: Artificial Sequence
<220> FEATURE:
<223> OTHER INFORMATION: Synthetic

<400> SEQUENCE: 93

Val Ser Ile Val Gly Ala Thr Pro Asp Tyr Tyr Tyr Gly Met Asp Val
1               5                   10                  15
```

<210> SEQ ID NO 94
<211> LENGTH: 9
<212> TYPE: PRT
<213> ORGANISM: Artificial Sequence
<220> FEATURE:
<223> OTHER INFORMATION: Synthetic

<400> SEQUENCE: 94

Val Ile Arg Gly Gly Lys Phe Asp Pro
1               5

<210> SEQ ID NO 95
<211> LENGTH: 16
<212> TYPE: PRT
<213> ORGANISM: Artificial Sequence
<220> FEATURE:
<223> OTHER INFORMATION: Synthetic

<400> SEQUENCE: 95

Gly Leu Tyr Ala Ala Ala Gly Asp Gln Tyr Tyr Tyr Gly Met Asp Val
1               5                   10                  15

<210> SEQ ID NO 96
<211> LENGTH: 6
<212> TYPE: PRT
<213> ORGANISM: Artificial Sequence
<220> FEATURE:
<223> OTHER INFORMATION: Synthetic

<400> SEQUENCE: 96

Gly Ala Ala Phe Asp Tyr
1               5

<210> SEQ ID NO 97
<211> LENGTH: 14
<212> TYPE: PRT
<213> ORGANISM: Artificial Sequence
<220> FEATURE:
<223> OTHER INFORMATION: Synthetic

<400> SEQUENCE: 97

Glu Tyr Gly Asp Tyr Gly Tyr Tyr Tyr Gly Met Asp Val
1               5                   10

<210> SEQ ID NO 98
<211> LENGTH: 18
<212> TYPE: PRT
<213> ORGANISM: Artificial Sequence
<220> FEATURE:
<223> OTHER INFORMATION: Synthetic

<400> SEQUENCE: 98

Gly Ile Tyr Tyr Tyr Asp Ser Ser Gly Gly Ser Tyr Tyr Tyr Gly Met
1               5                   10                  15

Asp Val

<210> SEQ ID NO 99
<211> LENGTH: 13
<212> TYPE: PRT
<213> ORGANISM: Artificial Sequence
<220> FEATURE:
<223> OTHER INFORMATION: Synthetic

<400> SEQUENCE: 99

Glu Leu Ser Ser Ser Trp Tyr Ser Tyr Gly Met Asp Val
1               5                   10

```
<210> SEQ ID NO 100
<211> LENGTH: 10
<212> TYPE: PRT
<213> ORGANISM: Artificial Sequence
<220> FEATURE:
<223> OTHER INFORMATION: Synthetic

<400> SEQUENCE: 100

Val Ser Gly Gly Ser Trp Tyr Asp Arg Leu
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Synthetic

<400> SEQUENCE: 101

Thr Tyr Phe Asp Trp Phe Phe Phe Asp Tyr
1               5                   10

<210> SEQ ID NO 102
<211> LENGTH: 16
<212> TYPE: PRT
<213> ORGANISM: Artificial Sequence
<220> FEATURE:
<223> OTHER INFORMATION: Synthetic

<400> SEQUENCE: 102

Gly Arg Tyr Ser Gly His Phe Gly Val Tyr Tyr Tyr Gly Met Asp Val
1               5                   10                  15

<210> SEQ ID NO 103
<211> LENGTH: 10
<212> TYPE: PRT
<213> ORGANISM: Artificial Sequence
<220> FEATURE:
<223> OTHER INFORMATION: Synthetic

<400> SEQUENCE: 103

Glu Pro Tyr Gly Asp Tyr Gly Phe Asp Tyr
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetic

<400> SEQUENCE: 104

Gln Ala Ser Gln Asp Ile Ser Asn Tyr Leu Asn
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Synthetic

<400> SEQUENCE: 105

Arg Ala Ser Gln Tyr Ile Ser Ser Tyr Leu Ala
1               5                   10
```

<210> SEQ ID NO 106
<211> LENGTH: 11
<212> TYPE: PRT
<213> ORGANISM: Artificial Sequence
<220> FEATURE:
<223> OTHER INFORMATION: Synthetic

<400> SEQUENCE: 106

Arg Ala Ser Gln Asn Ile Gly Ser Tyr Leu Asn
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Synthetic

<400> SEQUENCE: 107

Arg Ala Ser Gln Ser Ile Ser Ser His Leu Asn
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetic

<400> SEQUENCE: 108

Arg Ala Ser Gln Ser Ile Asn Asn Trp Leu Ala
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Synthetic

<400> SEQUENCE: 109

Gln Ala Ser Gln Asp Ile Arg Asn Tyr Leu Asn
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic

<400> SEQUENCE: 110

Arg Ala Ser Gln Ser Ile Ser Ser Tyr Leu Asn
1               5                   10

<210> SEQ ID NO 111
<211> LENGTH: 17
<212> TYPE: PRT
<213> ORGANISM: Artificial Sequence
<220> FEATURE:
<223> OTHER INFORMATION: Synthetic

<400> SEQUENCE: 111

Lys Ser Ser Gln Ser Val Leu Tyr Ser Ser Asn Asn Lys Asn Tyr Leu
1               5                   10                  15

Ala

<210> SEQ ID NO 112
<211> LENGTH: 11
<212> TYPE: PRT
<213> ORGANISM: Artificial Sequence
<220> FEATURE:
<223> OTHER INFORMATION: Synthetic

<400> SEQUENCE: 112

Arg Ala Ser Glu Asn Ile Gly Asn Trp Leu Ala
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Synthetic

<400> SEQUENCE: 113

Arg Ala Ser Gln Ser Val Ser Ser Asn Leu Ala
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Synthetic

<400> SEQUENCE: 114

Arg Ala Ser Gln Gly Ile Ser Asn Asn Leu Asn
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Synthetic

<400> SEQUENCE: 115

Arg Ala Ser Gln Ser Ile Ser Lys Phe Leu Asn
1               5                   10

<210> SEQ ID NO 116
<211> LENGTH: 16
<212> TYPE: PRT
<213> ORGANISM: Artificial Sequence
<220> FEATURE:
<223> OTHER INFORMATION: Synthetic

<400> SEQUENCE: 116

Arg Ser Ser Gln Ser Leu Leu His Ser Asn Gly Tyr Asn Tyr Leu Asp
1               5                   10                  15

<210> SEQ ID NO 117
<211> LENGTH: 11
<212> TYPE: PRT
<213> ORGANISM: Artificial Sequence
<220> FEATURE:
<223> OTHER INFORMATION: Synthetic

<400> SEQUENCE: 117

Arg Ala Ser Gln Ser Ile Gly Ser Tyr Leu Asn
1               5                   10

```
<210> SEQ ID NO 118
<211> LENGTH: 11
<212> TYPE: PRT
<213> ORGANISM: Artificial Sequence
<220> FEATURE:
<223> OTHER INFORMATION: Synthetic

<400> SEQUENCE: 118

Gln Ala Ser Gln Glu Ile Gly Asn Tyr Leu Asn
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Synthetic

<400> SEQUENCE: 119

Gln Ala Ser Gln Asp Ile Thr Asn Phe Leu Asn
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Synthetic

<400> SEQUENCE: 120

Arg Ala Ser Gln Ser Ile Ser Thr Phe Leu Asn
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Synthetic

<400> SEQUENCE: 121

Gln Ala Ser Gln Asp Ile Ser Lys Tyr Leu Asn
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Synthetic

<400> SEQUENCE: 122

Gln Ala Ser Gln Asp Ile Gly Asn Tyr Leu Asn
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Synthetic

<400> SEQUENCE: 123

Arg Ala Ser Gln Asp Ile Arg Asn Tyr Leu Ala
1               5                   10
```

-continued

```
<210> SEQ ID NO 124
<211> LENGTH: 11
<212> TYPE: PRT
<213> ORGANISM: Artificial Sequence
<220> FEATURE:
<223> OTHER INFORMATION: Synthetic

<400> SEQUENCE: 124

Arg Ala Ser Gln Ser Ile Ser Arg His Leu Asn
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Synthetic

<400> SEQUENCE: 125

Arg Ala Ser Gln Thr Val Arg Ser Tyr Leu Asn
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Synthetic

<400> SEQUENCE: 126

Ala Ala Ser Ser Leu Gln Ser
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic

<400> SEQUENCE: 127

Ala Ala Ser Thr Leu Gln Ser
1               5

<210> SEQ ID NO 128
<211> LENGTH: 7
<212> TYPE: PRT
<213> ORGANISM: Artificial Sequence
<220> FEATURE:
<223> OTHER INFORMATION: Synthetic

<400> SEQUENCE: 128

Ala Ala Ser Ser Leu His Pro
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic

<400> SEQUENCE: 129

Ala Ala Ser Asn Leu Glu Ser
1               5

<210> SEQ ID NO 130
```

```
<211> LENGTH: 7
<212> TYPE: PRT
<213> ORGANISM: Artificial Sequence
<220> FEATURE:
<223> OTHER INFORMATION: Synthetic

<400> SEQUENCE: 130

Ala Ala Phe Asn Leu Gln Gly
1               5

<210> SEQ ID NO 131
<211> LENGTH: 7
<212> TYPE: PRT
<213> ORGANISM: Artificial Sequence
<220> FEATURE:
<223> OTHER INFORMATION: Synthetic

<400> SEQUENCE: 131

Gly Ala Ser Thr Leu Glu Ser
1               5

<210> SEQ ID NO 132
<211> LENGTH: 7
<212> TYPE: PRT
<213> ORGANISM: Artificial Sequence
<220> FEATURE:
<223> OTHER INFORMATION: Synthetic

<400> SEQUENCE: 132

Trp Ala Ser Thr Arg Glu Ser
1               5

<210> SEQ ID NO 133
<211> LENGTH: 7
<212> TYPE: PRT
<213> ORGANISM: Artificial Sequence
<220> FEATURE:
<223> OTHER INFORMATION: Synthetic

<400> SEQUENCE: 133

Ala Thr Ser Thr Leu Gln Ser
1               5

<210> SEQ ID NO 134
<211> LENGTH: 7
<212> TYPE: PRT
<213> ORGANISM: Artificial Sequence
<220> FEATURE:
<223> OTHER INFORMATION: Synthetic

<400> SEQUENCE: 134

Gly Ala Ser Thr Arg Ala Thr
1               5

<210> SEQ ID NO 135
<211> LENGTH: 7
<212> TYPE: PRT
<213> ORGANISM: Artificial Sequence
<220> FEATURE:
<223> OTHER INFORMATION: Synthetic

<400> SEQUENCE: 135

Ala Ala Ser Ile Leu Gln Ser
1               5

<210> SEQ ID NO 136
<211> LENGTH: 7
```

```
<212> TYPE: PRT
<213> ORGANISM: Artificial Sequence
<220> FEATURE:
<223> OTHER INFORMATION: Synthetic

<400> SEQUENCE: 136

Ser Ala Ser Asn Leu Gln Ser
1               5

<210> SEQ ID NO 137
<211> LENGTH: 7
<212> TYPE: PRT
<213> ORGANISM: Artificial Sequence
<220> FEATURE:
<223> OTHER INFORMATION: Synthetic

<400> SEQUENCE: 137

Leu Gly Ser Asn Arg Ala Ser
1               5

<210> SEQ ID NO 138
<211> LENGTH: 7
<212> TYPE: PRT
<213> ORGANISM: Artificial Sequence
<220> FEATURE:
<223> OTHER INFORMATION: Synthetic

<400> SEQUENCE: 138

Ala Ala Ser Arg Leu Gln Ser
1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic

<400> SEQUENCE: 139

Gly Ala Ser Ser Leu Gln Ser
1               5

<210> SEQ ID NO 140
<211> LENGTH: 7
<212> TYPE: PRT
<213> ORGANISM: Artificial Sequence
<220> FEATURE:
<223> OTHER INFORMATION: Synthetic

<400> SEQUENCE: 140

Leu Ala Ser Ser Leu Gln Ser
1               5

<210> SEQ ID NO 141
<211> LENGTH: 7
<212> TYPE: PRT
<213> ORGANISM: Artificial Sequence
<220> FEATURE:
<223> OTHER INFORMATION: Synthetic

<400> SEQUENCE: 141

Lys Ala Ser Ser Leu Glu Ser
1               5

<210> SEQ ID NO 142
<211> LENGTH: 7
<212> TYPE: PRT
```

```
<213> ORGANISM: Artificial Sequence
<220> FEATURE:
<223> OTHER INFORMATION: Synthetic

<400> SEQUENCE: 142

Ala Ala Ser Ser Leu Gln Thr
1               5

<210> SEQ ID NO 143
<211> LENGTH: 7
<212> TYPE: PRT
<213> ORGANISM: Artificial Sequence
<220> FEATURE:
<223> OTHER INFORMATION: Synthetic

<400> SEQUENCE: 143

Ala Ala Ser Asn Leu Gln Lys
1               5

<210> SEQ ID NO 144
<211> LENGTH: 7
<212> TYPE: PRT
<213> ORGANISM: Artificial Sequence
<220> FEATURE:
<223> OTHER INFORMATION: Synthetic

<400> SEQUENCE: 144

Asp Thr Ser Asn Leu Glu Thr
1               5

<210> SEQ ID NO 145
<211> LENGTH: 7
<212> TYPE: PRT
<213> ORGANISM: Artificial Sequence
<220> FEATURE:
<223> OTHER INFORMATION: Synthetic

<400> SEQUENCE: 145

Trp Ala Ser Phe Arg Glu Ser
1               5

<210> SEQ ID NO 146
<211> LENGTH: 7
<212> TYPE: PRT
<213> ORGANISM: Artificial Sequence
<220> FEATURE:
<223> OTHER INFORMATION: Synthetic

<400> SEQUENCE: 146

Trp Ala Ser Ala Arg Glu Ser
1               5

<210> SEQ ID NO 147
<211> LENGTH: 7
<212> TYPE: PRT
<213> ORGANISM: Artificial Sequence
<220> FEATURE:
<223> OTHER INFORMATION: Synthetic

<400> SEQUENCE: 147

Trp Ala Ser Ile Arg Glu Ser
1               5

<210> SEQ ID NO 148
<211> LENGTH: 7
<212> TYPE: PRT
<213> ORGANISM: Artificial Sequence
```

```
<220> FEATURE:
<223> OTHER INFORMATION: Synthetic

<400> SEQUENCE: 148

Asp Ala Ser Asn Leu His Ala
1               5

<210> SEQ ID NO 149
<211> LENGTH: 9
<212> TYPE: PRT
<213> ORGANISM: Artificial Sequence
<220> FEATURE:
<223> OTHER INFORMATION: Synthetic

<400> SEQUENCE: 149

Gln Gln Thr Asp Ser Ile Pro Ile Thr
1               5

<210> SEQ ID NO 150
<211> LENGTH: 9
<212> TYPE: PRT
<213> ORGANISM: Artificial Sequence
<220> FEATURE:
<223> OTHER INFORMATION: Synthetic

<400> SEQUENCE: 150

Gln Gln Ser Tyr Ser Thr Pro Leu Thr
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic

<400> SEQUENCE: 151

Gln Gln Thr Asn Ser Phe Pro Leu Thr
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic

<400> SEQUENCE: 152

Glu Gln Asn Tyr Arg Leu Pro Ile Thr
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic

<400> SEQUENCE: 153

Gln Gln Ser Asp Ser Phe Pro Leu Thr
1               5

<210> SEQ ID NO 154
<211> LENGTH: 9
<212> TYPE: PRT
<213> ORGANISM: Artificial Sequence
<220> FEATURE:
```

<223> OTHER INFORMATION: Synthetic

<400> SEQUENCE: 154

Gln Gln Thr Asn Ser Phe Pro Ile Thr
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic

<400> SEQUENCE: 155

Gln Gln Ser Tyr Ser Phe Pro Leu Thr
1               5

<210> SEQ ID NO 156
<211> LENGTH: 9
<212> TYPE: PRT
<213> ORGANISM: Artificial Sequence
<220> FEATURE:
<223> OTHER INFORMATION: Synthetic

<400> SEQUENCE: 156

Gln Gln Ala His Ser Phe Pro Leu Thr
1               5

<210> SEQ ID NO 157
<211> LENGTH: 9
<212> TYPE: PRT
<213> ORGANISM: Artificial Sequence
<220> FEATURE:
<223> OTHER INFORMATION: Synthetic

<400> SEQUENCE: 157

Gln Gln Ser Tyr Ser Thr Pro Ile Thr
1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic

<400> SEQUENCE: 158

Gln Gln Tyr Tyr Ser Thr Pro Leu Thr
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic

<400> SEQUENCE: 159

Gln Gln Ala Asn Ser Leu Pro Tyr Ser
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Gly Tyr Ser Thr Pro Tyr Thr
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic

<400> SEQUENCE: 161

Gln Gln Tyr Gly Thr Ser Pro Phe Thr
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic

<400> SEQUENCE: 162

Gln Gln Ser Tyr Thr Thr Thr Leu Thr
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic

<400> SEQUENCE: 163

Gln Gln Ala Asn Ser Phe Pro Leu Thr
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic

<400> SEQUENCE: 164

Met Gln Gly Ala His Trp Pro Tyr Thr
1               5

<210> SEQ ID NO 165
<211> LENGTH: 9
<212> TYPE: PRT
<213> ORGANISM: Artificial Sequence
<220> FEATURE:
<223> OTHER INFORMATION: Synthetic

<400> SEQUENCE: 165

Met Gln Ala Leu Gln Thr Pro Leu Thr
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic

```
<400> SEQUENCE: 166

Gln Gln Ser Tyr Gly Ile Pro Leu Thr
1               5

<210> SEQ ID NO 167
<211> LENGTH: 9
<212> TYPE: PRT
<213> ORGANISM: Artificial Sequence
<220> FEATURE:
<223> OTHER INFORMATION: Synthetic

<400> SEQUENCE: 167

Gln Gln Ala Asn Thr Phe Pro Leu Thr
1               5

<210> SEQ ID NO 168
<211> LENGTH: 9
<212> TYPE: PRT
<213> ORGANISM: Artificial Sequence
<220> FEATURE:
<223> OTHER INFORMATION: Synthetic

<400> SEQUENCE: 168

Gln Gln Thr Tyr Ser Phe Pro Leu Thr
1               5

<210> SEQ ID NO 169
<211> LENGTH: 8
<212> TYPE: PRT
<213> ORGANISM: Artificial Sequence
<220> FEATURE:
<223> OTHER INFORMATION: Synthetic

<400> SEQUENCE: 169

Gln Gln Ser Tyr Ser Thr Pro Pro
1               5

<210> SEQ ID NO 170
<211> LENGTH: 9
<212> TYPE: PRT
<213> ORGANISM: Artificial Sequence
<220> FEATURE:
<223> OTHER INFORMATION: Synthetic

<400> SEQUENCE: 170

Gln Gln Ala Asn Ser Phe Pro Arg Thr
1               5

<210> SEQ ID NO 171
<211> LENGTH: 9
<212> TYPE: PRT
<213> ORGANISM: Artificial Sequence
<220> FEATURE:
<223> OTHER INFORMATION: Synthetic

<400> SEQUENCE: 171

Leu Gln His Asn Ser Phe Pro Pro Thr
1               5

<210> SEQ ID NO 172
<211> LENGTH: 9
<212> TYPE: PRT
<213> ORGANISM: Artificial Sequence
<220> FEATURE:
<223> OTHER INFORMATION: Synthetic
```

<400> SEQUENCE: 172

Leu Gln Ala Ile Ser Phe Pro Phe Thr
1               5

<210> SEQ ID NO 173
<211> LENGTH: 9
<212> TYPE: PRT
<213> ORGANISM: Artificial Sequence
<220> FEATURE:
<223> OTHER INFORMATION: Synthetic

<400> SEQUENCE: 173

Gln Gln Ala Tyr Ser Leu Pro Trp Thr
1               5

<210> SEQ ID NO 174
<211> LENGTH: 9
<212> TYPE: PRT
<213> ORGANISM: Artificial Sequence
<220> FEATURE:
<223> OTHER INFORMATION: Synthetic

<400> SEQUENCE: 174

Gln Gln Ser Tyr Thr Thr Pro Tyr Thr
1               5

<210> SEQ ID NO 175
<211> LENGTH: 9
<212> TYPE: PRT
<213> ORGANISM: Artificial Sequence
<220> FEATURE:
<223> OTHER INFORMATION: Synthetic

<400> SEQUENCE: 175

Gln Gln Tyr Tyr Thr Thr Pro Leu Thr
1               5

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln Gln Tyr Lys Ser Ala Pro Tyr Thr
1               5

<210> SEQ ID NO 177
<211> LENGTH: 9
<212> TYPE: PRT
<213> ORGANISM: Artificial Sequence
<220> FEATURE:
<223> OTHER INFORMATION: Synthetic

<400> SEQUENCE: 177

Gln Gln Ser Asn Ser Phe Pro Leu Thr
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic

<400> SEQUENCE: 178

Gln Gln Ser Tyr Gln Thr Pro Leu Thr
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic

<400> SEQUENCE: 179

Gln Gln Tyr Tyr Ser Ser Pro Phe Thr
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic

<400> SEQUENCE: 180

Met Gln Ala Leu Gln Ala Pro Val Thr
1               5

<210> SEQ ID NO 181
<211> LENGTH: 9
<212> TYPE: PRT
<213> ORGANISM: Artificial Sequence
<220> FEATURE:
<223> OTHER INFORMATION: Synthetic

<400> SEQUENCE: 181

Gln Gln Thr Tyr Arg Thr Pro Leu Thr
1               5

<210> SEQ ID NO 182
<211> LENGTH: 30
<212> TYPE: PRT
<213> ORGANISM: Artificial Sequence
<220> FEATURE:
<223> OTHER INFORMATION: synthetic

<400> SEQUENCE: 182

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 183
<211> LENGTH: 30
<212> TYPE: PRT
<213> ORGANISM: Artificial Sequence
<220> FEATURE:
<223> OTHER INFORMATION: Synthetic

<400> SEQUENCE: 183

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr
            20                  25                  30

<210> SEQ ID NO 184
<211> LENGTH: 30

```
<212> TYPE: PRT
<213> ORGANISM: Artificial Sequence
<220> FEATURE:
<223> OTHER INFORMATION: Synthetic

<400> SEQUENCE: 184

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Leu Asn
            20                  25                  30

<210> SEQ ID NO 185
<211> LENGTH: 30
<212> TYPE: PRT
<213> ORGANISM: Artificial Sequence
<220> FEATURE:
<223> OTHER INFORMATION: Synthetic

<400> SEQUENCE: 185

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 186
<211> LENGTH: 30
<212> TYPE: PRT
<213> ORGANISM: Artificial Sequence
<220> FEATURE:
<223> OTHER INFORMATION: Synthetic

<400> SEQUENCE: 186

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr
            20                  25                  30

<210> SEQ ID NO 187
<211> LENGTH: 30
<212> TYPE: PRT
<213> ORGANISM: Artificial Sequence
<220> FEATURE:
<223> OTHER INFORMATION: Synthetic

<400> SEQUENCE: 187

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser
            20                  25                  30

<210> SEQ ID NO 188
<211> LENGTH: 30
<212> TYPE: PRT
<213> ORGANISM: Artificial Sequence
<220> FEATURE:
<223> OTHER INFORMATION: Synthetic

<400> SEQUENCE: 188

Gln Val Gln Leu Val Gln Ser Gly Val Arg Trp Arg Ser Leu Gly Pro
1               5                   10                  15

Pro Val Lys Val Ser Cys Lys Ala Ser Gly Asp Thr Phe Ser
            20                  25                  30

<210> SEQ ID NO 189
```

```
<211> LENGTH: 30
<212> TYPE: PRT
<213> ORGANISM: Artificial Sequence
<220> FEATURE:
<223> OTHER INFORMATION: Synthetic

<400> SEQUENCE: 189

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr
            20                  25                  30

<210> SEQ ID NO 190
<211> LENGTH: 30
<212> TYPE: PRT
<213> ORGANISM: Artificial Sequence
<220> FEATURE:
<223> OTHER INFORMATION: Synthetic

<400> SEQUENCE: 190

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser
            20                  25                  30

<210> SEQ ID NO 191
<211> LENGTH: 30
<212> TYPE: PRT
<213> ORGANISM: Artificial Sequence
<220> FEATURE:
<223> OTHER INFORMATION: Synthetic

<400> SEQUENCE: 191

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 192
<211> LENGTH: 30
<212> TYPE: PRT
<213> ORGANISM: Artificial Sequence
<220> FEATURE:
<223> OTHER INFORMATION: Synthetic

<400> SEQUENCE: 192

Gln Val Gln Leu Val Gln Ser Gly Ala Glu Val Lys Lys Pro Gly Ala
1               5                   10                  15

Ser Val Lys Val Ser Cys Lys Ala Ser Glu Tyr Thr Phe Thr
            20                  25                  30

<210> SEQ ID NO 193
<211> LENGTH: 30
<212> TYPE: PRT
<213> ORGANISM: Artificial Sequence
<220> FEATURE:
<223> OTHER INFORMATION: Synthetic

<400> SEQUENCE: 193

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr
            20                  25                  30
```

```
<210> SEQ ID NO 194
<211> LENGTH: 30
<212> TYPE: PRT
<213> ORGANISM: Artificial Sequence
<220> FEATURE:
<223> OTHER INFORMATION: Synthetic

<400> SEQUENCE: 194

Glu Val Gln Leu Leu Glu Ser Gly Gly Gly Leu Val Gln Pro Gly Gly
1               5                   10                  15

Ser Leu Arg Leu Ser Cys Ala Ala Ser Thr Phe Pro Phe Ser
            20                  25                  30

<210> SEQ ID NO 195
<211> LENGTH: 30
<212> TYPE: PRT
<213> ORGANISM: Artificial Sequence
<220> FEATURE:
<223> OTHER INFORMATION: Synthetic

<400> SEQUENCE: 195

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr
            20                  25                  30

<210> SEQ ID NO 196
<211> LENGTH: 30
<212> TYPE: PRT
<213> ORGANISM: Artificial Sequence
<220> FEATURE:
<223> OTHER INFORMATION: Synthetic

<400> SEQUENCE: 196

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Gly Ser
            20                  25                  30

<210> SEQ ID NO 197
<211> LENGTH: 30
<212> TYPE: PRT
<213> ORGANISM: Artificial Sequence
<220> FEATURE:
<223> OTHER INFORMATION: Synthetic

<400> SEQUENCE: 197

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Ser
            20                  25                  30

<210> SEQ ID NO 198
<211> LENGTH: 30
<212> TYPE: PRT
<213> ORGANISM: Artificial Sequence
<220> FEATURE:
<223> OTHER INFORMATION: Synthetic

<400> SEQUENCE: 198

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ser
            20                  25                  30
```

<210> SEQ ID NO 199
<211> LENGTH: 30
<212> TYPE: PRT
<213> ORGANISM: Artificial Sequence
<220> FEATURE:
<223> OTHER INFORMATION: Synthetic

<400> SEQUENCE: 199

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser
            20                  25                  30

<210> SEQ ID NO 200
<211> LENGTH: 30
<212> TYPE: PRT
<213> ORGANISM: Artificial Sequence
<220> FEATURE:
<223> OTHER INFORMATION: Synthetic

<400> SEQUENCE: 200

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser
            20                  25                  30

<210> SEQ ID NO 201
<211> LENGTH: 14
<212> TYPE: PRT
<213> ORGANISM: Artificial Sequence
<220> FEATURE:
<223> OTHER INFORMATION: Synthetic

<400> SEQUENCE: 201

Trp Val Arg Gln Ala Pro Gly Gln Gly Leu Glu Trp Met Gly
1               5                   10

<210> SEQ ID NO 202
<211> LENGTH: 14
<212> TYPE: PRT
<213> ORGANISM: Artificial Sequence
<220> FEATURE:
<223> OTHER INFORMATION: Synthetic

<400> SEQUENCE: 202

Trp Val Arg Gln Ala Pro Gly Gln Gly Leu Glu Trp Leu Gly
1               5                   10

<210> SEQ ID NO 203
<211> LENGTH: 14
<212> TYPE: PRT
<213> ORGANISM: Artificial Sequence
<220> FEATURE:
<223> OTHER INFORMATION: Synthetic

<400> SEQUENCE: 203

Trp Val Arg Gln Ala Pro Gly Lys Gly Leu Glu Trp Val Ser
1               5                   10

<210> SEQ ID NO 204
<211> LENGTH: 14
<212> TYPE: PRT
<213> ORGANISM: Artificial Sequence
<220> FEATURE:
<223> OTHER INFORMATION: Synthetic

```
<400> SEQUENCE: 204

Trp Val Arg Gln Ala Pro Gly Lys Gly Leu Glu Trp Val Ala
1               5                   10

<210> SEQ ID NO 205
<211> LENGTH: 14
<212> TYPE: PRT
<213> ORGANISM: Artificial Sequence
<220> FEATURE:
<223> OTHER INFORMATION: Synthetic

<400> SEQUENCE: 205

Trp Val Arg Gln Ala Pro Gly Lys Gly Leu Glu Trp Leu Ser
1               5                   10

<210> SEQ ID NO 206
<211> LENGTH: 14
<212> TYPE: PRT
<213> ORGANISM: Artificial Sequence
<220> FEATURE:
<223> OTHER INFORMATION: Synthetic

<400> SEQUENCE: 206

Trp Val Arg Gln Ala Pro Gly Lys Gly Leu Glu Trp Met Gly
1               5                   10

<210> SEQ ID NO 207
<211> LENGTH: 14
<212> TYPE: PRT
<213> ORGANISM: Artificial Sequence
<220> FEATURE:
<223> OTHER INFORMATION: Synthetic

<400> SEQUENCE: 207

Trp Val Arg Gln Ala Pro Gly Gln Gly Leu Glu Trp Met Ala
1               5                   10

<210> SEQ ID NO 208
<211> LENGTH: 32
<212> TYPE: PRT
<213> ORGANISM: Artificial Sequence
<220> FEATURE:
<223> OTHER INFORMATION: Synthetic

<400> SEQUENCE: 208

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 209
<211> LENGTH: 32
<212> TYPE: PRT
<213> ORGANISM: Artificial Sequence
<220> FEATURE:
<223> OTHER INFORMATION: Synthetic

<400> SEQUENCE: 209

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 210
<211> LENGTH: 32
```

```
<212> TYPE: PRT
<213> ORGANISM: Artificial Sequence
<220> FEATURE:
<223> OTHER INFORMATION: Synthetic

<400> SEQUENCE: 210

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Thr Arg
            20                  25                  30

<210> SEQ ID NO 211
<211> LENGTH: 32
<212> TYPE: PRT
<213> ORGANISM: Artificial Sequence
<220> FEATURE:
<223> OTHER INFORMATION: Synthetic

<400> SEQUENCE: 211

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 212
<211> LENGTH: 32
<212> TYPE: PRT
<213> ORGANISM: Artificial Sequence
<220> FEATURE:
<223> OTHER INFORMATION: Synthetic

<400> SEQUENCE: 212

Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Tyr Cys Ala Arg
            20                  25                  30

<210> SEQ ID NO 213
<211> LENGTH: 32
<212> TYPE: PRT
<213> ORGANISM: Artificial Sequence
<220> FEATURE:
<223> OTHER INFORMATION: Synthetic

<400> SEQUENCE: 213

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Gly
            20                  25                  30

<210> SEQ ID NO 214
<211> LENGTH: 32
<212> TYPE: PRT
<213> ORGANISM: Artificial Sequence
<220> FEATURE:
<223> OTHER INFORMATION: Synthetic

<400> SEQUENCE: 214

Arg Phe Thr Ile Ser Arg Asp Asn Ser Lys Asn Thr Leu Tyr Leu Gln
1               5                   10                  15

Asn Glu Gln Pro Gly Ala Glu Asp Thr Ala Val Tyr Tyr Cys Ala Arg
            20                  25                  30

<210> SEQ ID NO 215
```

```
<211> LENGTH: 32
<212> TYPE: PRT
<213> ORGANISM: Artificial Sequence
<220> FEATURE:
<223> OTHER INFORMATION: Synthetic

<400> SEQUENCE: 215

Arg Val Thr Ile Thr Ala Asp Glu Ser Thr Ser Ala Tyr Met Glu
1               5                   10                  15

Leu Ser Ser Leu Arg Ser Glu Asp Thr Ala Val Tyr Tyr Cys Thr Arg
            20                  25                  30

<210> SEQ ID NO 216
<211> LENGTH: 11
<212> TYPE: PRT
<213> ORGANISM: Artificial Sequence
<220> FEATURE:
<223> OTHER INFORMATION: Synthetic

<400> SEQUENCE: 216

Trp Gly Gln Gly Thr Thr Val Thr Val Ser Ser
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Synthetic

<400> SEQUENCE: 217

Trp Gly Arg Gly Thr Leu Val Thr Val Ser Ser
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Synthetic

<400> SEQUENCE: 218

Trp Gly Lys Gly Thr Thr Val Thr Val Ser Ser
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Synthetic

<400> SEQUENCE: 219

Trp Gly Gln Gly Thr Met Val Thr Val Ser Ser
1               5                   10

<210> SEQ ID NO 220
<211> LENGTH: 11
<212> TYPE: PRT
<213> ORGANISM: Artificial Sequence
<220> FEATURE:
<223> OTHER INFORMATION: Synthetic

<400> SEQUENCE: 220

Trp Gly Gln Gly Thr Leu Val Thr Val Ser Ser
1               5                   10
```

```
<210> SEQ ID NO 221
<211> LENGTH: 11
<212> TYPE: PRT
<213> ORGANISM: Artificial Sequence
<220> FEATURE:
<223> OTHER INFORMATION: Synthetic

<400> SEQUENCE: 221

Trp Gly Lys Gly Thr Leu Val Thr Val Ser Ser
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Synthetic

<400> SEQUENCE: 222

Leu Gly Pro Gly Asn Pro Val Thr Val Ser Ser
1               5                   10

<210> SEQ ID NO 223
<211> LENGTH: 23
<212> TYPE: PRT
<213> ORGANISM: Artificial Sequence
<220> FEATURE:
<223> OTHER INFORMATION: Synthetic

<400> SEQUENCE: 223

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 224
<211> LENGTH: 23
<212> TYPE: PRT
<213> ORGANISM: Artificial Sequence
<220> FEATURE:
<223> OTHER INFORMATION: Synthetic

<400> SEQUENCE: 224

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 225
<211> LENGTH: 23
<212> TYPE: PRT
<213> ORGANISM: Artificial Sequence
<220> FEATURE:
<223> OTHER INFORMATION: Synthetic

<400> SEQUENCE: 225

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 226
<211> LENGTH: 23
<212> TYPE: PRT
<213> ORGANISM: Artificial Sequence
```

```
<220> FEATURE:
<223> OTHER INFORMATION: Synthetic

<400> SEQUENCE: 226

Asp Ile Val Met Thr Gln Ser Pro Leu Phe Leu Pro Val Thr Pro Gly
1               5                   10                  15

Glu Pro Ala Ser Ile Ser Cys
            20

<210> SEQ ID NO 227
<211> LENGTH: 23
<212> TYPE: PRT
<213> ORGANISM: Artificial Sequence
<220> FEATURE:
<223> OTHER INFORMATION: Synthetic

<400> SEQUENCE: 227

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 228
<211> LENGTH: 15
<212> TYPE: PRT
<213> ORGANISM: Artificial Sequence
<220> FEATURE:
<223> OTHER INFORMATION: Synthetic

<400> SEQUENCE: 228

Trp Tyr Gln Gln Lys Pro Gly Lys Ala Pro Lys Leu Leu Ile Tyr
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: Synthetic

<400> SEQUENCE: 229

Trp Tyr Gln Gln Lys Pro Gly Gln Pro Pro Lys Leu Leu Ile Tyr
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Synthetic

<400> SEQUENCE: 230

Trp Tyr Gln Gln Lys Pro Gly Gln Ala Pro Arg Leu Leu Ile Tyr
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: Synthetic

<400> SEQUENCE: 231

Trp Tyr His Gln Lys Pro Gly Lys Ala Pro Lys Leu Leu Ile Tyr
1               5                   10                  15
```

<210> SEQ ID NO 232
<211> LENGTH: 15
<212> TYPE: PRT
<213> ORGANISM: Artificial Sequence
<220> FEATURE:
<223> OTHER INFORMATION: Synthetic

<400> SEQUENCE: 232

Trp Tyr Leu Gln Lys Pro Gly Gln Ser Pro Gln Leu Leu Ile Tyr
1               5                   10                  15

<210> SEQ ID NO 233
<211> LENGTH: 32
<212> TYPE: PRT
<213> ORGANISM: Artificial Sequence
<220> FEATURE:
<223> OTHER INFORMATION: Synthetic

<400> SEQUENCE: 233

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 234
<211> LENGTH: 32
<212> TYPE: PRT
<213> ORGANISM: Artificial Sequence
<220> FEATURE:
<223> OTHER INFORMATION: Synthetic

<400> SEQUENCE: 234

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
                20                  25                  30

<210> SEQ ID NO 235
<211> LENGTH: 32
<212> TYPE: PRT
<213> ORGANISM: Artificial Sequence
<220> FEATURE:
<223> OTHER INFORMATION: Synthetic

<400> SEQUENCE: 235

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
                20                  25                  30

<210> SEQ ID NO 236
<211> LENGTH: 32
<212> TYPE: PRT
<213> ORGANISM: Artificial Sequence
<220> FEATURE:
<223> OTHER INFORMATION: Synthetic

<400> SEQUENCE: 236

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
                20                  25                  30

<210> SEQ ID NO 237

```
<211> LENGTH: 10
<212> TYPE: PRT
<213> ORGANISM: Artificial Sequence
<220> FEATURE:
<223> OTHER INFORMATION: Synthetic

<400> SEQUENCE: 237

Phe Gly Gln Gly Thr Lys Val Glu Ile Lys
1               5                   10

<210> SEQ ID NO 238
<211> LENGTH: 10
<212> TYPE: PRT
<213> ORGANISM: Artificial Sequence
<220> FEATURE:
<223> OTHER INFORMATION: Synthetic

<400> SEQUENCE: 238

Phe Gly Pro Gly Thr Lys Val Asp Ile Lys
1               5                   10

<210> SEQ ID NO 239
<211> LENGTH: 10
<212> TYPE: PRT
<213> ORGANISM: Artificial Sequence
<220> FEATURE:
<223> OTHER INFORMATION: Synthetic

<400> SEQUENCE: 239

Phe Gly Gly Gly Thr Lys Val Glu Ile Lys
1               5                   10

<210> SEQ ID NO 240
<211> LENGTH: 10
<212> TYPE: PRT
<213> ORGANISM: Artificial Sequence
<220> FEATURE:
<223> OTHER INFORMATION: Synthetic

<400> SEQUENCE: 240

Phe Gly Gln Gly Thr Arg Leu Glu Ile Lys
1               5                   10

<210> SEQ ID NO 241
<211> LENGTH: 10
<212> TYPE: PRT
<213> ORGANISM: Artificial Sequence
<220> FEATURE:
<223> OTHER INFORMATION: Synthetic

<400> SEQUENCE: 241

Phe Gly Gln Gly Thr Lys Leu Glu Ile Lys
1               5                   10

<210> SEQ ID NO 242
<211> LENGTH: 10
<212> TYPE: PRT
<213> ORGANISM: Artificial Sequence
<220> FEATURE:
<223> OTHER INFORMATION: Synthetic

<400> SEQUENCE: 242

Phe Gly Gly Gly Thr Lys Leu Glu Ile Lys
1               5                   10

<210> SEQ ID NO 243
<211> LENGTH: 128
```

```
<212> TYPE: PRT
<213> ORGANISM: Artificial Sequence
<220> FEATURE:
<223> OTHER INFORMATION: Synthetic

<400> SEQUENCE: 243

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Gln Trp Val Arg Gln Ala Pro Gly Gln Gly Leu Glu Trp Met
        35                  40                  45

Gly Trp Ile Asn Pro Lys Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Thr Tyr Leu Arg Thr Gly Ser Ser Leu Ser Gly Tyr Tyr
            100                 105                 110

Tyr Gly Met Asp Val Trp Gly Gln Gly Thr Thr Val Thr Val Ser Ser
        115                 120                 125

<210> SEQ ID NO 244
<211> LENGTH: 121
<212> TYPE: PRT
<213> ORGANISM: Artificial Sequence
<220> FEATURE:
<223> OTHER INFORMATION: Synthetic

<400> SEQUENCE: 244

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Thr Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser His Tyr Gly Asp Leu Asn Gly Gly Phe Asp Leu Trp Gly
            100                 105                 110

Arg Gly Thr Leu Val Thr Val Ser Ser
        115                 120

<210> SEQ ID NO 245
<211> LENGTH: 121
<212> TYPE: PRT
<213> ORGANISM: Artificial Sequence
<220> FEATURE:
<223> OTHER INFORMATION: Synthetic

<400> SEQUENCE: 245

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Gly Thr Leu Asn Asn Phe
            20                  25                  30

Gly Ile Asn Trp Val Arg Gln Ala Pro Gly Gln Gly Leu Glu Trp Met
        35                  40                  45

Gly Trp Ile Asn Pro Asn Ser Gly Gly Ala Asn Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Val Val Ala Ala Arg Tyr Tyr Tyr Met Asp Val Trp Gly
             100                 105                 110

Lys Gly Thr Thr Val Thr Val Ser Ser
            115                 120

<210> SEQ ID NO 246
<211> LENGTH: 126
<212> TYPE: PRT
<213> ORGANISM: Artificial Sequence
<220> FEATURE:
<223> OTHER INFORMATION: Synthetic

<400> SEQUENCE: 246

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Leu
        35                  40                  45

Gly Trp Ile Asn Pro Asn Ser Gly Ala Thr Asn Ser Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ala Gly Tyr Ser Ser Ser Trp Asp Gly Tyr Tyr Tyr Tyr Gly
             100                 105                 110

Met Asp Val Trp Gly Gln Gly Thr Thr Val Thr Val Ser Ser
            115                 120                 125

<210> SEQ ID NO 247
<211> LENGTH: 121
<212> TYPE: PRT
<213> ORGANISM: Artificial Sequence
<220> FEATURE:
<223> OTHER INFORMATION: Synthetic

<400> SEQUENCE: 247

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Val His Trp Val Arg Gln Ala Pro Gly Gln Gly Leu Glu Trp Met
        35                  40                  45

Gly Ile Ile His Pro Asn Gly Gly Ser Thr Ser Tyr Ala Gln Lys Phe
 50                  55                  60
```

```
Gln Gly Arg Val Thr Met Thr Arg Asp Thr Ser Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Gln Ala Gly Thr Gly Gly His Gly Met Asp Val Trp Gly
            100                 105                 110

Gln Gly Thr Met Val Thr Val Ser Ser
        115                 120
```

<210> SEQ ID NO 248
<211> LENGTH: 128
<212> TYPE: PRT
<213> ORGANISM: Artificial Sequence
<220> FEATURE:
<223> OTHER INFORMATION: Synthetic

<400> SEQUENCE: 248

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Asp Ile Ser Gly Ser Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Tyr Leu Glu Trp Val Leu Ser Ser Glu Asp Tyr Tyr
            100                 105                 110

Phe Gly Met Asp Val Trp Gly Gln Gly Thr Thr Val Thr Val Ser Ser
        115                 120                 125
```

<210> SEQ ID NO 249
<211> LENGTH: 123
<212> TYPE: PRT
<213> ORGANISM: Artificial Sequence
<220> FEATURE:
<223> OTHER INFORMATION: Synthetic

<400> SEQUENCE: 249

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Gly Arg Tyr Ser Arg Ser Trp Glu Arg Trp Tyr Phe Asp Leu
            100                 105                 110

Trp Gly Arg Gly Thr Leu Val Thr Val Ser Ser
        115                 120

<210> SEQ ID NO 250
<211> LENGTH: 122
<212> TYPE: PRT
<213> ORGANISM: Artificial Sequence
<220> FEATURE:
<223> OTHER INFORMATION: Synthetic

<400> SEQUENCE: 250

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Gln
            20                  25                  30

Tyr Met His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gln Tyr Asp Ser Ser Gly Tyr Tyr Tyr Phe Asp Tyr Trp
            100                 105                 110

Gly Gln Gly Thr Leu Val Thr Val Ser Ser
        115                 120

<210> SEQ ID NO 251
<211> LENGTH: 122
<212> TYPE: PRT
<213> ORGANISM: Artificial Sequence
<220> FEATURE:
<223> OTHER INFORMATION: Synthetic

<400> SEQUENCE: 251

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Met Asn Trp Val Arg Gln Ala Pro Gly Gln Gly Leu Glu Trp Met
        35                  40                  45

Gly Ile Leu Ser Pro Ser Gly Gly Thr Ser Tyr Ala Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Thr Tyr Tyr Asp Phe Trp Ser Gly Ser Leu Asp Tyr Trp
            100                 105                 110

Gly Gln Gly Thr Leu Val Thr Val Ser Ser
        115                 120

<210> SEQ ID NO 252
<211> LENGTH: 119
<212> TYPE: PRT

```
<213> ORGANISM: Artificial Sequence
<220> FEATURE:
<223> OTHER INFORMATION: Synthetic

<400> SEQUENCE: 252

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Phe Met His Trp Val Arg Gln Ala Pro Gly Gln Gly Leu Glu Trp Met
            35                  40                  45

Gly Trp Met Asn Pro Asn Asn Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gln Ala Gly Tyr Ser Ser Gly Trp Asp Tyr Trp Gly Gln Gly
                100                 105                 110

Thr Leu Val Thr Val Ser Ser
        115

<210> SEQ ID NO 253
<211> LENGTH: 123
<212> TYPE: PRT
<213> ORGANISM: Artificial Sequence
<220> FEATURE:
<223> OTHER INFORMATION: Synthetic

<400> SEQUENCE: 253

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Thr Trp
                20                  25                  30

Tyr Met Gln Trp Val Arg Gln Ala Pro Gly Gln Gly Leu Glu Trp Met
            35                  40                  45

Gly Trp Ile Ser Pro Tyr Thr Gly Asn Thr Ile Tyr Ala Pro Asn Val
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Ala Val Tyr Asp Ile Leu Thr Gly Ala Tyr Tyr Phe Asp Tyr
                100                 105                 110

Trp Gly Gln Gly Thr Leu Val Thr Val Ser Ser
        115                 120

<210> SEQ ID NO 254
<211> LENGTH: 121
<212> TYPE: PRT
<213> ORGANISM: Artificial Sequence
<220> FEATURE:
<223> OTHER INFORMATION: Synthetic

<400> SEQUENCE: 254

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
                20                  25                  30
```

Ala Ile Ser Trp Val Arg Gln Ala Pro Gly Gln Gly Leu Glu Trp Met
        35                  40                  45

Gly Trp Ile Ser Thr Tyr Asn Gly Asn Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Arg Leu Pro Pro Tyr Tyr Tyr Gly Met Asp Val Trp Gly
            100                 105                 110

Gln Gly Thr Thr Val Thr Val Ser Ser
            115                 120

<210> SEQ ID NO 255
<211> LENGTH: 123
<212> TYPE: PRT
<213> ORGANISM: Artificial Sequence
<220> FEATURE:
<223> OTHER INFORMATION: Synthetic

<400> SEQUENCE: 255

Gln Val Gln Leu Val Gln Ser Gly Val Arg Trp Arg Ser Leu Gly Pro
1               5                   10                  15

Pro Val Lys Val Ser Cys Lys Ala Ser Gly Asp Thr Phe Ser Arg Tyr
            20                  25                  30

Tyr Leu His Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Ala Thr Val Thr Lys His Thr Tyr Trp Tyr Phe Asp Leu
            100                 105                 110

Trp Gly Arg Gly Thr Leu Val Thr Val Ser Ser
        115                 120

<210> SEQ ID NO 256
<211> LENGTH: 124
<212> TYPE: PRT
<213> ORGANISM: Artificial Sequence
<220> FEATURE:
<223> OTHER INFORMATION: Synthetic

<400> SEQUENCE: 256

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Gln
            20                  25                  30

Trp Val His Trp Val Arg Gln Ala Pro Gly Lys Gly Leu Glu Trp Val
        35                  40                  45

Ala Leu Ile Ser Tyr Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Arg Ser Thr Ser Arg Tyr Tyr Tyr Tyr Met Asp
            100                 105                 110

Val Trp Gly Lys Gly Thr Thr Val Thr Val Ser Ser
        115                 120

<210> SEQ ID NO 257
<211> LENGTH: 121
<212> TYPE: PRT
<213> ORGANISM: Artificial Sequence
<220> FEATURE:
<223> OTHER INFORMATION: Synthetic

<400> SEQUENCE: 257

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Pro Asn
            20                  25                  30

Tyr Ile Gln Trp Val Arg Gln Ala Pro Gly Gln Gly Leu Glu Trp Met
        35                  40                  45

Gly Ile Ile Asn Pro Ser Gly Arg Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Ser Ser Gly Tyr Thr Thr Asp Ala Phe Asp Ile Trp Gly
            100                 105                 110

Gln Gly Thr Thr Val Thr Val Ser Ser
        115                 120

<210> SEQ ID NO 258
<211> LENGTH: 120
<212> TYPE: PRT
<213> ORGANISM: Artificial Sequence
<220> FEATURE:
<223> OTHER INFORMATION: Synthetic

<400> SEQUENCE: 258

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ala Ser
            20                  25                  30

Tyr Ile His Trp Val Arg Gln Ala Pro Gly Gln Gly Leu Glu Trp Met
        35                  40                  45

Gly Gly Ile Ile Pro Ile Phe Gly Ser Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Gln Leu Met Asn Val Gly Met Asp Val Trp Gly Gln
            100                 105                 110

Gly Thr Thr Val Thr Val Ser Ser
        115                 120

```
<210> SEQ ID NO 259
<211> LENGTH: 118
<212> TYPE: PRT
<213> ORGANISM: Artificial Sequence
<220> FEATURE:
<223> OTHER INFORMATION: Synthetic

<400> SEQUENCE: 259
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Ile | Phe | Ser | Asp | Ser |
|---|---|---|---|---|---|---|---|---|---|---|---|---|---|---|---|
| | | | 20 | | | | | 25 | | | | | 30 | | |

| His | Leu | His | Trp | Val | Arg | Gln | Ala | Pro | Gly | Lys | Gly | Leu | Glu | Trp | Leu |
|---|---|---|---|---|---|---|---|---|---|---|---|---|---|---|---|
| | | 35 | | | | | 40 | | | | | 45 | | | |

| Ser | Val | Ile | Tyr | Ala | Gly | Gly | Ser | Arg | Tyr | Tyr | Ala | Asp | Ser | Val | Lys |
|---|---|---|---|---|---|---|---|---|---|---|---|---|---|---|---|
| | 50 | | | | | 55 | | | | | 60 | | | | |

| Gly | Arg | Phe | Thr | Ile | Ser | Arg | Asp | Asn | Ser | Lys | Asn | Thr | Leu | Tyr | Leu |
|---|---|---|---|---|---|---|---|---|---|---|---|---|---|---|---|
| 65 | | | | | 70 | | | | | 75 | | | | | 80 |

| Gln | Met | Asn | Ser | Leu | Arg | Ala | Glu | Asp | Thr | Ala | Val | Tyr | Tyr | Cys | Ala |
|---|---|---|---|---|---|---|---|---|---|---|---|---|---|---|---|
| | | | | 85 | | | | | 90 | | | | | 95 | |

| Arg | Gly | Lys | Gln | Arg | Ala | Asp | Ala | Phe | Asp | Ile | Trp | Gly | Gln | Gly | Thr |
|---|---|---|---|---|---|---|---|---|---|---|---|---|---|---|---|
| | | | 100 | | | | | 105 | | | | | 110 | | |

| Leu | Val | Thr | Val | Ser | Ser |
|---|---|---|---|---|---|
| | | 115 | | | |

```
<210> SEQ ID NO 260
<211> LENGTH: 124
<212> TYPE: PRT
<213> ORGANISM: Artificial Sequence
<220> FEATURE:
<223> OTHER INFORMATION: Synthetic

<400> SEQUENCE: 260
```

| Glu | Val | Gln | Leu | Leu | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Trp | Met | His | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Thr | Ile | Ser | Gly | Ser | Gly | Ala | Gly | Thr | Trp | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asp | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Lys | Thr | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Asp | Val | Asp | Pro | Ser | Arg | Gln | Ser | Tyr | Tyr | His | Gly | Val | Asp |
|---|---|---|---|---|---|---|---|---|---|---|---|---|---|---|---|
| | | | 100 | | | | | 105 | | | | | 110 | | |

| Val | Trp | Gly | Gln | Gly | Thr | Thr | Val | Thr | Val | Ser | Ser |
|---|---|---|---|---|---|---|---|---|---|---|---|
| | | 115 | | | | | 120 | | | | |

```
<210> SEQ ID NO 261
<211> LENGTH: 125
<212> TYPE: PRT
<213> ORGANISM: Artificial Sequence
<220> FEATURE:
<223> OTHER INFORMATION: Synthetic

<400> SEQUENCE: 261
```

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

Ser Val Lys Val Ser Cys Lys Ala Ser Gly Tyr Ile Phe Thr Asn Tyr
            20                  25                  30

Trp Ile Gln Trp Val Arg Gln Ala Pro Gly Gln Gly Leu Glu Trp Met
        35                  40                  45

Gly Trp Ile Asn Pro Asn Ser Gly Thr Arg Tyr Ala Arg Asn Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Arg Tyr Tyr Tyr Gly Ser Gly Ser Gln Tyr His Ala Phe
                100                 105                 110

Asp Ile Trp Gly Gln Gly Thr Met Val Thr Val Ser Ser
            115                 120                 125

<210> SEQ ID NO 262
<211> LENGTH: 121
<212> TYPE: PRT
<213> ORGANISM: Artificial Sequence
<220> FEATURE:
<223> OTHER INFORMATION: Synthetic

<400> SEQUENCE: 262

Gln Val Gln Leu Val Gln Ser Gly Ala Glu Val Lys Lys Pro Gly Ala
1               5                   10                  15

Ser Val Lys Val Ser Cys Lys Ala Ser Glu Tyr Thr Phe Thr Asn Tyr
            20                  25                  30

Tyr Met His Trp Val Arg Gln Ala Pro Gly Gln Gly Leu Glu Trp Met
        35                  40                  45

Gly Trp Leu Asn Pro Asn Ser Gly Thr Asn Tyr Ala Gln Lys Phe Gln
    50                  55                  60

Gly Arg Val Thr Met Thr Arg Asp Thr Ser Thr Ser Thr Val Tyr Met
65                  70                  75                  80

Glu Leu Ser Ser Leu Arg Ser Glu Asp Thr Ala Val Tyr Tyr Cys Ala
                85                  90                  95

Arg Gly Arg Tyr Asp Ser Ser Gly Tyr Tyr Tyr Phe Asp Tyr Trp Gly
                100                 105                 110

Gln Gly Thr Leu Val Thr Val Ser Ser
            115                 120

<210> SEQ ID NO 263
<211> LENGTH: 122
<212> TYPE: PRT
<213> ORGANISM: Artificial Sequence
<220> FEATURE:
<223> OTHER INFORMATION: Synthetic

<400> SEQUENCE: 263

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Gly Tyr
            20                  25                  30

Asp Met Gln Trp Val Arg Gln Ala Pro Gly Gln Gly Leu Glu Trp Met
        35                  40                  45

Gly Ile Ile Asn Pro Ser Gly Gly Thr Asn Tyr Ala Gln Lys Phe
            50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Gly Thr Val Thr Thr Pro Tyr Gln Tyr Tyr Gly Met Asp Val Trp
            100                 105                 110

Gly Gln Gly Thr Thr Val Thr Val Ser Ser
            115                 120

<210> SEQ ID NO 264
<211> LENGTH: 119
<212> TYPE: PRT
<213> ORGANISM: Artificial Sequence
<220> FEATURE:
<223> OTHER INFORMATION: Synthetic

<400> SEQUENCE: 264

Glu Val Gln Leu Leu Glu Ser Gly Gly Gly Leu Val Gln Pro Gly Gly
 1               5                  10                  15

Ser Leu Arg Leu Ser Cys Ala Ala Ser Thr Phe Pro Phe Ser Ser Tyr
            20                  25                  30

Ser Met Asn Trp Val Arg Gln Ala Pro Gly Lys Gly Leu Glu Trp Val
        35                  40                  45

Ala Val Ile Ser Tyr Asp Gly Arg Ile Lys Asp Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Arg Gly Phe Ser Phe Trp Phe Asp Pro Trp Gly Gln Gly
            100                 105                 110

Thr Leu Val Thr Val Ser Ser
        115

<210> SEQ ID NO 265
<211> LENGTH: 119
<212> TYPE: PRT
<213> ORGANISM: Artificial Sequence
<220> FEATURE:
<223> OTHER INFORMATION: Synthetic

<400> SEQUENCE: 265

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Val Ile Ser Tyr Asp Gly Arg Ile Lys Asp Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Arg Gly Phe Ser Phe Trp Phe Asp Pro Trp Gly Gln Gly
            100                 105                 110

Thr Leu Val Thr Val Ser Ser
        115

<210> SEQ ID NO 266
<211> LENGTH: 116
<212> TYPE: PRT
<213> ORGANISM: Artificial Sequence
<220> FEATURE:
<223> OTHER INFORMATION: Synthetic

<400> SEQUENCE: 266

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Gly Ile Ser Trp Asn Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Tyr Phe Asp Tyr Trp Gly Gln Gly Thr Leu Val
            100                 105                 110

Thr Val Ser Ser
        115

<210> SEQ ID NO 267
<211> LENGTH: 128
<212> TYPE: PRT
<213> ORGANISM: Artificial Sequence
<220> FEATURE:
<223> OTHER INFORMATION: Synthetic

<400> SEQUENCE: 267

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Arg Tyr Gly Ser Ser Gly Trp Ser Pro Gly Tyr Tyr Tyr
            100                 105                 110

Tyr Tyr Met Asp Val Trp Gly Lys Gly Thr Thr Val Thr Val Ser Ser
        115                 120                 125

<210> SEQ ID NO 268
<211> LENGTH: 121
<212> TYPE: PRT

<213> ORGANISM: Artificial Sequence
<220> FEATURE:
<223> OTHER INFORMATION: Synthetic

<400> SEQUENCE: 268

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Asp Ser Gly Ser Pro Lys Asp Phe Asp Tyr Trp Gly
            100                 105                 110

Gln Gly Thr Leu Val Thr Val Ser Ser
        115                 120
```

<210> SEQ ID NO 269
<211> LENGTH: 116
<212> TYPE: PRT
<213> ORGANISM: Artificial Sequence
<220> FEATURE:
<223> OTHER INFORMATION: Synthetic

<400> SEQUENCE: 269

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Gly Thr Ser Leu Asp Gly Asn Lys Asn Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Met Ala Arg Gly Ser Trp Gly Gln Gly Thr Leu Val
            100                 105                 110

Thr Val Ser Ser
        115
```

<210> SEQ ID NO 270
<211> LENGTH: 118
<212> TYPE: PRT
<213> ORGANISM: Artificial Sequence
<220> FEATURE:
<223> OTHER INFORMATION: Synthetic

<400> SEQUENCE: 270

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Trp Met Ser Trp Val Arg Gln Ala Pro Gly Lys Gly Leu Glu Trp Val
            35                  40                  45

Ser Thr Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Asn Glu Gln Pro Gly Ala Glu Asp Thr Ala Val Tyr Tyr Cys
                85                  90                  95

Ala Arg Ala Thr Asp Tyr Pro Gly Met Asp Val Trp Gly Gln Gly Thr
            100                 105                 110

Thr Val Thr Val Ser Ser
            115

<210> SEQ ID NO 271
<211> LENGTH: 127
<212> TYPE: PRT
<213> ORGANISM: Artificial Sequence
<220> FEATURE:
<223> OTHER INFORMATION: Synthetic

<400> SEQUENCE: 271

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asn Tyr
            20                  25                  30

Tyr Met His Trp Val Arg Gln Ala Pro Gly Gln Gly Leu Glu Trp Met
            35                  40                  45

Gly Trp Ile Asn Pro His Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Arg Met His Tyr Asp Ser Ser Val His Tyr Tyr Tyr Tyr
            100                 105                 110

Gly Met Asp Val Trp Gly Gln Gly Thr Leu Val Thr Val Ser Ser
            115                 120                 125

<210> SEQ ID NO 272
<211> LENGTH: 125
<212> TYPE: PRT
<213> ORGANISM: Artificial Sequence
<220> FEATURE:
<223> OTHER INFORMATION: Synthetic

<400> SEQUENCE: 272

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Gly Ser Ser Tyr
            20                  25                  30

Ala Ile Ser Trp Val Arg Gln Ala Pro Gly Gln Gly Leu Glu Trp Met
            35                  40                  45

Gly Leu Ile Asp Pro Ser Pro Gly Thr Thr Tyr Tyr Ala Gln Lys Phe
    50                  55                  60

Gln Gly Arg Val Thr Met Thr Arg Asp Thr Ser Thr Ser Thr Val Tyr
65                  70                  75                  80
```

Met Glu Leu Ser Ser Leu Arg Ser Glu Asp Thr Ala Val Tyr Tyr Cys
               85                  90                  95

Ala Arg Val Ser Ile Val Gly Ala Thr Pro Asp Tyr Tyr Gly Met
            100                 105                 110

Asp Val Trp Gly Lys Gly Thr Leu Val Thr Val Ser Ser
        115                 120                 125

<210> SEQ ID NO 273
<211> LENGTH: 118
<212> TYPE: PRT
<213> ORGANISM: Artificial Sequence
<220> FEATURE:
<223> OTHER INFORMATION: Synthetic

<400> SEQUENCE: 273

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Arg Ile Asn Pro Asn Ser Gly Gly Thr Asn Phe Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Ile Arg Gly Gly Lys Phe Asp Pro Trp Gly Gln Gly Thr
            100                 105                 110

Leu Val Thr Val Ser Ser
        115

<210> SEQ ID NO 274
<211> LENGTH: 125
<212> TYPE: PRT
<213> ORGANISM: Artificial Sequence
<220> FEATURE:
<223> OTHER INFORMATION: Synthetic

<400> SEQUENCE: 274

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Gly Ile Thr Trp Val Arg Gln Ala Pro Gly Lys Gly Leu Glu Trp Met
        35                  40                  45

Gly Trp Met Asn Pro Asn Ser Ala Asn Thr Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Tyr Ala Ala Ala Gly Asp Gln Tyr Tyr Tyr Gly Met
            100                 105                 110

Asp Val Trp Gly Gln Gly Thr Leu Val Thr Val Ser Ser
        115                 120                 125

```
<210> SEQ ID NO 275
<211> LENGTH: 115
<212> TYPE: PRT
<213> ORGANISM: Artificial Sequence
<220> FEATURE:
<223> OTHER INFORMATION: Synthetic

<400> SEQUENCE: 275

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Ser Ser Tyr
                20                  25                  30

Ala Ile Ser Trp Val Arg Gln Ala Pro Gly Gln Gly Leu Glu Trp Met
            35                  40                  45

Gly Val Ile Asn Pro Ser Gly Gly Thr Thr Tyr Ala Lys Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Ala Phe Asp Tyr Trp Gly Gln Gly Thr Leu Val Thr
            100                 105                 110

Val Ser Ser
        115

<210> SEQ ID NO 276
<211> LENGTH: 123
<212> TYPE: PRT
<213> ORGANISM: Artificial Sequence
<220> FEATURE:
<223> OTHER INFORMATION: Synthetic

<400> SEQUENCE: 276

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asp Ser Gly Asp Thr Asn Phe Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Gly Asp Tyr Tyr Tyr Tyr Gly Met Asp Val
            100                 105                 110

Trp Gly Gln Gly Thr Met Val Thr Val Ser Ser
        115                 120

<210> SEQ ID NO 277
<211> LENGTH: 127
<212> TYPE: PRT
<213> ORGANISM: Artificial Sequence
<220> FEATURE:
<223> OTHER INFORMATION: Synthetic

<400> SEQUENCE: 277

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Met
        35                  40                  45

Gly Trp Met Asn Pro Asn Ser Ala Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ile Tyr Tyr Asp Ser Ser Gly Ser Tyr Tyr Tyr
            100                 105                 110

Gly Met Asp Val Trp Gly Gln Gly Thr Thr Val Thr Val Ser Ser
            115                 120                 125

<210> SEQ ID NO 278
<211> LENGTH: 122
<212> TYPE: PRT
<213> ORGANISM: Artificial Sequence
<220> FEATURE:
<223> OTHER INFORMATION: Synthetic

<400> SEQUENCE: 278

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Leu Ser Ser Ser Trp Tyr Ser Tyr Gly Met Asp Val Trp
            100                 105                 110

Gly Gln Gly Thr Thr Val Thr Val Ser Ser
            115                 120

<210> SEQ ID NO 279
<211> LENGTH: 119
<212> TYPE: PRT
<213> ORGANISM: Artificial Sequence
<220> FEATURE:
<223> OTHER INFORMATION: Synthetic

<400> SEQUENCE: 279

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ser Asp Tyr
            20                  25                  30

Gly Met Tyr Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

```
Lys Gly Arg Phe Thr Ile Ser Arg Asp Asp Ser Lys Asn Thr Leu Tyr
 65                  70                  75                  80

Leu Gln Met Asn Ser Leu Lys Thr Glu Asp Thr Ala Val Tyr Tyr Cys
                 85                  90                  95

Ala Arg Val Ser Gly Gly Ser Trp Tyr Asp Arg Leu Leu Gly Pro Gly
            100                 105                 110

Asn Pro Val Thr Val Ser Ser
            115
```

<210> SEQ ID NO 280
<211> LENGTH: 119
<212> TYPE: PRT
<213> ORGANISM: Artificial Sequence
<220> FEATURE:
<223> OTHER INFORMATION: Synthetic

<400> SEQUENCE: 280

```
Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Thr Phe Ser Ser Tyr
                 20                  25                  30

Gly Ile Asn Trp Val Arg Gln Ala Pro Gly Gln Gly Leu Glu Trp Met
             35                  40                  45

Gly Arg Ile Ile Pro Ile Phe Gly Ala Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Thr Tyr Phe Asp Trp Phe Phe Phe Asp Tyr Trp Gly Gln Gly
            100                 105                 110

Thr Leu Val Thr Val Ser Ser
            115
```

<210> SEQ ID NO 281
<211> LENGTH: 125
<212> TYPE: PRT
<213> ORGANISM: Artificial Sequence
<220> FEATURE:
<223> OTHER INFORMATION: Synthetic

<400> SEQUENCE: 281

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Trp Ile Asn Pro Asn Asn Gly Gly Thr Asn Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95
```

Ala Arg Gly Arg Tyr Ser Gly His Phe Gly Val Tyr Tyr Gly Met
            100                 105                 110

Asp Val Trp Gly Gln Gly Thr Thr Val Thr Val Ser Ser
        115                 120                 125

<210> SEQ ID NO 282
<211> LENGTH: 119
<212> TYPE: PRT
<213> ORGANISM: Artificial Sequence
<220> FEATURE:
<223> OTHER INFORMATION: Synthetic

<400> SEQUENCE: 282

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Tyr Met His Trp Val Arg Gln Ala Pro Gly Gln Gly Leu Glu Trp Met
        35                  40                  45

Ala Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Pro Tyr Gly Asp Tyr Gly Phe Asp Tyr Trp Gly Gln Gly
            100                 105                 110

Thr Leu Val Thr Val Ser Ser
        115

<210> SEQ ID NO 283
<211> LENGTH: 107
<212> TYPE: PRT
<213> ORGANISM: Artificial Sequence
<220> FEATURE:
<223> OTHER INFORMATION: Synthetic

<400> SEQUENCE: 283

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asp Ser Ile Pro Ile
                85                  90                  95

Thr Phe Gly Gln Gly Thr Lys Val Glu Ile Lys
            100                 105

<210> SEQ ID NO 284
<211> LENGTH: 107
<212> TYPE: PRT
<213> ORGANISM: Artificial Sequence
<220> FEATURE:
<223> OTHER INFORMATION: Synthetic

<400> SEQUENCE: 284

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Pro Gly Thr Lys Val Asp Ile Lys
            100                 105

<210> SEQ ID NO 285
<211> LENGTH: 107
<212> TYPE: PRT
<213> ORGANISM: Artificial Sequence
<220> FEATURE:
<223> OTHER INFORMATION: Synthetic

<400> SEQUENCE: 285

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Gly Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Pro Leu
                85                  90                  95

Thr Phe Gly Gly Gly Thr Lys Val Glu Ile Lys
            100                 105

<210> SEQ ID NO 286
<211> LENGTH: 107
<212> TYPE: PRT
<213> ORGANISM: Artificial Sequence
<220> FEATURE:
<223> OTHER INFORMATION: Synthetic

<400> SEQUENCE: 286

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser His
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 287
<211> LENGTH: 107
<212> TYPE: PRT
<213> ORGANISM: Artificial Sequence
<220> FEATURE:
<223> OTHER INFORMATION: Synthetic

<400> SEQUENCE: 287

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Arg Leu Pro Ile
                85                  90                  95

Thr Phe Gly Gln Gly Thr Arg Leu Glu Ile Lys
            100                 105

<210> SEQ ID NO 288
<211> LENGTH: 107
<212> TYPE: PRT
<213> ORGANISM: Artificial Sequence
<220> FEATURE:
<223> OTHER INFORMATION: Synthetic

<400> SEQUENCE: 288

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu His Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Phe Pro Leu
                85                  90                  95

Thr Phe Gly Gly Gly Thr Lys Val Glu Ile Lys
            100                 105

<210> SEQ ID NO 289
<211> LENGTH: 107
<212> TYPE: PRT
<213> ORGANISM: Artificial Sequence
<220> FEATURE:
<223> OTHER INFORMATION: Synthetic
```

<400> SEQUENCE: 289

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Pro Ile
                85                  90                  95

Thr Phe Gly Gln Gly Thr Lys Leu Glu Ile Lys
            100                 105

<210> SEQ ID NO 290
<211> LENGTH: 107
<212> TYPE: PRT
<213> ORGANISM: Artificial Sequence
<220> FEATURE:
<223> OTHER INFORMATION: Synthetic

<400> SEQUENCE: 290

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Leu
                85                  90                  95

Thr Phe Gly Gly Gly Thr Lys Val Glu Ile Lys
            100                 105

<210> SEQ ID NO 291
<211> LENGTH: 107
<212> TYPE: PRT
<213> ORGANISM: Artificial Sequence
<220> FEATURE:
<223> OTHER INFORMATION: Synthetic

<400> SEQUENCE: 291

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 292
<211> LENGTH: 107
<212> TYPE: PRT
<213> ORGANISM: Artificial Sequence
<220> FEATURE:
<223> OTHER INFORMATION: Synthetic

<400> SEQUENCE: 292

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Phe Asn Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Ser Phe Pro Leu
                85                  90                  95

Thr Phe Gly Pro Gly Thr Lys Val Asp Ile Lys
            100                 105

<210> SEQ ID NO 293
<211> LENGTH: 107
<212> TYPE: PRT
<213> ORGANISM: Artificial Sequence
<220> FEATURE:
<223> OTHER INFORMATION: Synthetic

<400> SEQUENCE: 293

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Lys Leu Glu Ile Lys
            100                 105

<210> SEQ ID NO 294
<211> LENGTH: 113
<212> TYPE: PRT
<213> ORGANISM: Artificial Sequence
<220> FEATURE:
<223> OTHER INFORMATION: Synthetic

<400> SEQUENCE: 294

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
            100                 105                 110

Lys

<210> SEQ ID NO 295
<211> LENGTH: 107
<212> TYPE: PRT
<213> ORGANISM: Artificial Sequence
<220> FEATURE:
<223> OTHER INFORMATION: Synthetic

<400> SEQUENCE: 295

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Thr Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Leu Pro Tyr
                85                  90                  95

Ser Phe Gly Gln Gly Thr Lys Leu Glu Ile Lys
            100                 105

<210> SEQ ID NO 296
<211> LENGTH: 107
<212> TYPE: PRT
<213> ORGANISM: Artificial Sequence
<220> FEATURE:
<223> OTHER INFORMATION: Synthetic

<400> SEQUENCE: 296

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Gly Asn Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Ser Thr Pro Tyr
                 85                  90                  95

Thr Phe Gly Gln Gly Thr Lys Leu Glu Ile Lys
            100                 105
```

<210> SEQ ID NO 297
<211> LENGTH: 107
<212> TYPE: PRT
<213> ORGANISM: Artificial Sequence
<220> FEATURE:
<223> OTHER INFORMATION: Synthetic

<400> SEQUENCE: 297

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Gly Thr Ser Pro Phe
                 85                  90                  95

Thr Phe Gly Gln Gly Thr Arg Leu Glu Ile Lys
            100                 105
```

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Asn
                20                  25                  30

Leu Asn Trp Tyr Gln Gln Lys Pro Gly Lys Ala Pro Lys Leu Leu Ile
             35                  40                  45

Tyr Ala Ala Ser Ile Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Thr Thr Leu
                 85                  90                  95

Thr Phe Gly Pro Gly Thr Lys Val Asp Ile Lys
            100                 105
```

<210> SEQ ID NO 299
<211> LENGTH: 107
<212> TYPE: PRT
<213> ORGANISM: Artificial Sequence
<220> FEATURE:
<223> OTHER INFORMATION: Synthetic

<400> SEQUENCE: 299

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Phe
            20                  25                  30

Leu Asn Trp Tyr Gln Gln Lys Pro Gly Lys Ala Pro Lys Leu Leu Ile
        35                  40                  45

Tyr Ser Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gln Gly Thr Lys Val Glu Ile Lys
            100                 105

<210> SEQ ID NO 300
<211> LENGTH: 107
<212> TYPE: PRT
<213> ORGANISM: Artificial Sequence
<220> FEATURE:
<223> OTHER INFORMATION: Synthetic

<400> SEQUENCE: 300

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Gly Asn Trp
            20                  25                  30

Leu Ala Trp Tyr His Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Thr Pro Tyr
                85                  90                  95

Thr Phe Gly Gln Gly Thr Lys Leu Glu Ile Lys
            100                 105

<210> SEQ ID NO 301
<211> LENGTH: 112
<212> TYPE: PRT
<213> ORGANISM: Artificial Sequence
<220> FEATURE:
<223> OTHER INFORMATION: Synthetic

<400> SEQUENCE: 301

Asp Ile Val Met Thr Gln Ser Pro Leu Phe Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

-continued

Ser Arg Val Glu Ala Glu Asp Val Gly Val Tyr Tyr Cys Met Gln Gly
                85                  90                  95

Ala His Trp Pro Tyr Thr Phe Gly Gln Gly Thr Lys Leu Glu Ile Lys
            100                 105                 110

<210> SEQ ID NO 302
<211> LENGTH: 107
<212> TYPE: PRT
<213> ORGANISM: Artificial Sequence
<220> FEATURE:
<223> OTHER INFORMATION: Synthetic

<400> SEQUENCE: 302

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 303
<211> LENGTH: 107
<212> TYPE: PRT
<213> ORGANISM: Artificial Sequence
<220> FEATURE:
<223> OTHER INFORMATION: Synthetic

<400> SEQUENCE: 303

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Glu Ile Gly Asn Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 304
<211> LENGTH: 112
<212> TYPE: PRT
<213> ORGANISM: Artificial Sequence
<220> FEATURE:
<223> OTHER INFORMATION: Synthetic

<400> SEQUENCE: 304

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Ala Ala Ser Ser Leu Gln Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 305
<211> LENGTH: 107
<212> TYPE: PRT
<213> ORGANISM: Artificial Sequence
<220> FEATURE:
<223> OTHER INFORMATION: Synthetic

<400> SEQUENCE: 305

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Leu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Gly Ile Pro Leu
                85                  90                  95

Thr Phe Gly Gly Gly Thr Lys Val Glu Ile Lys
            100                 105

<210> SEQ ID NO 306
<211> LENGTH: 107
<212> TYPE: PRT
<213> ORGANISM: Artificial Sequence
<220> FEATURE:
<223> OTHER INFORMATION: Synthetic

<400> SEQUENCE: 306

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Thr Phe Pro Leu
                85                  90                  95

Thr Phe Gly Gly Gly Thr Lys Val Glu Ile Lys
            100                 105

<210> SEQ ID NO 307
<211> LENGTH: 107
<212> TYPE: PRT
<213> ORGANISM: Artificial Sequence
<220> FEATURE:
<223> OTHER INFORMATION: Synthetic

<400> SEQUENCE: 307

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Phe Pro Leu
                85                  90                  95

Thr Phe Gly Pro Gly Thr Lys Val Asp Ile Lys
            100                 105

<210> SEQ ID NO 308
<211> LENGTH: 106
<212> TYPE: PRT
<213> ORGANISM: Artificial Sequence
<220> FEATURE:
<223> OTHER INFORMATION: Synthetic

<400> SEQUENCE: 308

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Phe Gly Pro Gly Thr Lys Val Asp Ile Lys
            100                 105

<210> SEQ ID NO 309
<211> LENGTH: 107
<212> TYPE: PRT
<213> ORGANISM: Artificial Sequence
<220> FEATURE:
<223> OTHER INFORMATION: Synthetic

```
<400> SEQUENCE: 309

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Lys Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105

<210> SEQ ID NO 310
<211> LENGTH: 107
<212> TYPE: PRT
<213> ORGANISM: Artificial Sequence
<220> FEATURE:
<223> OTHER INFORMATION: Synthetic

<400> SEQUENCE: 310

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Gly Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Phe Pro Pro
                85                  90                  95

Thr Phe Gly Gly Gly Thr Lys Val Glu Ile Lys
            100                 105

<210> SEQ ID NO 311
<211> LENGTH: 107
<212> TYPE: PRT
<213> ORGANISM: Artificial Sequence
<220> FEATURE:
<223> OTHER INFORMATION: Synthetic

<400> SEQUENCE: 311

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Leu Gln Ala Ile Ser Phe Pro Phe
                85                  90                  95

Thr Phe Gly Pro Gly Thr Lys Val Asp Ile Lys
            100                 105

<210> SEQ ID NO 312
<211> LENGTH: 107
<212> TYPE: PRT
<213> ORGANISM: Artificial Sequence
<220> FEATURE:
<223> OTHER INFORMATION: Synthetic

<400> SEQUENCE: 312

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Asp Thr Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser Leu Pro Trp
                85                  90                  95

Thr Phe Gly Gln Gly Thr Lys Leu Glu Ile Lys
            100                 105

<210> SEQ ID NO 313
<211> LENGTH: 107
<212> TYPE: PRT
<213> ORGANISM: Artificial Sequence
<220> FEATURE:
<223> OTHER INFORMATION: Synthetic

<400> SEQUENCE: 313

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ser Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Tyr
                85                  90                  95

Thr Phe Gly Gln Gly Thr Lys Leu Glu Ile Lys
            100                 105

<210> SEQ ID NO 314
<211> LENGTH: 107
<212> TYPE: PRT
<213> ORGANISM: Artificial Sequence
<220> FEATURE:
<223> OTHER INFORMATION: Synthetic

<400> SEQUENCE: 314

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Phe Pro Leu
                85                  90                  95

Thr Phe Gly Gln Gly Thr Lys Val Glu Ile Lys
            100                 105

<210> SEQ ID NO 315
<211> LENGTH: 113
<212> TYPE: PRT
<213> ORGANISM: Artificial Sequence
<220> FEATURE:
<223> OTHER INFORMATION: Synthetic

<400> SEQUENCE: 315

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Phe Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Leu Thr Phe Gly Gly Gly Thr Lys Val Glu Ile
            100                 105                 110

Lys

<210> SEQ ID NO 316
<211> LENGTH: 113
<212> TYPE: PRT
<213> ORGANISM: Artificial Sequence
<220> FEATURE:
<223> OTHER INFORMATION: Sythnetic

<400> SEQUENCE: 316

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Ala Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Lys Ser Ala Pro Tyr Thr Phe Gly Gln Gly Thr Lys Val Glu Ile
            100                 105                 110

Lys

<210> SEQ ID NO 317
<211> LENGTH: 107
<212> TYPE: PRT
<213> ORGANISM: Artificial Sequence
<220> FEATURE:
<223> OTHER INFORMATION: Synthetic

<400> SEQUENCE: 317

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Phe Pro Leu
                85                  90                  95

Thr Phe Gly Pro Gly Thr Lys Val Asp Ile Lys
            100                 105

<210> SEQ ID NO 318
<211> LENGTH: 107
<212> TYPE: PRT
<213> ORGANISM: Artificial Sequence
<220> FEATURE:
<223> OTHER INFORMATION: Synthetic

<400> SEQUENCE: 318

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg His
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Gln Thr Pro Leu
                85                  90                  95

Thr Phe Gly Gly Gly Thr Lys Val Glu Ile Lys
            100                 105

<210> SEQ ID NO 319
<211> LENGTH: 113
<212> TYPE: PRT
<213> ORGANISM: Artificial Sequence
<220> FEATURE:

<223> OTHER INFORMATION: Synthetic

<400> SEQUENCE: 319

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Ile Arg Glu Ser Gly Val
65                  70                  75                  80

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Tyr Tyr Ser Ser Pro Phe Thr Phe Gly Gln Gly Thr Lys Leu Glu Ile
                100                 105                 110

Lys

<210> SEQ ID NO 320
<211> LENGTH: 112
<212> TYPE: PRT
<213> ORGANISM: Artificial Sequence
<220> FEATURE:
<223> OTHER INFORMATION: Synthetic

<400> SEQUENCE: 320

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Asp Ala Ser Asn Leu His Ala Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Gln Ala Pro Val Thr Phe Gly Gln Gly Thr Arg Leu Glu Ile Lys
                100                 105                 110

<210> SEQ ID NO 321
<211> LENGTH: 107
<212> TYPE: PRT
<213> ORGANISM: Artificial Sequence
<220> FEATURE:
<223> OTHER INFORMATION: Synthetic

<400> SEQUENCE: 321

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Ser Phe Pro Leu
                 85                  90                  95

Thr Phe Gly Gly Gly Thr Lys Leu Glu Ile Lys
            100                 105

<210> SEQ ID NO 322
<211> LENGTH: 107
<212> TYPE: PRT
<213> ORGANISM: Artificial Sequence
<220> FEATURE:
<223> OTHER INFORMATION: Synthetic

<400> SEQUENCE: 322

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Thr Val Arg Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Tyr Arg Thr Pro Leu
                 85                  90                  95

Thr Phe Gly Gln Gly Thr Lys Val Glu Ile Lys
            100                 105

<210> SEQ ID NO 323
<211> LENGTH: 10
<212> TYPE: PRT
<213> ORGANISM: Artificial Sequence
<220> FEATURE:
<223> OTHER INFORMATION: Synthetic

<400> SEQUENCE: 323

Val Arg Gly Phe Ser Phe Trp Phe Glu Pro
 1               5                  10

<210> SEQ ID NO 324
<211> LENGTH: 119
<212> TYPE: PRT
<213> ORGANISM: Artificial Sequence
<220> FEATURE:
<223> OTHER INFORMATION: Synthetic

<400> SEQUENCE: 324

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ala Val Ile Ser Tyr Asp Gly Arg Ile Lys Asp Tyr Ala Asp Ser Val
 50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Arg Val Arg Gly Phe Ser Phe Trp Phe Gly Pro Trp Gly Gln Gly
            100                 105                 110

Thr Leu Val Thr Val Ser Ser
        115

<210> SEQ ID NO 325
<211> LENGTH: 214
<212> TYPE: PRT
<213> ORGANISM: Artificial Sequence
<220> FEATURE:
<223> OTHER INFORMATION: Synthetic

<400> SEQUENCE: 325

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asp Ser Ile Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 326
<211> LENGTH: 214
<212> TYPE: PRT
<213> ORGANISM: Artificial Sequence
<220> FEATURE:
<223> OTHER INFORMATION: Synthetic

<400> SEQUENCE: 326

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Asn Trp Tyr Gln Gln Lys Pro Gly Lys Ala Pro Lys Leu Leu Ile
        35                  40                  45
```

Tyr Ala Ala Ser Arg Leu Gln Ser Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 327
<211> LENGTH: 214
<212> TYPE: PRT
<213> ORGANISM: Artificial Sequence
<220> FEATURE:
<223> OTHER INFORMATION: Synthetic

<400> SEQUENCE: 327

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Leu Ala Ser Ser Leu Gln Ser Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Gly Ile Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

-continued

Ala Cys Glu Val Thr His Gln Gly Leu Ser Ser Pro Val Thr Lys Ser
        195                 200                 205

Phe Asn Arg Gly Glu Cys
    210

<210> SEQ ID NO 328
<211> LENGTH: 458
<212> TYPE: PRT
<213> ORGANISM: Artificial Sequence
<220> FEATURE:
<223> OTHER INFORMATION: Synthetic

<400> SEQUENCE: 328

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Gln Trp Val Arg Gln Ala Pro Gly Gln Gly Leu Glu Trp Met
        35                  40                  45

Gly Trp Ile Asn Pro Lys Ser Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Thr Tyr Leu Arg Thr Gly Ser Ser Leu Ser Gly Tyr Tyr
            100                 105                 110

Tyr Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

```
Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Glu Glu
            355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 329
<211> LENGTH: 458
<212> TYPE: PRT
<213> ORGANISM: Artificial Sequence
<220> FEATURE:
<223> OTHER INFORMATION: Synthetic

<400> SEQUENCE: 329

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Gln Trp Val Arg Gln Ala Pro Gly Gln Gly Leu Glu Trp Met
            35                  40                  45

Gly Trp Ile Asn Pro Lys Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Thr Tyr Leu Arg Thr Gly Ser Ser Leu Ser Gly Tyr Tyr
            100                 105                 110

Tyr Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240
```

```
Pro Ala Pro Glu Leu Leu Gly Gly Pro Ser Val Phe Leu Phe Pro Pro
            245                 250                 255

Lys Pro Lys Asp Thr Leu Met Ile Ser Arg Thr Pro Glu Val Thr Cys
            260                 265                 270

Val Val Val Asp Val Glu His Glu Asp Pro Glu Val Lys Phe Asn Trp
            275                 280                 285

Tyr Val Asp Gly Val Glu Val His Asn Ala Lys Thr Lys Pro Arg Glu
            290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
            355                 360                 365

Met Thr Lys Asn Gln Val Ser Leu Thr Cys Leu Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
            450                 455

<210> SEQ ID NO 330
<211> LENGTH: 458
<212> TYPE: PRT
<213> ORGANISM: Artificial Sequence
<220> FEATURE:
<223> OTHER INFORMATION: Synthetic

<400> SEQUENCE: 330

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Gln Trp Val Arg Gln Ala Pro Gly Gln Gly Leu Glu Trp Met
            35                  40                  45

Gly Trp Ile Asn Pro Lys Ser Gly Gly Thr Asn Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Gly Thr Tyr Leu Arg Thr Gly Ser Ser Leu Ser Gly Tyr Tyr
            100                 105                 110

Tyr Gly Met Asp Val Trp Gly Gln Gly Thr Thr Val Thr Val Ser Ser
            115                 120                 125

Ala Ser Thr Lys Gly Pro Ser Val Phe Pro Leu Ala Pro Ser Ser Lys
            130                 135                 140
```

-continued

```
Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
            165                 170                 175

Gly Val His Thr Phe Pro Ala Val Leu Gln Ser Ser Gly Leu Tyr Ser
        180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
        210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
            245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
            340                 345                 350

Gln Pro Arg Arg Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 331
<211> LENGTH: 458
<212> TYPE: PRT
<213> ORGANISM: Artificial Sequence
<220> FEATURE:
<223> OTHER INFORMATION: Synthetic

<400> SEQUENCE: 331

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Gln Trp Val Arg Gln Ala Pro Gly Gln Gly Leu Glu Trp Met
        35                  40                  45
```

```
Gly Trp Ile Asn Pro Lys Ser Gly Gly Thr Asn Tyr Ala Gln Lys Phe
    50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Gly Thr Tyr Leu Arg Thr Gly Ser Ser Leu Ser Gly Tyr Tyr
            100                 105                 110
Tyr Gly Met Asp Val Trp Gly Gln Gly Thr Thr Val Thr Val Ser Ser
            115                 120                 125
Ala Ser Thr Lys Gly Pro Ser Val Phe Pro Leu Ala Pro Ser Ser Lys
        130                 135                 140
Ser Thr Ser Gly Gly Thr Ala Ala Leu Gly Cys Leu Val Lys Asp Tyr
145                 150                 155                 160
Phe Pro Glu Pro Val Thr Val Ser Trp Asn Ser Gly Ala Leu Thr Ser
                165                 170                 175
Gly Val His Thr Phe Pro Ala Val Leu Gln Ser Ser Gly Leu Tyr Ser
            180                 185                 190
Leu Ser Ser Val Val Thr Val Pro Ser Ser Ser Leu Gly Thr Gln Thr
        195                 200                 205
Tyr Ile Cys Asn Val Asn His Lys Pro Ser Asn Thr Lys Val Asp Lys
210                 215                 220
Arg Val Glu Pro Lys Ser Cys Asp Lys Thr His Thr Cys Pro Pro Cys
225                 230                 235                 240
Pro Ala Pro Glu Leu Leu Gly Gly Pro Ser Val Phe Leu Phe Pro Pro
                245                 250                 255
Lys Pro Lys Asp Thr Leu Met Ile Ser Arg Thr Pro Glu Val Thr Cys
            260                 265                 270
Val Val Val Asp Val Glu His Glu Asp Pro Glu Val Lys Phe Asn Trp
        275                 280                 285
Tyr Val Asp Gly Val Glu Val His Asn Ala Lys Thr Lys Pro Arg Glu
        290                 295                 300
Glu Gln Tyr Asn Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Pro Ala Pro Ile Glu Lys Thr Ile Ser Lys Ala Lys Gly
            340                 345                 350
Gln Pro Arg Arg Pro Gln Val Tyr Thr Leu Pro Pro Ser Arg Glu Glu
        355                 360                 365
Met Thr Lys Asn Gln Val Ser Leu Thr Cys Leu Val Lys Gly Phe Tyr
        370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Tyr Ser Lys Leu Thr Val Asp Lys Ser Arg Trp Gln Gln Gly Asn
            420                 425                 430
Val Phe Ser Cys Ser Val Met His Glu Ala Leu His Asn His Tyr Thr
        435                 440                 445
Gln Lys Ser Leu Ser Leu Ser Pro Gly Lys
        450                 455
```

```
<210> SEQ ID NO 332
<211> LENGTH: 458
<212> TYPE: PRT
<213> ORGANISM: Artificial Sequence
<220> FEATURE:
<223> OTHER INFORMATION: Synthetic

<400> SEQUENCE: 332

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Gln Trp Val Arg Gln Ala Pro Gly Gln Gly Leu Glu Trp Met
            35                  40                  45

Gly Trp Ile Asn Pro Lys Ser Gly Thr Asn Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Thr Tyr Leu Arg Thr Gly Ser Ser Leu Ser Gly Tyr Tyr
            100                 105                 110

Tyr Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365
```

Met Thr Lys Asn Gln Val Ser Leu Thr Cys Leu Val Lys Gly Phe Tyr
                370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
                435                 440                 445

Gln Lys Ser Leu Ser Leu Ser Pro Gly Lys
                450                 455

<210> SEQ ID NO 333
<211> LENGTH: 458
<212> TYPE: PRT
<213> ORGANISM: Artificial Sequence
<220> FEATURE:
<223> OTHER INFORMATION: Synthetic

<400> SEQUENCE: 333

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Gln Trp Val Arg Gln Ala Pro Gly Gln Gly Leu Glu Trp Met
                35                  40                  45

Gly Trp Ile Asn Pro Lys Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Thr Tyr Leu Arg Thr Gly Ser Ser Leu Ser Gly Tyr Tyr
                100                 105                 110

Tyr Gly Met Asp Val Trp Gly Gln Gly Thr Thr Val Thr Val Ser Ser
                115                 120                 125

Ala Ser Thr Lys Gly Pro Ser Val Phe Pro Leu Ala Pro Ser Ser Lys
130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
                180                 185                 190

Leu Ser Ser Val Val Thr Val Pro Ser Ser Ser Leu Gly Thr Gln Thr
                195                 200                 205

Tyr Ile Cys Asn Val Asn His Lys Pro Ser Asn Thr Lys Val Asp Lys
                210                 215                 220

Arg Val Glu Pro Lys Ser Cys Asp Lys Thr His Thr Cys Pro Pro Cys
225                 230                 235                 240

Pro Ala Pro Glu Leu Leu Ala Gly Pro Ser Val Phe Leu Phe Pro Pro
                245                 250                 255

Lys Pro Lys Asp Thr Leu Met Ile Ser Arg Thr Pro Glu Val Thr Cys
                260                 265                 270

```
Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
        290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 334
<211> LENGTH: 455
<212> TYPE: PRT
<213> ORGANISM: Artificial Sequence
<220> FEATURE:
<223> OTHER INFORMATION: Synthetic

<400> SEQUENCE: 334

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Trp Ile Gln Trp Val Arg Gln Ala Pro Gly Gln Gly Leu Glu Trp Met
        35                  40                  45

Gly Trp Ile Asn Pro Asn Ser Gly Gly Thr Arg Tyr Ala Arg Asn Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Arg Tyr Tyr Tyr Gly Ser Gly Ser Gln Tyr His Ala Phe
            100                 105                 110

Asp Ile Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175
```

Thr Phe Pro Ala Val Leu Gln Ser Ser Gly Leu Tyr Ser Leu Ser Ser
                180                 185                 190

Val Val Thr Val Pro Ser Ser Leu Gly Thr Gln Thr Tyr Ile Cys
            195                 200                 205

Asn Val Asn His Lys Pro Ser Asn Thr Lys Val Asp Lys Arg Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
450                 455

<210> SEQ ID NO 335
<211> LENGTH: 455
<212> TYPE: PRT
<213> ORGANISM: Artificial Sequence
<220> FEATURE:
<223> OTHER INFORMATION: Synthetic

<400> SEQUENCE: 335

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Trp Ile Gln Trp Val Arg Gln Ala Pro Gly Gln Gly Leu Glu Trp Met
        35                  40                  45

Gly Trp Ile Asn Pro Asn Ser Gly Gly Thr Arg Tyr Ala Arg Asn Phe
    50                  55                  60

Gln Gly Arg Val Thr Met Thr Arg Asp Thr Ser Thr Ser Thr Val Tyr
65                  70                  75                  80

```
Met Glu Leu Ser Ser Leu Arg Ser Glu Asp Thr Ala Val Tyr Tyr Cys
                85                  90                  95

Ala Arg Gly Arg Tyr Tyr Tyr Gly Ser Gly Ser Gln Tyr His Ala Phe
            100                 105                 110

Asp Ile Trp Gly Gln Gly Thr Met Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Arg Val Glu
210                 215                 220

Pro Lys Ser Cys Asp Lys Thr His Thr Cys Pro Pro Cys Pro Ala Pro
225                 230                 235                 240

Glu Leu Leu Ala Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 336
<211> LENGTH: 455
<212> TYPE: PRT
<213> ORGANISM: Artificial Sequence
<220> FEATURE:
<223> OTHER INFORMATION: Synthetic
```

<400> SEQUENCE: 336

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Trp Ile Gln Trp Val Arg Gln Ala Pro Gly Gln Gly Leu Glu Trp Met
        35                  40                  45

Gly Trp Ile Asn Pro Asn Ser Gly Gly Thr Arg Tyr Ala Arg Asn Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Arg Tyr Tyr Gly Ser Gly Ser Gln Tyr His Ala Phe
            100                 105                 110

Asp Ile Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400
```

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
        450                 455

<210> SEQ ID NO 337
<211> LENGTH: 455
<212> TYPE: PRT
<213> ORGANISM: Artificial Sequence
<220> FEATURE:
<223> OTHER INFORMATION: Synthetic

<400> SEQUENCE: 337

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Trp Ile Gln Trp Val Arg Gln Ala Pro Gly Gln Gly Leu Glu Trp Met
        35                  40                  45

Gly Trp Ile Asn Pro Asn Ser Gly Gly Thr Arg Tyr Ala Arg Asn Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Arg Tyr Tyr Tyr Gly Ser Gly Ser Gln Tyr His Ala Phe
            100                 105                 110

Asp Ile Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Ala Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
        340                 345                 350

Glu Pro Gln Val Tyr Thr Leu Pro Pro Ser Arg Glu Glu Met Thr Lys
    355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
450                 455

<210> SEQ ID NO 338
<211> LENGTH: 451
<212> TYPE: PRT
<213> ORGANISM: Artificial Sequence
<220> FEATURE:
<223> OTHER INFORMATION: Synthetic

<400> SEQUENCE: 338

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Trp Ile Gln Trp Val Arg Gln Ala Pro Gly Gln Gly Leu Glu Trp Met
        35                  40                  45

Gly Trp Ile Asn Pro Asn Ser Gly Gly Thr Arg Tyr Ala Arg Asn Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Arg Tyr Tyr Gly Ser Gly Ser Gln Tyr His Ala Phe
            100                 105                 110

Asp Ile Trp Gly Gln Gly Thr Met Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

```
Asn Val Asp His Lys Pro Ser Asn Thr Lys Val Asp Lys Thr Val Glu
            210                 215                 220

Arg Lys Ser Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 339
<211> LENGTH: 455
<212> TYPE: PRT
<213> ORGANISM: Artificial Sequence
<220> FEATURE:
<223> OTHER INFORMATION: Synthetic

<400> SEQUENCE: 339

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Trp Ile Gln Trp Val Arg Gln Ala Pro Gly Gln Gly Leu Glu Trp Met
        35                  40                  45

Gly Trp Ile Asn Pro Asn Ser Gly Gly Thr Arg Tyr Ala Arg Asn Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Arg Tyr Tyr Tyr Gly Ser Gly Ser Gln Tyr His Ala Phe
            100                 105                 110
```

Asp Ile Trp Gly Gln Gly Thr Met Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Arg Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Arg Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 340
<211> LENGTH: 449
<212> TYPE: PRT
<213> ORGANISM: Artificial Sequence
<220> FEATURE:
<223> OTHER INFORMATION: Synthetic

<400> SEQUENCE: 340

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ala Val Ile Ser Tyr Asp Gly Arg Ile Lys Asp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Arg Gly Phe Ser Phe Trp Phe Asp Pro Trp Gly Gln Gly
             100                 105                 110

Thr Leu Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
         130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Arg Val Glu Pro Lys Ser Cys Asp Lys
 210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
 290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Glu Glu Met Thr Lys Asn Gln Val Ser Leu Thr
         355                 360                 365

Cys Leu Val Lys Gly Phe Tyr Pro Ser Asp Ile Ala Val Glu Trp Glu
 370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430
```

```
Ala Leu His Asn His Tyr Thr Gln Lys Ser Leu Ser Leu Ser Pro Gly
            435                 440                 445

Lys

<210> SEQ ID NO 341
<211> LENGTH: 449
<212> TYPE: PRT
<213> ORGANISM: Artificial Sequence
<220> FEATURE:
<223> OTHER INFORMATION: Synthetic

<400> SEQUENCE: 341

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Val Ile Ser Tyr Asp Gly Arg Ile Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Gly Phe Ser Phe Trp Phe Asp Pro Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

Thr Ile Ser Lys Ala Lys Gly Gln Pro Arg Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 342
<211> LENGTH: 449
<212> TYPE: PRT
<213> ORGANISM: Artificial Sequence
<220> FEATURE:
<223> OTHER INFORMATION: Synthetic

<400> SEQUENCE: 342

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Val Ile Ser Tyr Asp Gly Arg Ile Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Val Arg Gly Phe Ser Phe Trp Phe Asp Pro Trp Gly Gln Gly
        100                 105                 110

Thr Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Ala Gly Pro
225                 230                 235                 240

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 343
<211> LENGTH: 445
<212> TYPE: PRT
<213> ORGANISM: Artificial Sequence
<220> FEATURE:
<223> OTHER INFORMATION: Synthetic

<400> SEQUENCE: 343

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Val Ile Ser Tyr Asp Gly Arg Ile Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Gly Phe Ser Trp Phe Asp Pro Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Ser Cys Val Glu
        210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
        260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
        290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
            435                 440                 445

<210> SEQ ID NO 344
<211> LENGTH: 449
<212> TYPE: PRT
<213> ORGANISM: Artificial Sequence
<220> FEATURE:
<223> OTHER INFORMATION: Synthetic

<400> SEQUENCE: 344

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Val Ile Ser Tyr Asp Gly Arg Ile Lys Asp Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Arg Gly Phe Ser Phe Trp Phe Asp Pro Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 345
<211> LENGTH: 449
<212> TYPE: PRT
```

<213> ORGANISM: Artificial Sequence
<220> FEATURE:
<223> OTHER INFORMATION: Synthetic

<400> SEQUENCE: 345

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Val Ile Ser Tyr Asp Gly Arg Ile Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Gly Phe Ser Phe Trp Phe Glu Pro Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 346
<211> LENGTH: 209
<212> TYPE: PRT
<213> ORGANISM: Homo sapiens
<220> FEATURE:
<221> NAME/KEY: MISC_FEATURE
<223> OTHER INFORMATION: Dectin-2

<400> SEQUENCE: 346

Met Met Gln Glu Gln Gln Pro Gln Ser Thr Glu Lys Arg Gly Trp Leu
1               5                   10                  15

Ser Leu Arg Leu Trp Ser Val Ala Gly Ile Ser Ile Ala Leu Leu Ser
                20                  25                  30

Ala Cys Phe Ile Val Ser Cys Val Val Thr Tyr His Phe Thr Tyr Gly
            35                  40                  45

Glu Thr Gly Lys Arg Leu Ser Glu Leu His Ser Tyr His Ser Ser Leu
        50                  55                  60

Thr Cys Phe Ser Glu Gly Thr Lys Val Pro Ala Trp Gly Cys Cys Pro
65                  70                  75                  80

Ala Ser Trp Lys Ser Phe Gly Ser Ser Cys Tyr Phe Ile Ser Ser Glu
                85                  90                  95

Glu Lys Val Trp Ser Lys Ser Gln Asn Cys Val Glu Met Gly Ala
            100                 105                 110

His Leu Val Val Phe Asn Thr Glu Ala Glu Gln Asn Phe Ile Val Gln
        115                 120                 125

Gln Leu Asn Glu Ser Phe Ser Tyr Phe Leu Gly Leu Ser Asp Pro Gln
    130                 135                 140

Gly Asn Asn Asn Trp Gln Trp Ile Asp Lys Thr Pro Tyr Glu Lys Asn
145                 150                 155                 160

Val Arg Phe Trp His Leu Gly Glu Pro Asn His Ser Ala Glu Gln Cys
                165                 170                 175

Ala Ser Ile Val Phe Trp Lys Pro Thr Gly Trp Gly Trp Asn Asp Val
            180                 185                 190

Ile Cys Glu Thr Arg Arg Asn Ser Ile Cys Glu Met Asn Lys Ile Tyr
        195                 200                 205

Leu
```